(12) United States Patent
Dellamano et al.

(10) Patent No.: US 9,889,308 B2
(45) Date of Patent: *Feb. 13, 2018

(54) IMPLANTABLE HEAD LOCATED RADIOFREQUENCY COUPLED NEUROSTIMULATION SYSTEM FOR HEAD PAIN

(71) Applicant: SYNTILLA MEDICAL LLC, Southlake, TX (US)

(72) Inventors: Harry Dellamano, Santa Rosa Valley, CA (US); Kenneth Lyle Reed, Dallas, TX (US); Robert Raymond Bulger, Dallas, TX (US); Claire Denault, Southlake, TX (US); Michael Steven Colvin, Newbury Park, CA (US); Paul Griffith, Santa Rosa Valley, CA (US); Francis Menezes, Simi Valley, CA (US)

(73) Assignee: Syntilla Medical LLC, Southlake, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/402,090

(22) Filed: Jan. 9, 2017

(65) Prior Publication Data

US 2017/0113054 A1    Apr. 27, 2017

Related U.S. Application Data

(63) Continuation of application No. 14/990,678, filed on Jan. 7, 2016, now Pat. No. 9,539,432, which is a
(Continued)

(51) Int. Cl.
*A61N 1/372*    (2006.01)
*A61N 1/375*    (2006.01)
(Continued)

(52) U.S. Cl.
CPC ......... *A61N 1/3787* (2013.01); *A61N 1/0504* (2013.01); *A61N 1/0526* (2013.01);
(Continued)

(58) Field of Classification Search
CPC .. A61N 1/3787; A61N 1/0504; A61N 1/0526; A61N 1/0551; A61N 1/37229; A61N 1/36075
See application file for complete search history.

(56) References Cited

U.S. PATENT DOCUMENTS

| | | |
|---|---|---|
| 3,727,616 A | 4/1973 | Lenzkes |
| 4,612,934 A | 9/1986 | Borkan |

(Continued)

FOREIGN PATENT DOCUMENTS

| | | |
|---|---|---|
| CA | 2734775 | 2/2010 |
| EP | 0007157 | 1/1980 |
| WO | 2009158389 | 12/2009 |

OTHER PUBLICATIONS

PCT: International Search Report and Written Opinion of PCT/US14/51235 (related application); dated Feb. 19, 2015; 24 pages, dated Feb. 19, 2015.
(Continued)

*Primary Examiner* — Catherine Voorhees
(74) *Attorney, Agent, or Firm* — Munck Wilson Mandala, LLP

(57) ABSTRACT

A system is provided for driving an implantable neurostimulator lead, the lead having an associated plurality of electrodes disposed in at least one array on the lead. The system comprises an implantable pulse generator (IPG), the IPG including an electrode driver, a load system for determining load requirements, an IPG power coupler, and an IPG communication system. The system also includes an external unit, which includes an external variable power genera-
(Continued)

tor, an external power coupler, an external communication system, and a controller for varying the power level of the variable power generator.

20 Claims, 37 Drawing Sheets

Related U.S. Application Data continuation of application No. 14/989,674, filed on Jan. 6, 2016, now Pat. No. 9,498,635, which is a continuation-in-part of application No. 14/879,943, filed on Oct. 9, 2015, which is a continuation-in-part of application No. 14/717,912, filed on May 20, 2015, which is a continuation of application No. 14/460,139, filed on Aug. 14, 2014, now Pat. No. 9,042,991.

(60) Provisional application No. 61/894,795, filed on Oct. 23, 2013.

(51) Int. Cl.
A61N 1/05 (2006.01)
A61N 1/378 (2006.01)
A61N 1/36 (2006.01)

(52) U.S. Cl.
CPC ......... *A61N 1/0529* (2013.01); *A61N 1/0551* (2013.01); *A61N 1/36075* (2013.01); *A61N 1/375* (2013.01); *A61N 1/37211* (2013.01); *A61N 1/37229* (2013.01)

(56) References Cited

U.S. PATENT DOCUMENTS

| | | | |
|---|---|---|---|
| 4,793,353 A | 12/1988 | Borkan | |
| 4,819,647 A | 4/1989 | Byers | |
| 5,000,194 A | 3/1991 | Van Den Honert et al. | |
| 5,037,497 A | 8/1991 | Stypulkowski | |
| 5,215,086 A | 6/1993 | Terry, Jr. et al. | |
| 5,279,292 A | 1/1994 | Baumann et al. | |
| 5,545,219 A | 8/1996 | Kuzma | |
| 5,569,307 A * | 10/1996 | Schulman ......... | A61N 1/36032 607/55 |
| 5,615,100 A | 3/1997 | Radecker et al. | |
| 5,733,313 A | 3/1998 | Barreras, Sr. | |
| 5,876,425 A * | 3/1999 | Gord ................ | A61N 1/36032 607/33 |
| 5,905,646 A | 5/1999 | Crewson et al. | |
| 6,016,449 A | 1/2000 | Fischell et al. | |
| 6,088,619 A | 7/2000 | Hein et al. | |
| 6,178,353 B1 | 1/2001 | Griffith et al. | |
| 6,236,892 B1 | 5/2001 | Feler | |
| 6,246,911 B1 | 6/2001 | Seligman | |
| 6,456,883 B1 | 9/2002 | Torgerson et al. | |
| 6,516,227 B1 | 2/2003 | Meadows | |
| 6,529,774 B1 | 3/2003 | Greene | |
| 6,597,954 B1 | 7/2003 | Pless et al. | |
| 6,606,521 B2 | 8/2003 | Paspa et al. | |
| 6,618,623 B1 | 9/2003 | Pless et al. | |
| 6,895,283 B2 | 5/2005 | Erickson et al. | |
| 6,920,359 B2 | 7/2005 | Meadows et al. | |
| 7,127,298 B1 | 10/2006 | He et al. | |
| 7,319,906 B2 | 1/2008 | Kuzma et al. | |
| 7,437,197 B2 | 10/2008 | Harris et al. | |
| 7,499,755 B2 | 3/2009 | Cross, Jr. | |
| 7,599,743 B2 | 10/2009 | Hassler, Jr. et al. | |
| 7,676,273 B2 | 3/2010 | Goetz et al. | |
| 7,706,892 B2 | 4/2010 | Colvin et al. | |
| 7,729,781 B2 | 6/2010 | Swoyer et al. | |
| 7,769,461 B2 | 8/2010 | Whitehurst et al. | |
| 7,894,905 B2 | 2/2011 | Pless et al. | |
| 8,027,735 B1 | 9/2011 | Tziviskos et al. | |
| 8,030,798 B2 | 10/2011 | Seligman | |
| 8,140,152 B2 | 3/2012 | John et al. | |
| 8,165,678 B2 * | 4/2012 | Forsberg ............ | A61N 1/3787 607/33 |
| 8,412,334 B2 | 4/2013 | Whitehurst et al. | |
| 8,504,163 B1 | 8/2013 | Meadows | |
| 8,509,876 B2 | 8/2013 | Karmarkar | |
| 8,538,545 B2 | 9/2013 | Meskens | |
| 8,543,212 B2 | 9/2013 | Merfeld et al. | |
| 8,634,909 B2 | 1/2014 | Zimmerling et al. | |
| 8,639,344 B2 | 1/2014 | Greenberg et al. | |
| 8,639,391 B1 | 1/2014 | Alberth et al. | |
| 8,649,880 B1 | 2/2014 | Parker | |
| 8,718,779 B2 | 5/2014 | Whitehurst et al. | |
| 8,774,924 B2 | 7/2014 | Weiner | |
| 8,958,880 B2 | 2/2015 | De Giorgio | |
| 8,972,015 B2 | 3/2015 | Stack et al. | |
| 9,020,589 B2 | 4/2015 | Torgerson | |
| 9,095,699 B2 | 8/2015 | Rosenberg et al. | |
| 9,101,732 B2 | 8/2015 | Dadd et al. | |
| 9,421,387 B2 | 8/2016 | Hazard et al. | |
| 9,498,635 B2 * | 11/2016 | Dellamano .......... | A61N 1/3787 |
| 9,539,432 B2 * | 1/2017 | Dellamano .......... | A61N 1/3787 |
| 2002/0032471 A1 | 3/2002 | Loftin et al. | |
| 2002/0116042 A1 | 8/2002 | Boling | |
| 2005/0027192 A1 | 2/2005 | Govari et al. | |
| 2005/0030774 A1 | 2/2005 | Vazquez Carazo | |
| 2005/0075696 A1 | 4/2005 | Forsberg et al. | |
| 2005/0102006 A1 | 5/2005 | Whitehurst et al. | |
| 2005/0182470 A1 | 8/2005 | Cross | |
| 2005/0209667 A1 | 9/2005 | Erickson et al. | |
| 2005/0288741 A1 | 12/2005 | Hassler et al. | |
| 2006/0241717 A1 | 10/2006 | Whitehurst et al. | |
| 2006/0247754 A1 | 11/2006 | Greenberg et al. | |
| 2006/0293723 A1 | 12/2006 | Whitehurst et al. | |
| 2007/0073357 A1 | 3/2007 | Rooney et al. | |
| 2007/0112404 A1 | 5/2007 | Mann et al. | |
| 2007/0203545 A1 | 8/2007 | Stone et al. | |
| 2008/0039916 A1 | 2/2008 | Colliou et al. | |
| 2008/0183253 A1 | 7/2008 | Bly | |
| 2008/0269716 A1 | 10/2008 | Bonde | |
| 2008/0300657 A1 | 12/2008 | Stultz | |
| 2009/0018619 A1 | 1/2009 | Skelton et al. | |
| 2009/0058635 A1 * | 3/2009 | LaLonde ............ | A61N 1/37282 340/539.11 |
| 2009/0209945 A1 | 8/2009 | Lobl et al. | |
| 2009/0210028 A1 | 8/2009 | Rigaux | |
| 2009/0216324 A1 | 8/2009 | Leigh et al. | |
| 2009/0312769 A1 | 12/2009 | Dadd | |
| 2010/0110741 A1 | 5/2010 | Lin et al. | |
| 2010/0114249 A1 | 5/2010 | Wahlstrand et al. | |
| 2010/0161004 A1 | 6/2010 | Najafi | |
| 2010/0274313 A1 | 10/2010 | Boling et al. | |
| 2010/0331922 A1 | 12/2010 | Digiore et al. | |
| 2011/0009925 A1 | 1/2011 | Leigh et al. | |
| 2011/0046699 A1 | 2/2011 | Mazanec | |
| 2011/0093047 A1 | 4/2011 | Davis et al. | |
| 2011/0112603 A1 | 5/2011 | Degiorgio et al. | |
| 2011/0172736 A1 | 7/2011 | Gefen et al. | |
| 2011/0190849 A1 | 8/2011 | Faltys et al. | |
| 2012/0078327 A1 | 3/2012 | Sloan et al. | |
| 2012/0078337 A1 | 3/2012 | Darley et al. | |
| 2012/0078338 A1 | 3/2012 | Darley et al. | |
| 2012/0112556 A1 | 5/2012 | Forsell | |
| 2012/0215218 A1 | 8/2012 | Lipani | |
| 2012/0274270 A1 | 11/2012 | Dinsmoor | |
| 2012/0277823 A1 | 11/2012 | Gerber et al. | |
| 2013/0057364 A1 | 3/2013 | Kesler et al. | |
| 2013/0085542 A1 | 4/2013 | Mashiach | |
| 2013/0085561 A1 | 4/2013 | Mashiach | |
| 2013/0131754 A1 * | 5/2013 | Sarvazyan .......... | A61N 1/3606 607/45 |
| 2013/0165996 A1 | 6/2013 | Meadows et al. | |
| 2013/0197613 A1 | 8/2013 | Kelly | |
| 2013/0198531 A1 | 8/2013 | Hansen | |
| 2013/0238067 A1 | 9/2013 | Baudino | |
| 2013/0282086 A1 | 10/2013 | McDonald et al. | |
| 2013/0289662 A1 | 10/2013 | Olson et al. | |
| 2013/0333918 A1 | 12/2013 | Lotfi | |

(56) References Cited

U.S. PATENT DOCUMENTS

| | | |
|---|---|---|
| 2014/0012349 A1 | 1/2014 | Zimmerling et al. |
| 2014/0070808 A1 | 3/2014 | Reykowski et al. |
| 2014/0142669 A1 | 5/2014 | Cook et al. |
| 2014/0148883 A1 | 5/2014 | Stack et al. |
| 2014/0222125 A1 | 8/2014 | Glenn et al. |
| 2014/0292327 A1 | 10/2014 | Griswold et al. |
| 2014/0303685 A1 | 10/2014 | Rosenberg et al. |
| 2014/0343626 A1 | 11/2014 | Thenuwara et al. |
| 2015/0025613 A1 | 1/2015 | Nyberg, II et al. |
| 2015/0087892 A1 | 3/2015 | Tourrel et al. |
| 2015/0157862 A1 | 6/2015 | Greenberg et al. |
| 2015/0280444 A1 | 10/2015 | Smith |
| 2015/0303806 A1 | 10/2015 | Madsen et al. |
| 2016/0008602 A1 | 1/2016 | Perryman et al. |
| 2016/0036244 A1 | 2/2016 | Griffith |
| 2016/0114174 A1 | 4/2016 | Colvin et al. |
| 2016/0242685 A1 | 8/2016 | De Hennis |

OTHER PUBLICATIONS

Weiner RL and Reed KL Peripheral neurostimulation for control of intractable occipital neuralgia. Neuromodulation: journal of the International Neuromodulation Society. 1999; 2: 217-21, Jan. 1, 1999.

Goadsby PJ and Spencer T. Current practice and future directions in the prevention and acute management of migraine. The Lancet Neurology. 2010; 9: 285-98, Jan. 1, 2010.

Dodick DW. Occipital nerve stimulation for chronic cluster headache. Advanced Studies in Medicine. 2003; 3: S569- S71, Jan. 1, 2003.

Saper JR, Dodick DW, Silberstein SD, McCarville S, Sun M and Goadsby PJ. Occipital nerve stimulation for the treatment of intractable chronic migraine headache: ONSTIM feasibility study. Cephalalgia: an international journal of headache. 2011; 31:271-85, Jan. 1, 2011.

Silberstein S, Dodick DW, Reed KL, et al. Safety and efficacy of peripheral nerve stimulation of the occiptial nerves for the management of chronic migraine. Cephalalgia: an international journal of headache. 2012, Jan. 1, 2012.

Slavin KV, Colpan ME, Munawar N, Wess C and Nersesyan H. Trigeminal and occipital peripheral nerve stimulation for craniofacial pain: a single-institution experience and review of the literature. Neurosurgical focus. 2006; 21: E5, Jan. 1, 2006.

Schwedt TJ, Dodick DW, Hentz J, Trentman TL and Zimmerman RS. Occipital nerve stimulation for chronic headache—long-term safety and efficacy. Cephalalgia: an international journal of headache. 2007; 27: 153-7, Jan. 1, 2007.

Reed KL, Black SB, Banta CJ, 2nd and Will KR. Combined occipital and supraorbital neurostimulation for the treatment of chronic migraine headaches: initial experience. Cephalalgia: an international journal of headache. 2010; 30: 260-71, Jan. 1, 2010.

Reed KL, Will KR, Chapman J and Richter E. Combined occipital and supraorbital neurostimulation for chronic migraine headaches [abst]. 15th Congress of the International Headache Society. Berlin, Germany: Cephalalgia, 2011, p. 98-9, Jan. 1, 2011.

Lipton RB, Goadsby PJ, Cady RK, et al. PRISM study: occipital nerve stimulation for treatment-refractory migraine (p abs). Cephalalgia: an international journal of headache. 2009; 29: 30, Jan. 1, 2009.

Reed KL. Peripheral neuromodulation and headaches: history, clinical approach, and considerations on underlying mechanisms. Current pain and headache reports. 2012; 17: 25-35, Jan. 1, 2012.

Mueller OM, Gaul C, Katsarava Z, Diener HC, Sure U and Gasser T. Occipital nerve stimulation for the treatment of chronic cluster headache—lessons learned from 18 months experience. Central European neurosurgery. 2011; 72: 84-9. Jan. 1, 2011.

Medtronic, Inc. Peripheral Nerve Stimulation: Percutaneous Lead Implantation Guide for Treatment of Chronic Pain, Jan. 1, 1999.

Redl, Richard. Fundamental Considerations for Very High Frequency Power Conversion. Electronic Feasibility Investigations. 2008, Jan. 1, 2008.

Sreelakshmi V, Menon R, Sheela G. An RF-FC Converter with Wide Dynamic Range Input Matching for Power Recovery Applications. International Journal of Advanced Research in Electrical, Electronics and Instrumentation Engineering. Dec. 2014, Dec. 1, 2014.

Rooij M. eGaN FET based Wireless Energy Transfer Topology Performance Comparisons. 2015, Jan. 1, 2015.

PCT: International Search Report and Written Opinion of PCT/US2014/51235; dated Feb. 19, 2015; 24 pages, dated Feb. 19, 2015.

European Patent Office, Extended European Search Report, No. EP 14 85 5587, dated May 24, 2017; Lins, Stephanie; 7 pages.

* cited by examiner

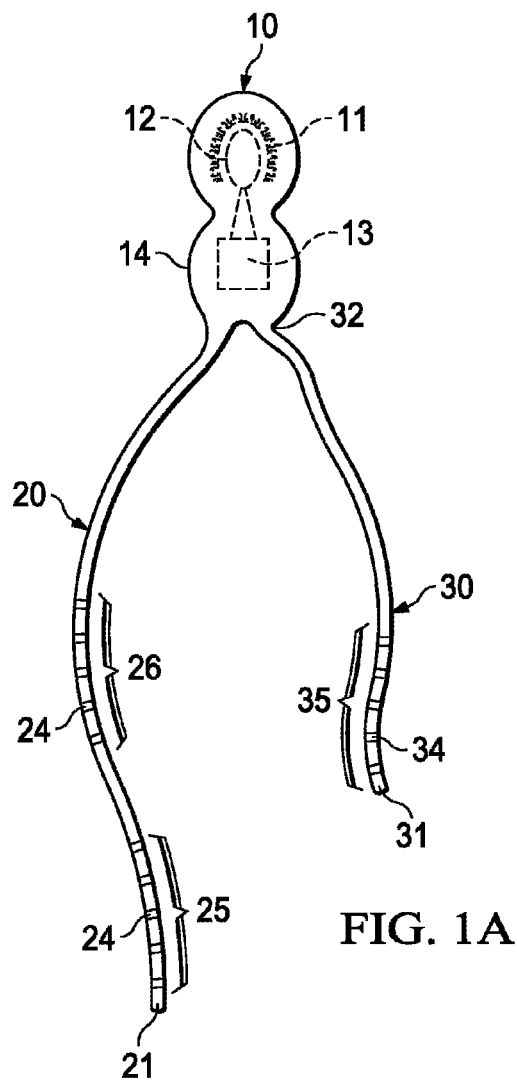
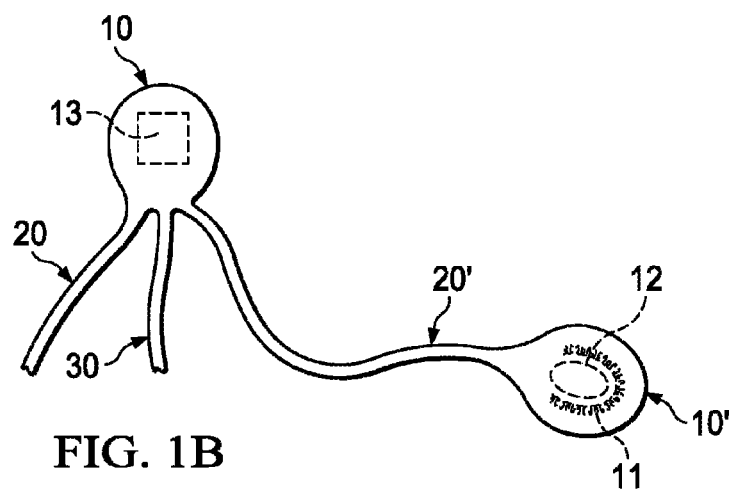
FIG. 1A
FIG. 1B

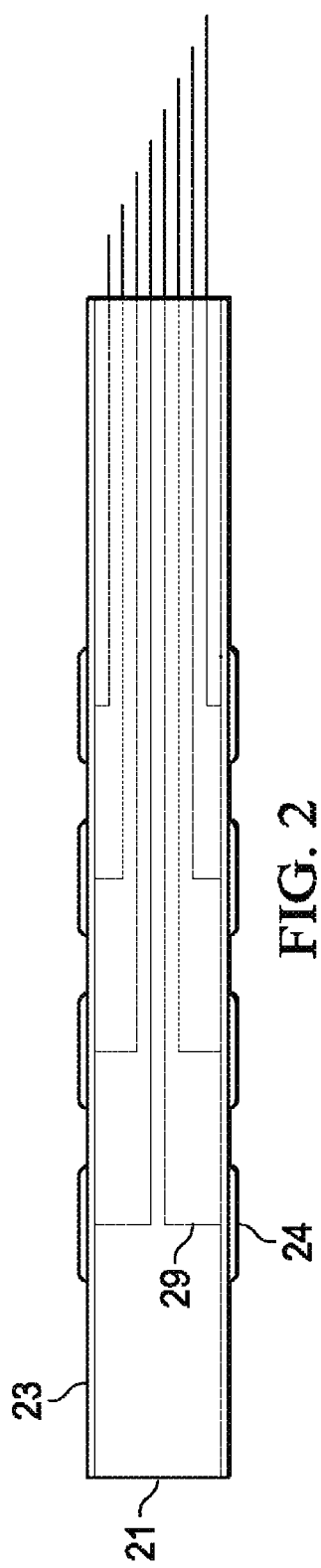

IMPLANTABLE HEAD LOCATED RADIOFREQUENCY COUPLED NEUROSTIMULATION SYSTEM FOR HEAD PAIN

CROSS-REFERENCE TO RELATED APPLICATIONS

This application is a Continuation of U.S. patent application Ser. No. 14/990,678, filed Jan. 7, 2016, entitled IMPLANTABLE HEAD LOCATED RADIOFREQUENCY COUPLED NEUROSTIMULATION SYSTEM FOR HEAD PAIN, which issued as U.S. Pat. No. 9,539,432 on Jan. 10, 2017, the specification of which is incorporated by reference herein in its entirety. U.S. patent application Ser. No. 14/990,678 is a Continuation of U.S. patent application Ser. No. 14/989,674, filed Jan. 6, 2016, entitled IMPLANTABLE HEAD LOCATED RADIOFREQUENCY COUPLED NEUROSTIMULATION SYSTEM FOR HEAD PAIN, which issued as U.S. Pat. No. 9,498,635 on Nov. 22, 2016, the specification of which is incorporated by reference herein in its entirety. U.S. patent application Ser. No. 14/989,674 is a Continuation-in-Part of U.S. patent application Ser. No. 14/879,943, filed Oct. 9, 2015, entitled SURGICAL METHOD FOR IMPLANTABLE HEAD MOUNTED NEUROSTIMULATION SYSTEM FOR HEAD PAIN, the specification of which is incorporated by reference herein in its entirety. U.S. patent application Ser. No. 14/879,943 is a Continuation-in-Part of U.S. patent application Ser. No. 14/717,912, filed May 20, 2015, entitled IMPLANTABLE HEAD MOUNTED NEUROSTIMULATION SYSTEM FOR HEAD PAIN, the specification of which is incorporated by reference herein in its entirety. U.S. patent application Ser. No. 14/717,912 is a Continuation of U.S. patent application Ser. No. 14/460,139, filed Aug. 14, 2014, entitled IMPLANTABLE HEAD MOUNTED NEUROSTIMULATION SYSTEM FOR HEAD PAIN, now issued as U.S. Pat. No. 9,042,991, the specification of which is incorporated by reference herein in its entirety. U.S. patent application Ser. No. 14/460,139 claims benefit of U.S. Provisional Application No. 61/894,795, filed Oct. 23, 2013, entitled IMPLANTABLE HEAD MOUNTED NEUROSTIMULATION SYSTEM FOR HEAD PAIN, the specification of which is incorporated by reference herein in its entirety. U.S. patent application Ser. Nos. 14/990,678, 14/989,674, 14/789,943, 14/717,912, 14/460,139, and 61/894,795, and U.S. Pat. Nos. 9,539,432, 9,498,635, and 9,042,991 are incorporated by reference herein in their entirety.

TECHNICAL FIELD

The present disclosure relates to implantable neurostimulation systems and methods of treating migraine headaches and other forms of chronic head pain.

BACKGROUND OF THE INVENTION

Neurostimulation systems comprising implantable neurostimulation leads are used to treat chronic pain. Conventional implantable peripheral neurostimulation leads are designed for placement in the spinal canal as part of a spinal cord stimulation system, and for the therapeutic purpose of treating various forms of chronic back and extremity pain. Implantable neurostimulation systems may either be powered by an internal battery or by an external power source coupled to the internal unit by a radiofrequency interface.

SUMMARY OF THE INVENTION

In various implementations, an implantable head-mounted, radiofrequency-coupled, unibody peripheral nerve stimulation system may be configured for implantation of substantially all electronics, except for an on-site battery, at or near the implanted electrodes on the skull. The system may include an implantable pulse generator (IPG) from which two neurostimulating leads may extend to a length sufficient to provide therapeutic neurostimulation unilaterally over the frontal, parietal and occipital regions of the hemicranium. The IPG may have a component, or extension, containing an internal radiofrequency receiver, the purpose of which is to couple to an external power source and control unit. The system may be operable to provide medically acceptable therapeutic neurostimulation to multiple regions of the head, including the frontal, parietal and occipital regions of the hemicranium substantially simultaneously.

Each of the leads may include an extended lead body; a plurality of surface metal electrodes disposed along the lead body, which may be divided into two or more electrode arrays; and a plurality of internal electrically conducting metal wires running along at least a portion of the length of the lead body and individually connecting an internal circuit of the IPG to individual surface metal electrodes. The extended lead body may comprise a medical grade plastic.

Implementations may include one or more of the following features. The IPG may be of proper aspect ratio with respect to the specific site of intended implantation in the head, such as an area posterior to and/or superior to the ear. The IPG may include an antenna coil and an application specific integrated circuit (ASIC). The IPG may be configured for functionally connecting with an external radiofrequency unit.

Implementations may include one or more of the following features. A neurostimulating lead may not include a central channel for a stylet. A neurostimulating lead may have a smaller diameter than conventional leads.

Implementations may include one or more of the following features. The system may include the disposition of a sufficient plurality of surface electrodes over a sufficient linear distance along the neurostimulating leads to enable medically adequate therapeutic stimulation across multiple regions of the head, including the frontal, parietal, and occipital region of the hemicranium substantially simultaneously. The extended array of surface electrodes may be divided into two or more discrete terminal surface electrode arrays. The linear layout of the multiple surface electrode arrays may include at least one array positioned over the frontal region, at least one array positioned over the parietal region, and at least one array positioned over the occipital region. Specific intra-array design features may include variations in the specific number of electrodes allotted to each group; the shape of the electrodes, e.g., whether the electrodes are cylindrical or flattened; the width of each electrode within each array, and the linear distance intervals of separation of the electrodes within each array.

Various implementations may include a plurality of connection ports that can be connected with a plurality of leads and thus allow for attaching additional leads.

The external radiofrequency unit may be operable to perform various functions including recharging the rechargeable battery, diagnostically evaluating the IPG, and programming the IPG.

In various implementations, methods of treating chronic pain may include methods of treating chronic head and/or face pain pain of multiple etiologies, including migraine headaches; and other primary headaches, including cluster headaches, hemicrania continua headaches, tension type headaches, chronic daily headaches, transformed migraine headaches; further including secondary headaches, such as cervicogenic headaches and other secondary musculoskeletal headaches.

In various implementations, methods of treating chronic pain may include methods of treating head and/or face pain of multiple etiologies, including neuropathic head and/or face pain, nociceptive head and/or face pain, and/or sympathetic related head and/or face pain.

In various implementations, methods of treating chronic pain may include methods of treating head and/or face pain of multiple etiologies, including greater occipital neuralgia, as well as the other various occipital neuralgias, supraorbital neuralgia, auroiculotemporal neuralgia, infraorbital neuralgia, and other trigeminal neuralgias, and other head and face neuralgias.

The details of one or more implementations are set forth in the accompanying drawings and the description below. Other features, objects, and advantages of the implementations will be apparent from the description and drawings.

In certain aspects, a method is provided for controlling power delivery from an external power transfer system (EPTS) to at least one implantable neurostimulation system (INS). In some embodiments, the method includes driving a first transmit coil within the EPTS with a resonant current having a peak magnitude, using a transmit coil driver circuit within the EPTS. The method also includes receiving, using a receive coil within a first INS tuned to the resonant frequency of the first transmit coil, power transferred from the first transmit coil, and coupling the received power to a regulator circuit within the first INS which is configured to provide an electrode current to an electrode driver circuit within the first INS for a plurality of electrodes therewithin. The method further includes monitoring the regulator circuit within the first INS to determine whether the received power coupled thereto is sufficient to achieve current regulation of the regulator circuit within the first INS. The method further includes communicating a message to the EPTS using a back telemetry transmit circuit within the first INS, the message requesting a change in power transfer from the EPTS based upon the regulator circuit determination, and receiving, using a back telemetry receive circuit within the EPTS, the message communicated by the first INS. The method also includes adjusting the transmit coil driver circuit within the EPTS to change the peak magnitude of the resonant current, corresponding to the requested change in power transfer.

In some embodiments, the method also includes a message which includes a request to increase power transfer from the EPTS if the regulator circuit within the first INS is not achieving current regulation, and includes a corresponding change in the peak magnitude of the resonant current which includes an increase in peak magnitude. Some embodiments will additionally include adjusting the transmit coil driver circuit within the EPTS to decrease the peak magnitude of the resonant current, if no message requesting an increase in power transfer from the EPTS has been received from the first INS for at least a certain period of time.

In some embodiments, the message includes a request to decrease power transfer from the EPTS if the regulator circuit within the first INS is achieving current regulation, and the corresponding change in the peak magnitude of the resonant current includes a decrease in the peak magnitude.

In some embodiments, the monitoring the regulator circuit within the first INS is performed under control of a state machine circuit within the first INS, and the communicating a first message to the EPTS is performed under control of an instruction-based processor within the first INS. In some embodiments, the state machine circuit within the first INS is configured to wake-up the instruction-based processor within the first INS, in the event the instruction-based processor is not already awake, to communicate the first message.

In some embodiments, monitoring the regulator circuit within the first INS includes comparing the electrode current provided by the regulator circuit within the first INS against a prescribed electrode current for the electrode driver circuit within the first INS corresponding to a stimulation configuration programmed therein, and determining that the regulator circuit is achieving current regulation if the electrode current is greater than or equal to the prescribed electrode current. In some embodiments, comparing the electrode current against the prescribed electrode current is performed under control of a state machine circuit within the first INS.

In some embodiments, coupling the received power to a regulator circuit within the first INS includes rectifying a current induced on the receive coil, to generate a rectified voltage on an input node of the regulator circuit within the first INS. In some embodiments, monitoring the regulator circuit within the first INS includes monitoring an input voltage and an output voltage of the regulator circuit within the first INS, and determining that the regulator circuit is achieving current regulation if a voltage differential between the input voltage and the output voltage exceeds a predetermined value.

In some embodiments, the method further includes de-tuning the receive coil within the first INS, using a de-tuning circuit within the first INS, to substantially inhibit power transfer from the EPTS to the first INS.

In some embodiments, the regulator circuit within the first INS is further configured to provide a charging current to a charge storage device within the first INS. In certain of these embodiments, monitoring the regulator circuit within the first INS includes comparing the electrode current provided by the regulator circuit within the first INS against a prescribed electrode current for the electrode driver circuit within the first INS corresponding to a stimulation configuration programmed therein, comparing the charging current provided by the regulator circuit within the first INS against a predetermined charging current, and determining that the regulator circuit is achieving current regulation if the electrode current is greater than or equal to the prescribed electrode current, and the charging current is greater than or equal to the predetermined charging current. In certain of these embodiments, the charge storage device is a supercapacitor.

In some embodiments, the method further includes driving, using the transmit coil driver circuit within the EPTS, the resonant current through a second transmit coil coupled in series with the first transmit coil within the EPTS; receiving, using a receive coil within a second INS tuned to the resonant frequency of the second transmit coil, power transferred from the second transmit coil; coupling the received power within the second INS to a regulator circuit within the second INS which is configured to provide an electrode current to an electrode driver circuit within the second INS for a plurality of electrodes therewithin; monitoring the regulator circuit within the second INS to determine whether the received power coupled thereto is sufficient to achieve current regulation of the regulator circuit within the second INS; communicating a message from the second INS to the EPTS using a back telemetry transmit circuit within the second INS, said message requesting a change in power transfer from the EPTS based upon said regulator circuit determination for the second INS; receiving, using the back telemetry receive circuit within the EPTS, the third message communicated by the second INS; and adjusting the transmit coil driver circuit within the EPTS to change the peak magnitude of the resonant current, corresponding to the requested change in power transfer conveyed in the message communicated by the second INS.

In some embodiments, the method further includes adjusting the transmit coil driver circuit within the EPTS to decrease the peak magnitude of the resonant current, if no message requesting an increase in power transfer from the EPTS has been received from the first INS, and no message requesting an increase in power transfer from the EPTS has been received from the second INS, for at least a certain period of time.

In some embodiments, the method further includes de-tuning the receive coil within the second INS, using a de-tuning circuit within the second INS, to substantially inhibit power transfer from the EPTS to the second INS without inhibiting power transfer from the EPTS to the first INS.

In some embodiments, the first and second INSs are head-located beneath a dermis layer, or skin, of a patient.

In another embodiment, a system is provided for controlling power delivery from an external power transfer system (EPTS) to at least one implantable neurostimulation system (INS). In some embodiments the system includes an EPTS disposed outside a body, and at least one INS disposed beneath a dermis layer of the body. The EPTS includes a group of one or more transmit coils disposed in series, each corresponding to a respective INS; a transmit coil driver circuit operable to drive the group of one or more transmit coils with a resonant current having a peak magnitude; and a back telemetry circuit operable to receive a message communicated by an INS. Each of said at least one INS respectively includes a receive coil tuned to the resonant frequency of the corresponding transmit coil and operable to receive power transferred therefrom when in proximity thereto; a regulator circuit having an input to which the received power is coupled, and operable to provide on an output thereof an electrode current to an electrode driver circuit for a plurality of electrodes; a monitoring circuit operable to determine whether the received power is sufficient to achieve current regulation of the regulator circuit; and a back telemetry circuit operable to communicate a message to the EPTS. Each respective INS is operable to communicate a respective message requesting a change in power transfer from the EPTS based upon the respective regulator circuit determination; and the EPTS is operable to adjust the transmit coil driver circuit to change the peak magnitude of the resonant current, based upon respective messages from one or more respective INS.

In some embodiments, each respective message includes a request to increase power transfer from the EPTS if the respective regulator circuit is not achieving current regulation, and the EPTS is further operable to adjust the transmit coil driver circuit to increase the peak magnitude of the resonant circuit, in response to receiving a respective message from any respective INS requesting an increase in power transfer.

In some embodiments, the EPTS is further operable to adjust the transmit coil driver circuit to decrease the peak magnitude of the resonant current, if no respective message requesting an increase in power transfer from the EPTS has been communicated by any respective INS for at least a certain period of time.

In some embodiments, each respective message includes a request to decrease power transfer from the EPTS if the respective regulator circuit is achieving current regulation, and the EPTS is further operable to adjust the transmit coil driver circuit to decrease the peak magnitude of the resonant current, in response to receiving a respective message from every respective INS requesting a decrease in power transfer.

In some embodiments, the respective monitoring circuit within each respective INS is operable to compare the respective electrode current provided by the respective regulator circuit against a respective prescribed electrode current for the respective electrode driver circuit corresponding to a stimulation configuration programmed therein, and determine that the respective regulator circuit is achieving current regulation if the respective electrode current is greater than or equal to the respective prescribed electrode current.

In some embodiments, each respective INS further includes a respective resonant rectifier circuit having an input coupled to the respective receive coil, and having an output coupled to the input of the respective regulator circuit. The respective resonant rectifier circuit is operable to generate on its respective output a rectified voltage. In some embodiments each respective INS may further include a respective de-tuning circuit coupled to the respective receive coil, being operable to de-tune the respective receive coil to inhibit power transfer from the EPTS to the respective INS.

In some embodiments, each respective INS further includes a respective charge storage device, and each respective regulator circuit is further operable to provide on a second output thereof a charging current to the respective charge storage device. In some embodiments each respective charge storage device may be a supercapacitor.

In some embodiments, each respective INS is head-located beneath the dermis layer of a patient.

In another embodiment, a neurostimulation system is provided including a power unit, which includes a variable power generator, a controller to control the output power level of the variable power generator, a power coupler for coupling power over a dermis layer, and a power source telemetry system for receiving information across a dermis layer for input to the controller; and an implantable neurostimulator including at least one neurostimulator lead with at least one array of stimulation electrodes, an electrode driver for driving the electrodes with a desired power, a power level detector for detecting the output power of the electrode driver, a neurostimulator power coupler for coupling power from over a dermis layer, a neurostimulator telemetry system for transmitting information across the dermis layer to the power source telemetry system, and a processor for determining the amount of power required from the power source as a power demand based on the output of the power level detector and transmitting a request for a desired power level to the controller via the telemetry system in the power source; wherein the controller increases or decreases the power level delivered to the implantable neurostimulator as a function of determined power demand by the processor.

In some embodiments, the power unit and neurostimulator power couplers each include at least one coil. In some of these embodiments, the variable power generator generates alternating current power. Some embodiments further include a controller which varies the power generated by varying a voltage of the variable power generator. In some embodiments, the implantable neurostimulator further includes a charge storage device. In some embodiments, the power unit power coupler is inductively coupled to the neurostimulator power coupler. In some embodiments, the neurostimulator and the power unit telemetry system each communicate information across the dermis layer through the respective power unit and neurostimulator power couplers.

In another embodiment, a system is provided for driving an implantable neurostimulator lead having a plurality of electrodes disposed in at least one array, the system including an implantable pulse generator (IPG), which includes an electrode driver for driving the electrodes, a load system for determining load requirements of the IPG, an IPG power coupler for receiving power across a dermis layer for interface of the power with the electrode driver, and an IPG communication system for transmitting the load determined requirement of the IPG across the dermis layer. In this embodiment, the system also includes an external unit, which includes an external variable power generator, an external power coupler for coupling power across the dermis layer to the IPG power coupler, an external communication system for receiving from the IPG communication system the determined load requirements, and a controller for varying the power level of the variable generator as a function of the received determined load requirements of the IPG.

In some embodiments, the electrode driver drives the electrodes with a constant current. In some embodiments, the load system further includes a detector for detecting power delivered to the electrodes and a processor for determining the necessary power from the external unit required by the electrode driver as the determined load requirements of the IPG. In some embodiments, the electrode driver delivers a predetermined constant current. In some of these embodiments, the predetermined load requirement includes at least enough power from the external unit to provide the predetermined constant current from the electrode driver. In some embodiments, the IPG also includes a charge storage device. In some embodiments, the IPG is head-located beneath the dermis layer of a patient. In some embodiments, the IPG communication system and the external communication system each include at least one coil.

In another embodiment, the system is for driving a plurality of implantable neurostimulator leads, each lead having an associated plurality of electrodes disposed in at least on array on the lead. The system includes at least two implantable pulse generators (IPGs), with each IPG including an electrode driver for driving the electrodes associated with the IPG, a load system for determining load requirements of the IPG, an IPG power coupler for receiving power across a dermis layer for interface of the power with the electrode driver of the IPG, and an IPG communication system for transmitting the load determined requirement of the IPG across the dermis layer. The system also includes an external unit, which includes an external variable power generator, and external power coupler for coupling power across the dermis layer to the IPG power couplers, and external communication system for receiving from the IPG communication systems the respective determined load requirements, and a controller for varying the power level of the variable power generator as a function of the received determined load requirements of the IPG with the greatest load requirement.

In some embodiments, the communication systems of the IPGs are operable to transmit load requirements to the external communication system independently of the communication systems of the other IPGs. In some embodiments the IPG communication systems transmit the load determined requirements to the external unit communication system inductively. In some embodiments, the IPG power couplers are for receiving levels of power across a dermis layer that are independent of the levels of power received by the power couplers of the other IPGs. In some embodiments, at least one of the IPGs also includes a charge storage device.

The foregoing is a summary and thus contains, by necessity, simplifications, generalizations and omissions of detail. The details of various implementations are set forth in the accompanying drawings and the description below. Consequently, those skilled in the art will appreciate that the foregoing summary is illustrative only and is not intended to be in any way limiting of the invention. It is only the claims, including all equivalents, in this or any non-provisional application claiming priority to this application, that are intended to define the scope of the invention(s) supported by this application.

BRIEF DESCRIPTION OF THE DRAWINGS

For a more complete understanding, reference is now made to the following description taken in conjunction with the accompanying Drawings in which:

FIG. 1A illustrates an embodiment of the IPG 10 and the various configurations of the lead;

FIG. 1B illustrates an embodiment of the IPG 10 and the various configurations of the lead;

FIG. 2 depicts a side view of a Frontal Electrode Array (FEA) with Internal Wires. The FEA is disposed over the distal portion (such as 8-10 cm) of the FPL, which anatomically places it over the frontal region, and specifically over the supraorbital nerve and other adjacent nerves of the region. In general the layout, disposition and connections of the Internal Wires and Surface Electrodes disposed over the Parietal Electrode Array (PEA) and the Occipital Electrode Array (OEA) are the same as that depicted for the FEA;

FIG. 18, which includes

DETAILED DESCRIPTION

A. Introduction

Figure 1:
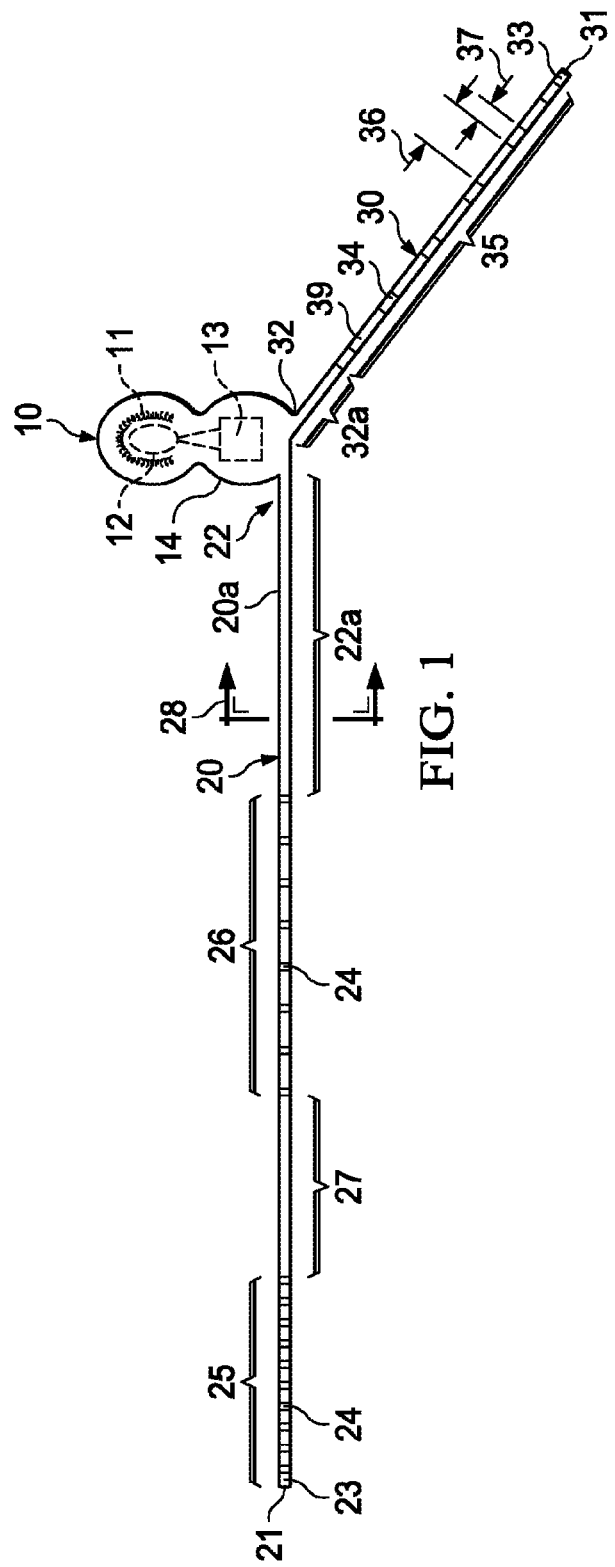
FIG. 1 depicts a side view of a full Head-Mounted, Unibody Radiofrequency-Coupled Neurostimulator System for migraine and other head pain. The system features an implantable pulse generator (IPG) from which two neurostimulating leads extend—a Frontal-Parietal Lead (FPL) and an Occipital Lead (OL). Each lead includes a plurality of electrodes in a distribution and over a length to allow full unilateral coverage of the frontal, parietal, and occipital portions of the head. The IPG contains all electronics, including an Application Specific Integrated Circuit (ASIC) and an RF Receiver Coil that is capable of an RF couple to an External Power Source and Programming Unit.

Referring now to the drawings, wherein like reference numbers are used herein to designate like elements throughout, the various views and embodiments of an implantable neurostimulation lead for head pain are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

The present disclosure provides for a fully head-located, radiofrequency-coupled, implantable peripheral neurostimulation system that is specifically designed for the treatment of chronic head pain. It incorporates multiple unique elements and features that take into account the unique anatomic, physiologic, and other related challenges of treating head pain with implantable neurostimulation and, by doing so, greatly improves on therapeutic response, patient safety, medical risk, and medical costs, which combine to improve overall patient satisfaction.

Prior implantable peripheral neurostimulation systems and components, including leads and pulse generators, had been originally designed and developed specifically as spinal cord stimulator systems and for the specific therapeutic purpose of treating chronic back and extremity pain. Over the years, however, these spinal cord stimulators were ultimately adopted and adapted for use as implantable peripheral nerve stimulators for the treatment of migraine headaches and other forms of chronic head pain. However, they were so utilized with full recognition of the inherent risks and limitations due to the fact that they had been developed to only address, and accommodated to, the unique anatomic and physiologic features of the back and chronic back pain.

A number of problems have been recognized with respect to spinal cord stimulators for head pain as fundamentally due to design flaws associated with, and inherent to, the use of an implantable therapeutic device in an area of the body that it was not designed for.

The anatomy of the head and the pathophysiology of headaches and other forms of head pain are so significantly different from the anatomy of the spinal canal and pathophysiology of chronic back pain, that when spinal cord stimulators are utilized for cranial implants, the clinical problems associated with these differences manifest themselves. Importantly, these well-documented problems are clinically very significant and include issues of patient safety and satisfaction, the risk of an inadequate or suboptimal therapeutic response, issues with patient comfort and cosmetics, and a recognized increased risk of surgical complications and technical problems.

Prior implantable peripheral neurostimulation leads have been designed and developed specifically for placement in the spinal canal as part of a spinal cord stimulation system and for the specific therapeutic purpose of treating various forms of chronic back and extremity pain. The present disclosure provides an implantable peripheral neurostimulation lead that is designed for the implantation in the head for the treatment of chronic head pain. It incorporates multiple unique elements and features that take into account the unique anatomic, physiologic, and other related challenges of treating head pain with implantable neurostimulation and by doing so greatly improves on therapeutic response, patient safety, medical risk, medical costs, which combine to improve overall patient satisfaction.

Indeed, the anatomy of the head, and the pathophysiology of headaches and other forms of head pain that are unique to the head, are so significantly different from the anatomy of the spinal canal, and pathophysiology of chronic back pain that when these current leads are indeed utilized as cranial implants, then the clinical problems associated with these differences manifest themselves. Specifically, these include issues with inadequate therapeutic responses, issues with patient comfort and cosmetics, and also very significant issues with patient safety.

These medical risks stem from the design of conventional leads and the IPG. Conventional lead designs include a relatively large diameter, a cylindrical shape, (often) inadequate length, and the necessity of implanting the IPG in the torso and distant from the distal leads, and a number and disposition of the surface electrodes and active lead arrays that do not match the requirements. A cylindrical lead of relatively large diameter results in increased pressure on, and manifest tenting of, the overlying skin, particularly of the forehead. Because conventional leads are of inadequate length to extend from the head to the IPG implant site, commonly in the lower back, abdomen, or gluteal region, lead extensions are often employed, and there are attendant risks of infection, local discomfort, and cosmetic concerns.

With respect to prior leads: 1) There is only a single array of electrodes, with common lead options including 4, 8, or 16 electrodes disposed over that single array; 2) The array is relatively short with most leads having an array of from 5-12 cm in length; 3) Within this single array, the individual electrodes are disposed uniformly with constant, equal inter-electrode distances. This results in the need to implant multiple (often four or more) of the conventional leads to adequately cover the painful regions of the head.

There are several practical clinical outcomes that result from the use of prior leads for the treatment of chronic head pain. First, since they comprise a single, relatively short active array, the currently available leads provide therapeutic stimulation to only a single region of the head; that is, they can provide stimulation to only the frontal region, or a portion of the parietal region, or a portion of the occipital region. Therefore, if a patient has pain that extends over multiple regions, then multiple separate lead implants are required—basically one lead implant is required for each unilateral region. A great majority of patients with chronic headaches experience holocephalic pain; that is they experience pain over the frontal and parietal and occipital regions bilaterally. Therefore, commonly these patients will need 4 to 7 leads implanted to achieve adequate therapeutic results (2 or 3 leads on each side).

Second, the need for multiple leads includes considerable added expense, and more importantly, added medical risk associated with adverse events attendant to the multiple surgical procedures. Such adverse events include an increased risk of infection, bleeding, and technical issues with the leads, e.g., lead fracture, lead migration, and local irritation.

Third, as the clinical database discloses, the inter-electrode spacing may be of central therapeutic significance. That is, for example, whereas commonly pain over the occipital region is consistently effectively treated by quadripolar leads (leads with four evenly spaced electrodes) that have the electrodes relatively widely spaced apart (approximately a cm or more apart), clinically it is often found that electrodes configurations that are more narrowly spaced may be more effective over the supraorbital nerve and regions. Thus, a quadripolar lead that has the electrodes only 1-2 mm apart may be more effective in this region, as it allows for more precise control of the delivered electrical pulse wave delivery.

When an IPG implant for spinal cord stimulation systems is employed as a peripheral nerve stimulator for head pain, several outcomes result. First, the IPG is implanted at a considerable anatomic distance from the cranial lead implants. Indeed, the leads must pass from their distal cranial implant positions across the cervical region and upper back to the IPG implant location, which are most commonly in the lower back, lower abdomen, or gluteal region. The leads must cross multiple anatomic motion segments, including the neck and upper back and/or chest at a minimum, and commonly include the mid back, lower back and waist segments, as well. The simple motions of normal daily life produce adverse tension and torque forces on the leads across these motion segments, which in turn increases the risk of various outcomes including lead migration and/or lead fracture. In addition, the relatively large size of a spinal cord stimulator IPG contributes to local discomfort, cosmetic concerns, and increased risk of infection that may become larger and harder to treat in proportion to the size of the IPG pocket.

The present disclosure is directed to an implantable neurostimulation system that includes an IPG from which two neurostimulating leads extend to a length sufficient to allow for therapeutic neurostimulation unilaterally over the frontal, parietal and occipital regions of the head.

The present disclosure addresses and effectively solves problems attendant to publically available leads. The most important of these is the fact that currently available leads can only adequately stimulate a single region of the head due to design element flaws associated with terminal surface electrode number and disposition. The disclosure additionally addresses and solves other problems inherent with the currently available leads, including problems with cosmetics and patient comfort, particularly over the frontal regions, due the uncomfortable pressure placed on the skin of the forehead, due the cylindrical shape and relatively large diameter of the distal portion of the lead. Finally, the lead of the present disclosure solves the currently available leads' problem of inadequate lead length to reach a gluteal location of the implantable pulse generator, which therefore necessitates the additional risk and expense of further surgery to implant lead extensions.

In one aspect, the implantable, head-mounted, neurostimulation system for head pain is operable for subcutaneous implantation in the head, and to provide neurostimulation therapy for chronic head pain, including chronic head pain caused by migraine and other headaches, as well as chronic head pain due other etiologies. The peripheral neurostimulator system disclosed herein takes into account unique anatomic features of the human head, as well as the unique, or singular, features of the various pathologies that give rise to head pain, including migraine and other headaches, as well as other forms of chronic head pain. To date, all commercially available leads and systems that have been clinically utilized for implantation as a peripheral neurostimulator lead were actually originally designed specifically for placement in the epidural space, as part of a spinal cord stimulation system, for the therapeutic purpose of treating chronic back and/or extremity pain. Thus, there are currently no commercially available leads or full system that have designs in the public domain, that have been designed and developed for use in the head and for head pain.

In another aspect, the implantable, head-mounted, neurostimulation system for head pain comprises multiple design features, including disposition of a sufficient plurality of surface electrodes over a sufficient linear distance along the distal lead, such as will result in a lead that, as a single lead, is capable of providing medically adequate therapeutic stimulation over the entire hemicranium; that is, over the frontal, parietal, and occipital region stimulation. Currently available systems, which were designed specifically for epidural placement for chronic back pain, are capable of only providing stimulation over a single region; that is, over either the frontal region alone, or the parietal region alone, or the occipital region alone.

In yet another aspect, the implantable peripheral neurostimulation system for head pain comprises multiple design features, including the physical grouping of the extended array of surface electrodes into three or more discrete terminal surface electrode arrays. The linear layout of these two or more (preferably three or more) surface electrodes arrays is designed such that following implantation there would be at least one array positioned over the frontal region, at least one array positioned over the parietal region, and at least one array positioned over the occipital region. This feature further improves upon therapeutic effectiveness of the extended terminal surface electrode array sufficient for hemicranial stimulation by allowing for more precise control of the therapeutic neurostimulation parameters.

In still another aspect, the implantable, head-mounted, neurostimulation system for head pain comprises multiple design features, including incorporating individual design features within each of the three or more individual surface electrode arrays. Examples of such intra-array design features would include the specific number of electrodes allotted to each group; whether the electrodes are cylindrical or flattened; the width of each electrode within each array, and the linear distance intervals of separation of the electrodes within each array. This feature further improves upon therapeutic effectiveness of the extended terminal surface electrode array sufficient for hemicranial stimulation, and the grouping of these electrodes into three or more separate surface electrode arrays, by providing each specific array location a unique intra-array design that takes into account, and thereby seeks to optimizes, design elements that are known to be possibly or likely beneficial to the therapeutic end result, given the anticipated post-implant anatomic location of that array.

In yet another aspect, an implantable peripheral neurostimulation system for head pain comprises multiple novel design features, including incorporating individual design features into a single lead design and thereby achieving additive benefits.

In still another aspect, an implantable peripheral neurostimulation system for head pain results in a marked decrease in the number of separate lead implants required to adequately treat a single patient. A single implant will provide the same therapeutic anatomic coverage that it would take for the implantation of three or four of the currently available leads. That is, instead of the current which often calls for three or more leads to be implanted to provide adequate hemicranial coverage, the same anatomic region may be covered with a single stimulator lead implant. The lead provides extended coverage over the full hemicranium; that is, achieving medically acceptable neurostimulation unilaterally over the frontal, parietal, and occipital regions simultaneously. In contrast, publically known leads are able to consistently provide medically acceptable neurostimulation therapy only over a single region, meaning that it would require three separate surgically lead implants to achieve the same therapeutic coverage of a single implant of a lead of the present disclosure. This will decrease the total number of surgeries required, as well as the extent of each individual surgery for many patients.

In another aspect, by having a system that is fully localized to the head, it eliminates the requirement of currently available systems of having long leads and extensions extending across the neck and back to IPG locations commonly in the low back and gluteal region, and thereby decreases the risk of problems attendant to such long leads and extensions, including discomfort, infection, technical extension issues such as fracture, and other morbidities. This results in a further decrease in the number of surgeries required by a patient.

In other aspects, an IPG may be of proper aspect ratio with respect to the specific site of intended implantation in the head, preferably an area posterior to and/or superior to the ear. There may be an external portable programming unit that is capable of achieving a radiofrequency coupling to the implanted unit. An IPG may have an internal RF receiver coil that is capable of coupling via a radiofrequency mechanism to an external control unit that provides power and control function. An IPG may contain an internal RF receiver, an application specific integrated circuit, and a supercapacitor. In the event the external power supply is lost, the supercapacitor can supply power to the device and keep the device functioning until the external power connection can be resumed. The system may include a primary cell as a power source. An IPG may be capable of being multiplexed, i.e., the IPG can be programmed to only stimulate (turn on) the required and necessary electrical contacts needed for therapy and turn off the ones not needed.

In other aspects, the system may include one or more of the following features. A neurostimulating lead may not require a central channel for a stylet. A neurostimulating lead may have a smaller diameter than currently available leads. A neurostimulating lead may have a shaped or flat electrode design that orients the electrical fields toward the specific nerves, thus avoiding stimulation of undesired tissues, e.g., adjacent muscles, while additionally improving patient cosmetics. A neurostimulating lead may include redundant electrodes for the shaped or flat electrode contacts such that in the event the leads are inadvertently flipped, these redundant electrodes can be selected and activated so that the electric fields can still be oriented at the proper nerves.

In other aspects, the system may include one or more of the following features. The system may include the disposition of a sufficient plurality of surface electrodes over a sufficient linear distance along the system's leads to enable medically adequate therapeutic stimulation across multiple regions of the head, and preferably the entire hemicranium; that is, over the frontal, parietal, and occipital region simultaneously. The extended array of surface electrodes may be divided into two or more discrete terminal surface electrode arrays. The preferred linear layout of these multiple surface electrode arrays includes at least one array positioned over the frontal region, at least one array positioned over the parietal region, and at least one array positioned over the occipital region.

In other aspects, intra-array design features may include variations in the specific number of electrodes allotted to each group; the shape of the electrodes, e.g., whether the electrodes are cylindrical or flattened; the width of each electrode within each array, and the linear distance intervals of separation of the electrodes within each array.

In other aspects, the system may include a plurality of connection ports that can be connected with a plurality of leads and thus allow for attaching additional leads should they later be required.

In another aspect, an implantable peripheral neurostimulation system for head pain comprises multiple design features; including features aimed at improving patient safety by improving the incidence of adverse events, including the risk of infection, as well as the risk and incidence of known technical problems associated with implanted leads, including lead migration and lead fracture, amongst others. The lead may comprise two or more (i.e. three or more) surface electrode arrays, each uniquely designed, that are disposed over a sufficient lead length to allow for medically acceptable therapeutic neurostimulator coverage of at least regions within the supraorbital, parietal, and occipital cranial regions. To achieve the same clinical coverage from a single implant, it would require three or more separately surgically implanted leads. Therefore, by reducing the number of surgical incisions, as well as the number of surgically implanted leads, the associated risks of adverse events are proportionally diminished.

In yet another aspect, an implantable peripheral neurostimulation system for head pain may treat chronic head and/or face pain of multiple etiologies, including migraine headaches; and other primary headaches, including cluster headaches, hemicrania continua headaches, tension type headaches, chronic daily headaches, transformed migraine headaches; further including secondary headaches, such as cervicogenic headaches and other secondary musculoskeletal headaches; including neuropathic head and/or face pain, nociceptive head and/or face pain, and/or sympathetic related head and/or face pain; including greater occipital neuralgia, as well as the other various occipital neuralgias, supraorbital neuralgia, auroiculotemporal neuralgia, infraorbital neuralgia, and other trigeminal neuralgias, and other head and face neuralgias.

In another aspect, an implantable, head-mounted, neurostimulation system for head pain comprises multiple design features, including features aimed at improving patient safety by improving the incidence of adverse events, including the risk of infection, as well as the risk and incidence of known technical problems associated with implanted leads, including lead migration and lead fracture, amongst others. The lead may comprise two or more (i.e. three or more) surface electrode arrays, each uniquely designed, that are disposed over a sufficient lead length to allow for medically acceptable therapeutic neurostimulator coverage of at least regions within the supraorbital, parietal, and occipital cranial regions. To achieve the same clinical coverage from a single implant, it would require three or more separately surgically implanted leads. Therefore, by reducing the number of surgical incisions, as well as the number of surgically implanted leads, the associated risks of adverse events are proportionally diminished.

In yet another aspect, an implantable, head-mounted, neurostimulation system for head pain may treat chronic head and/or face pain of multiple etiologies, including migraine headaches and other primary headaches, including cluster headaches, hemicrania continua headaches, tension type headaches, chronic daily headaches, transformed migraine headaches, further including secondary headaches, such as cervicogenic headaches and other secondary musculoskeletal headaches, including neuropathic head and/or face pain, nociceptive head and/or face pain, and/or sympathetic related head and/or face pain, including greater occipital neuralgia, as well as the other various occipital neuralgias, supraorbital neuralgia, auroiculotemporal neuralgia, infraorbital neuralgia, and other trigeminal neuralgias, and other head and face neuralgias.

In other aspects, an implantable, head-mounted, neurostimulation system for head pain may not require a central channel for stylet placement over its distal (frontal) portions. The lead may improve patient comfort and cosmetics by virtue of its relatively small diameter over the distal portions of the lead, partially due the lack of a central stylet channel, as well as due to a progressive decrease in the number of internal wires continuing after each terminal electrode. The lead may further improve cosmetic appearance and patient comfort by incorporating a flattened lead design for that portion of the lead expected to be over the frontal portion of the head.

Thus, the present disclosure provides for a peripheral neurostimulation lead that is uniquely designed for implantation in the head as a therapy for chronic head pain, and is designed to solve the known design issues associated with current leads, as the lead of the present disclosure seeks to optimize the therapeutic response, improve patient comfort, improve cosmetics, reduce the number of surgical leads required, and reduce medical risk, and reduce medical costs.

B. Overview

Turning now descriptively to the drawings, in which similar reference characters denote similar elements throughout the several views, the figures illustrate an implantable pulse generator (IPG) from which two neurostimulating leads may extend to a length sufficient to allow for therapeutic neurostimulation unilaterally over the frontal, parietal and occipital regions. The leads include an extended plastic lead body, a plurality of surface metal electrodes disposed along the lead, which may be divided into two or more electrode arrays, a plurality of internal electrically conducting metal wires running along at least a portion of its length and individually connecting the IPG's internal circuit to individual surface metal electrodes. The implantable pulse generator includes the internal circuits, a radiofrequency receiver coil, and an ASIC. The system may be operable to provide medically acceptable therapeutic neurostimulation to multiple regions of the head, including the frontal, parietal and occipital regions simulataneously, and six figures demonstrate various views of this feature as the system is depicted in situ.

C. Full Head-Located Neurostimulator System

FIG. 1 depicts a side view of a full neurostimulator system, which consists of an implantable pulse generator (IPG) 10 along with two unibody plastic lead extensions—a Fronto-Parietal Lead (FPL) 20 and an Occipital Lead (OL) 30 of adequate length to extend to roughly the midline of the forehead and to the midline at the cervico-cranial junction, respectively. Arrows 28 indicate the point of cross section of FIG. 4.

Figure 5:
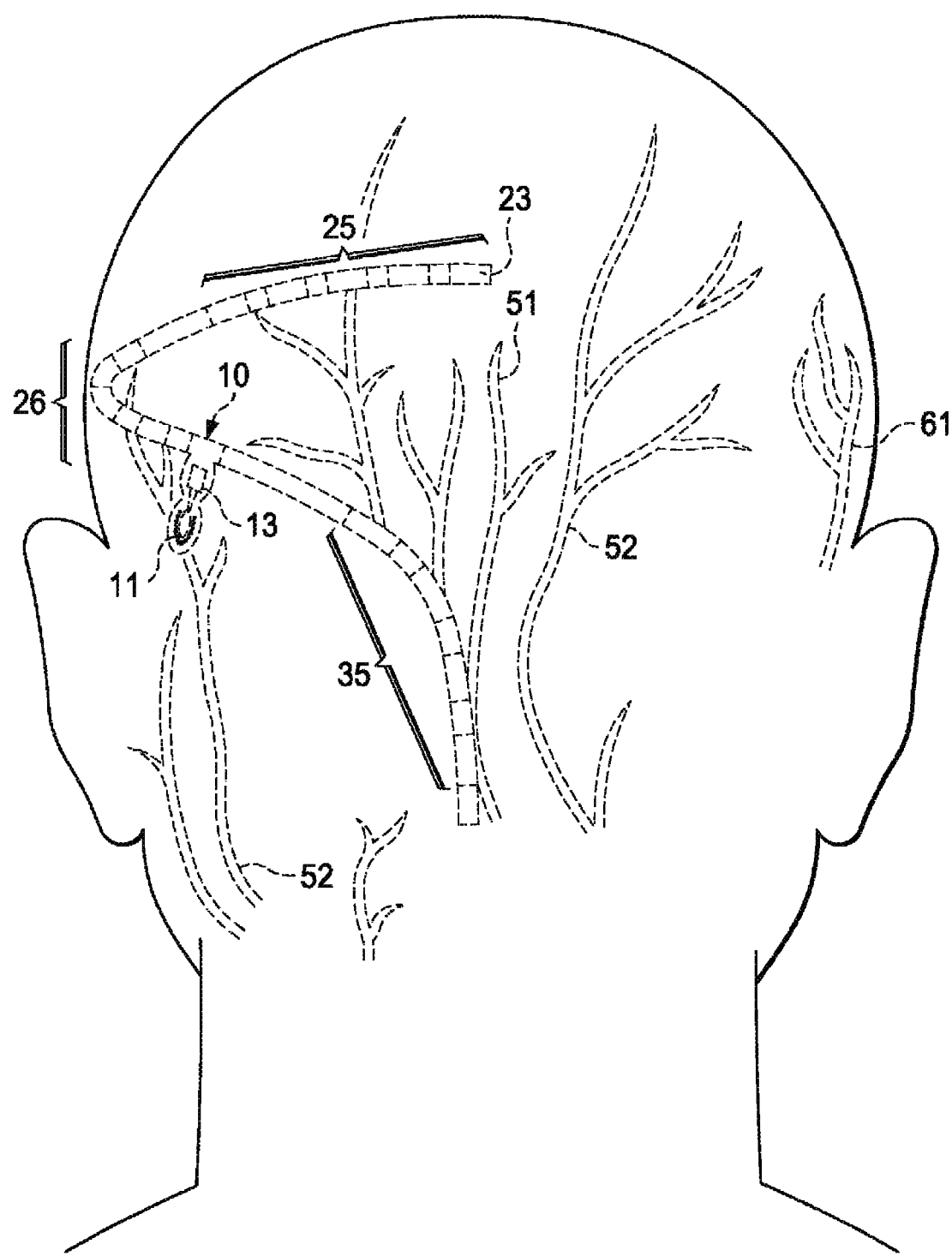
FIG. 5 depicts a rear view of a Head with a full Head-Located Neurostimulator System In-Situ. Prominent here is the OL depicted passing from the IPG caudally and medially across the occipital region, whereby the OEA is disposed in a fashion to cross over and cover the major associated nerves—primarily the greater occipital nerve, but typically including the lessor and/or third occipital nerve as well. Also depicted are the PEA and the FEA of the FPL as they cross and cover the primary nerves of the Parietal Region, including the auriculo-temporal nerve, and the Frontal Region, including the supraorbital nerve. Also depicted is the IPG with its Internal Circuit, Internal RF Receiver Coil, and ASIC.
Figure 6:
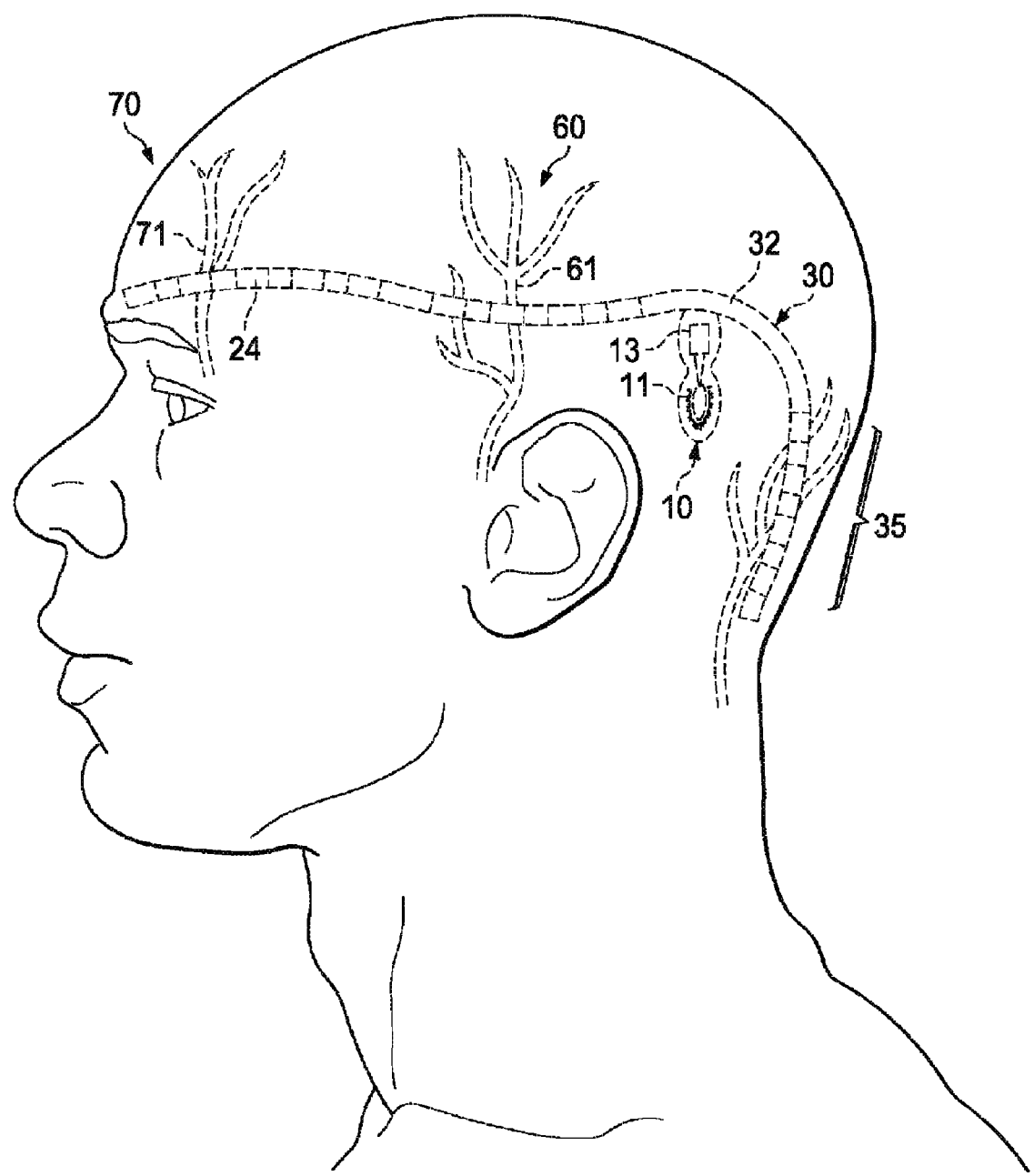
FIG. 6 depicts a side view of a Head with a full Head-Located, Unibody Radiofrequency-Coupled Neurostimulator System In-Situ. Prominent here is the PEA, as it covers a portion of the Parietal Region 60 and the major associated nerves, including the auriculo-temporal nerve 61 as well as other adjacent cutaneous nerves. The frontal region of the head and supraorbital nerve 71 are also depicted. Also depicted are the courses of the distal portion of the FPL and the OL, as they pass over and cover the associated nerves of the Frontal (Supraorbital) and Occipital Regions. Also depicted is the IPG including its Internal Circuit, ASIC, and RF Receiver Coil.
Figure 7:
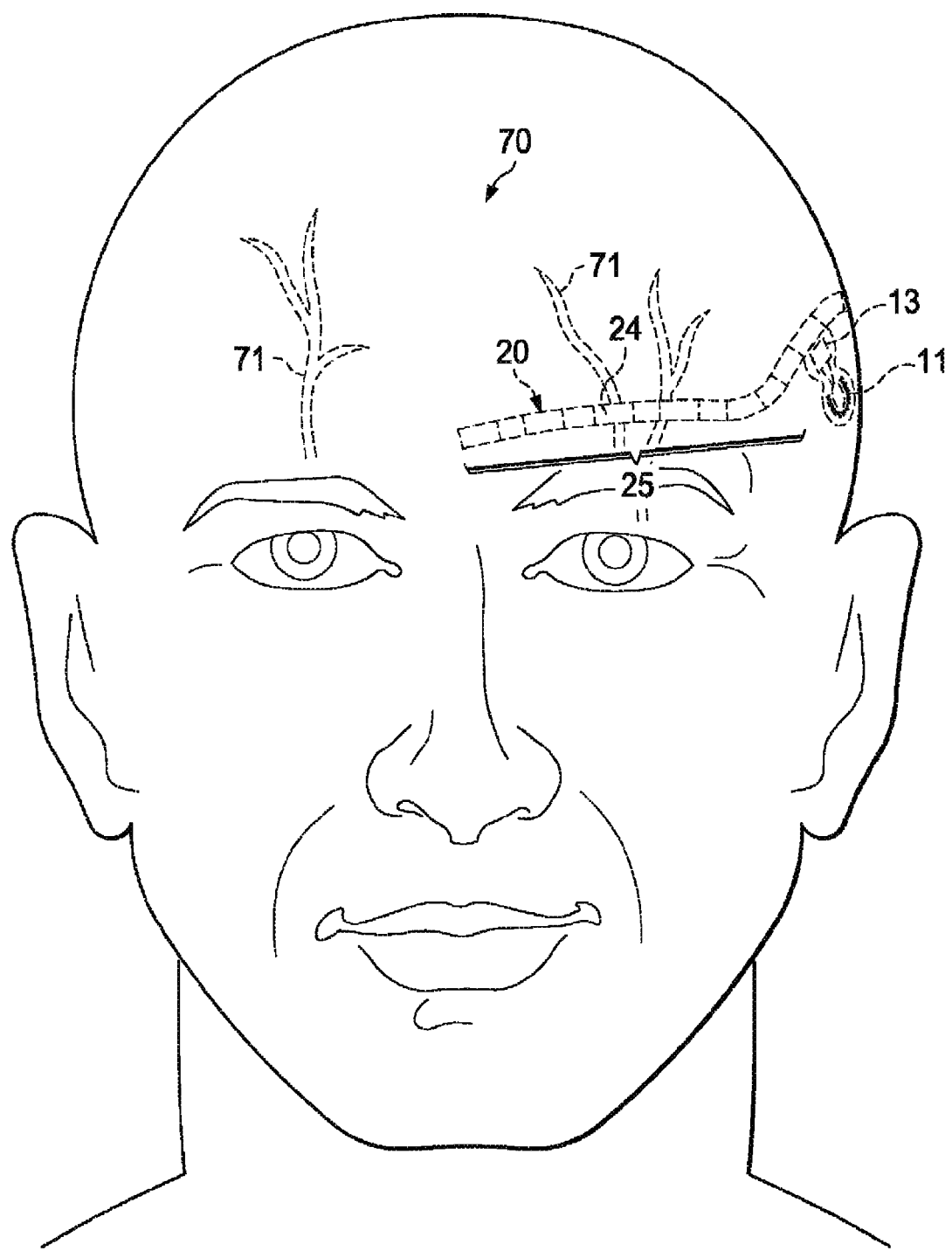
FIG. 7 depicts a front view of a Head with a full Head-Located, Unibody Radiofrequency-Coupled Neurostimulator System In-Situ. Prominent here is the FEA, as it covers a portion of the Frontal (Supraorbital) Region and the major associated nerves—primarily the supraorbital nerve, but also commonly the greater trochlear nerve, as well as adjacent nerves. Also depicted is the course of the parietal portion of the FL. Also depicted is the IPG including its Internal Circuit, ASIC, and RF Receiver Coil.

FIGS. 5, 6, and 7 depict posterior, lateral and frontal views of the system in-situ. The unit is demonstrated in an implant position where the IPG 10 is posterior and cephalad to the pinna of the ear. The drawings demonstrate the FPL 20 passing over the parietal 60 and frontal 70 regions of the head, including auriculo-temporal nerve 61 and supraorbital nerve 71, in a manner that places the FEA over the supraorbital nerve and the PEA over the auriculotemporal nerve. The OL 30 is shown passing caudally and medially over the occipital region of the head such that the OEA 35 cross over the greater occipital nerve 51, the lesser occipital nerve 52, and the third occipital nerve.

Figure 8:
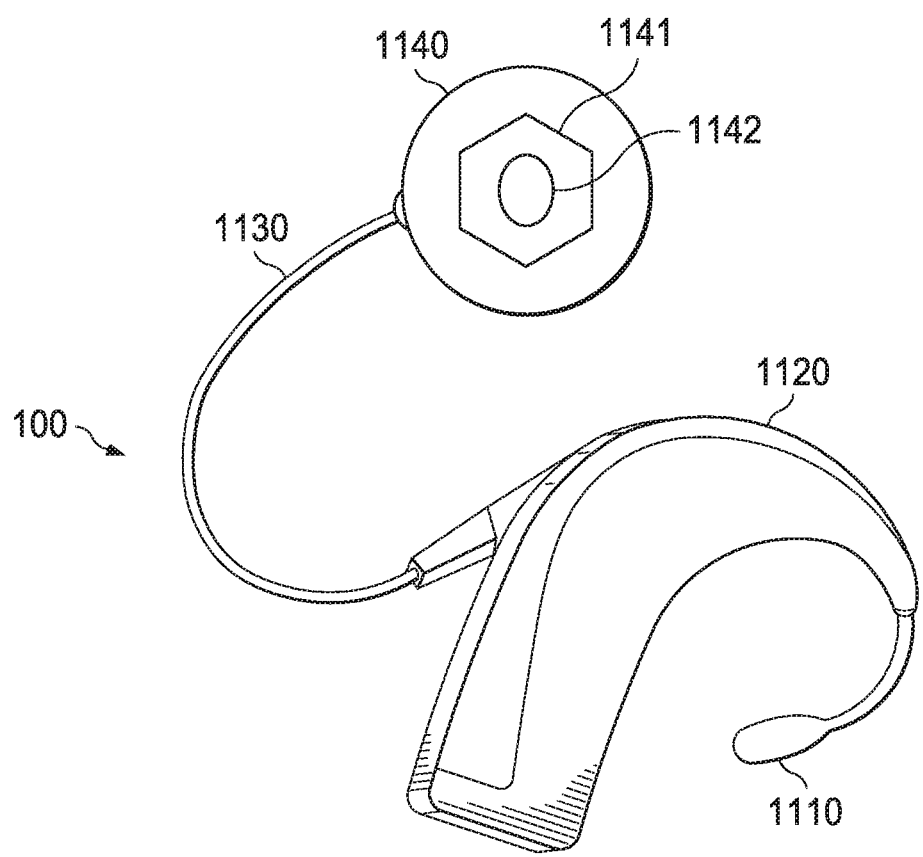
FIG. 8 depicts a side view of the External "Behind the Ear" Assembly. Prominent here is the IPG with its IPG including its Internal Circuit, ASIC, and RF Receiver Coil. The External Assembly includes the External Earl Clip, the Behind-the-Ear Electronics and Battery Component, the External Coil Lead, and the External RF Coil Plastic Housing, which contains the External RF Coil and External RF Magnet.
Figure 9:
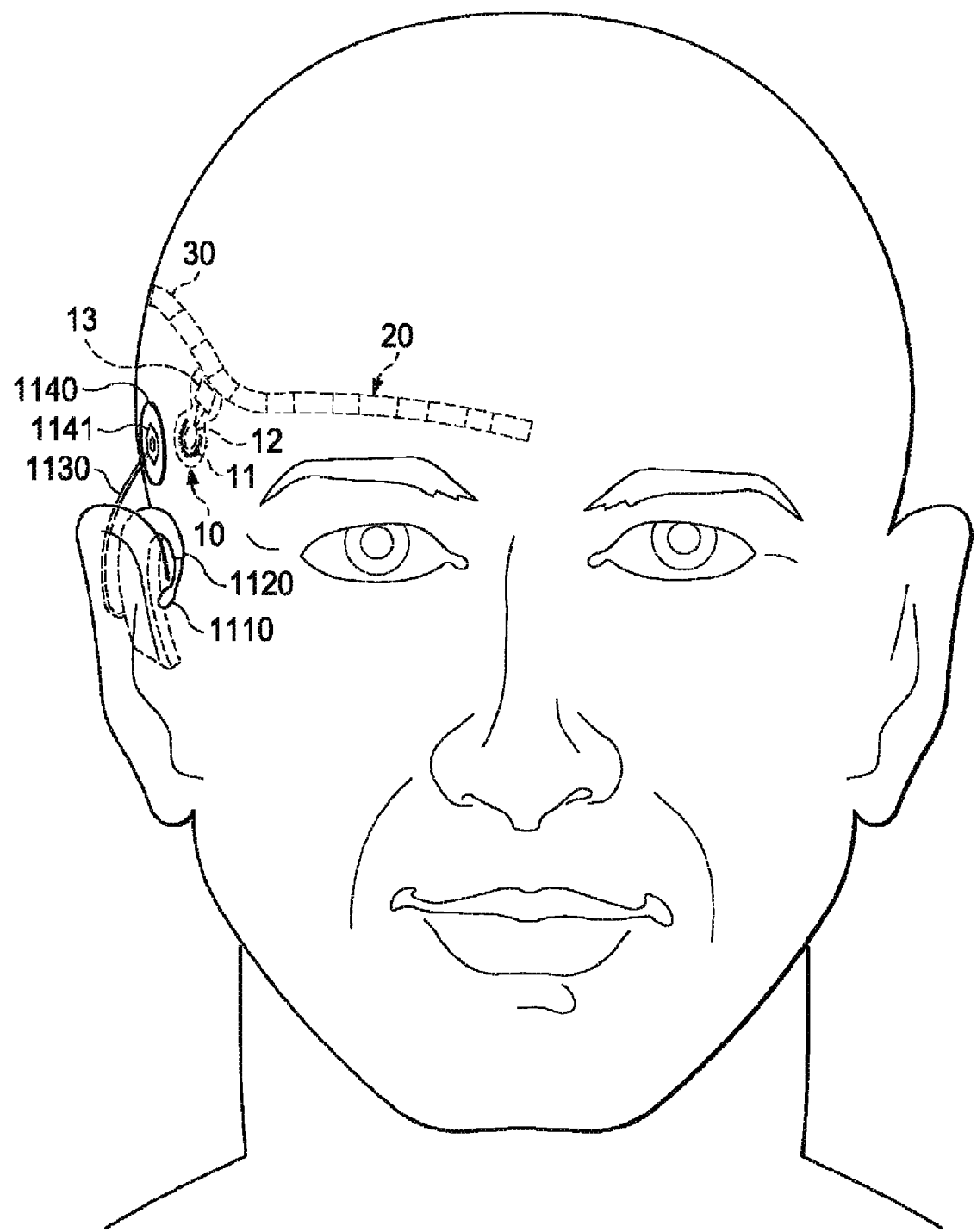
FIG. 9 depicts right oblique front view of a head with a full Head-Located, Unibody Radiofrequency-Coupled Neurostimulator System In-Situ, along with an External "Behind the Ear" Assembly. Prominent here is the IPG with its IPG including its Internal Circuit, ASIC, and RF Receiver Coil. The External Assembly includes the External Earl Clip, the Behind-the-Ear Electronics and Battery Component, the External Coil Lead, and the External RF Coil Plastic Housing, which contains the External RF Coil and External RF Magnet.

FIGS. 8 and 9 depict two views of the external control unit (ECU) 100. FIG. 8 depicts a side view of an ECU 100, the components of which include an ear clip 1110, an electronics and battery component (EBC) 1120, an external coil lead 1130, and an external RF coil housing 1140 that contains a RF coil 1141 external magnet 1142. FIG. 9 depicts a right oblique frontal view of the head with an implantable neurostimulator system in-situ, and with the ECU 100 attached to the ear in its functional position, with the external RF coil housing 1140 in position opposite the internal RF coil 11 and internal magnet 12 of the IPG 10.

D. Fronto-Parietal Lead

Continuing with FIG. 1, the FPL 20, as part of the unibody construction, extends from the IPG. The FPL comprises a plastic body member 20a and a set of internal conducting wires 29.

The plastic body member 20a is an elongated, cylindrical, flexible member, which may be formed of a medical grade plastic polymer. It has a proximal end 22, a distal end 21, and may be conceptually divided into five segments along its linear dimension. Progressing from the proximal end 22, these segments sequentially include a proximal lead segment (PLS) 22a, a parietal electrode array (PEA) 26, an inter-array interval 27, a frontal electrode array (FEA) 25, and a distal non-stimulating tip 23.

Figure 4:
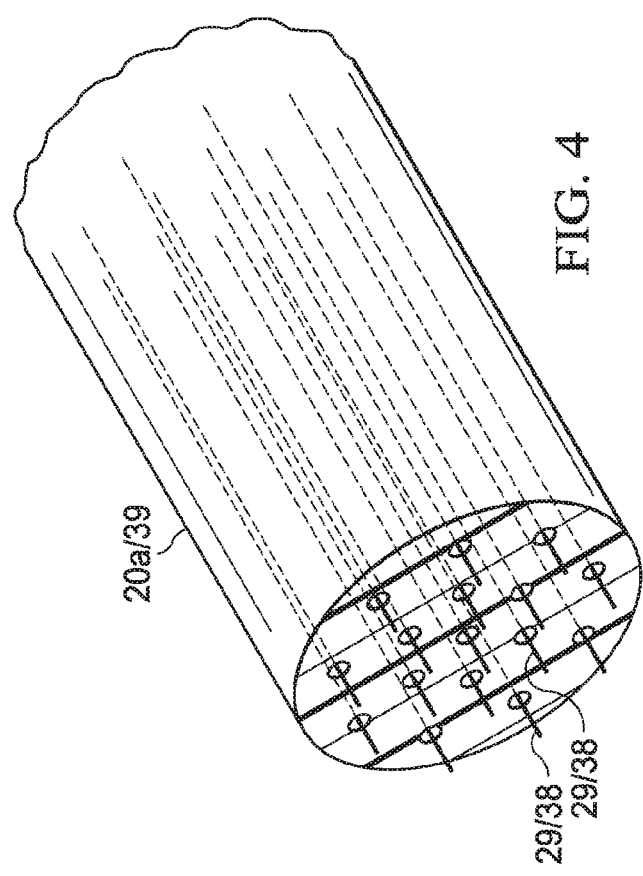
FIG. 4 depicts a cross-sectional view of a Lead Central Body comprising a Cylindrical Lead Body (with Internal Wires) between the IPG Internal Circuit and the Lead Surface Electrodes.

The lead internal wires 29 pass along the interior of the plastic body member as depicted in FIG. 4.

E. Frontal Electrode Array

Continuing with FIG. 1, the FEA 25 consists of a plurality of surface metal electrodes (SME) 24 uniformly disposed over a portion of the distal aspect of the FPL 20. Lead internal wires 29 connect to the SME 24 as depicted in FIG. 2, which represents the distal four SME 24 of the lead.

F. Parietal Electrode Array

Returning to FIG. 1, the PEA 26 consists of a plurality of SME 24 uniformly disposed along a linear portion of the FPL. The PEA 26 is separated along the FPL from the FEA by an inter-array interval 27. It is separated only the lead from the IPG by the PLS 22a. The lead internal wires 29 connect to the individual SMEs 24 of the PEA in the same fashion as the do with the SME of the FEA as shown in FIG. 2.

G. Occipital Lead

Continuing with FIG. 1, the occipital lead (OL) 30 as part of the unibody construction extends from the IPG 10. It comprises a plastic body member 39 and a set of lead internal wires 38 that pass through the central cylinder of the lead to connect to a series of SME 34, each of surface electrode width 37, that are uniformly disposed at an inter-electrode distance 36 from each other along a portion of the length of the lead. These lead internal wires 38 pass and connect in the same manner as described above for the SME 24 of the FEA 25 as depicted in FIGS. 2 and 4.

The plastic body member 39 is an elongated, cylindrical, flexible member, which may be formed of a medical grade plastic polymer. It has a proximal end 32 and a distal end 31. Progressing along the lead from the proximal end 32, these segments sequentially include a proximal lead segment (PLS) 32a, an occipital electrode array (OEA) 35, and a distal non-stimulating tip 33.

H. Occipital Lead Array

As depicted in FIG. 1, the OEA 35 consists of a plurality of surface metal electrodes (SME) 34 uniformly disposed over a portion OL 30. Lead internal wires 38 connect to the SME 24 in the same fashion as depicted for the FEA 25 as shown in FIG. 2.

I. Implantable Pulse Generator

Figure 3:
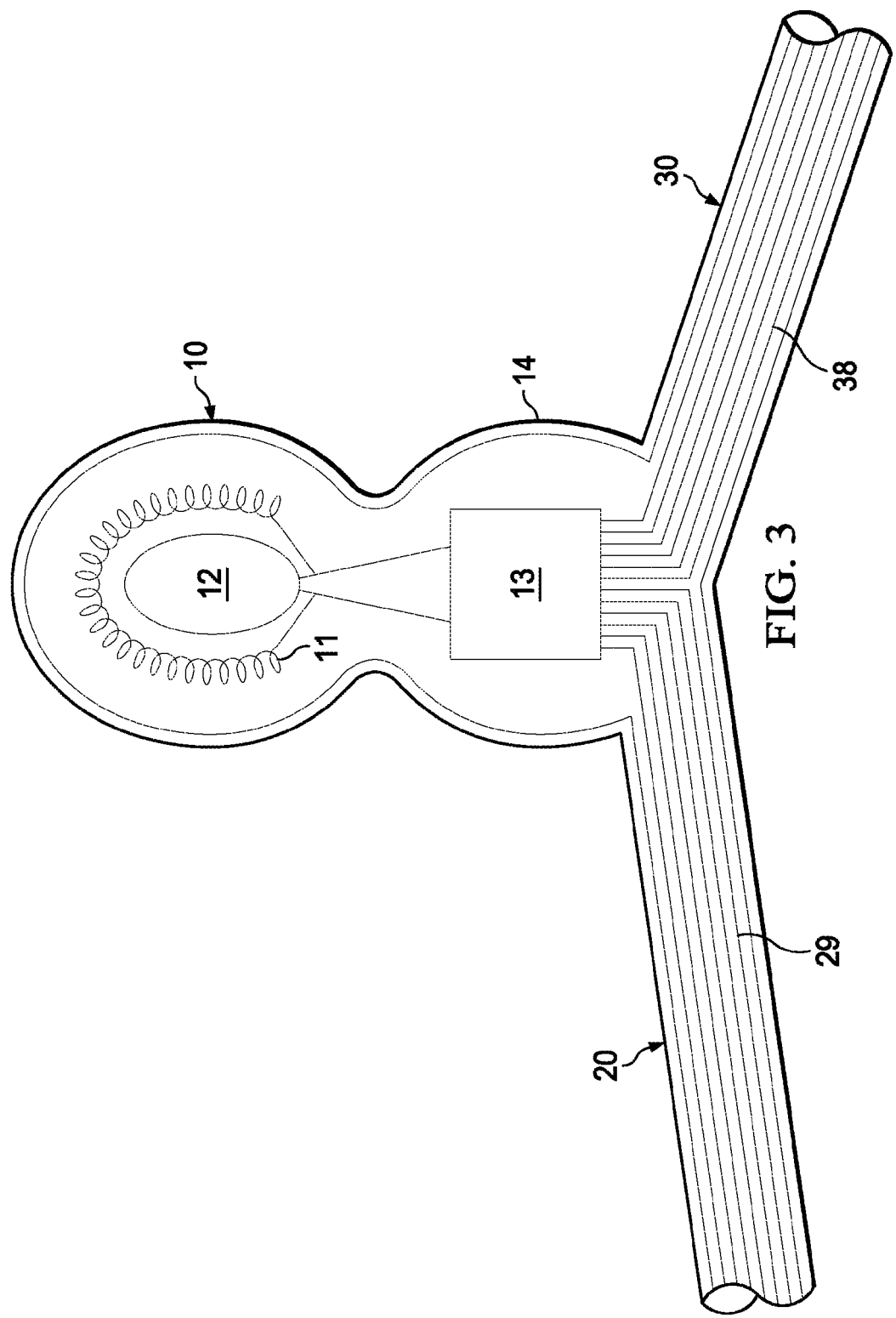
FIG. 3 depicts a side view of an IPG, along with its enclosed ASIC, RF Receiver Coil, and Internal Magnet, along with the Internal Wires exiting from the IPG's Internal Circuit enroute to the Surface Electrodes disposed over the FPL and the OL.

Referring to FIG. 1 and FIG. 3, the three primary physical and functional components of the IPG 10 include an internal magnet 12, an internal radiofrequency receiver coil 11, and an application specific integrated circuit (ASIC) 13, along with the necessary internal wire connections amongst these related components, as well as to the incoming lead internal wires 29, 39. These individual components may be encased in a can made of a medical grade metal and plastic cover 14, which itself transitions over the exiting FPL 20 and OL 30.

Referring now to FIGS. 1A and 1B, there are illustrated embodiments of the IPG 10 and the various configurations of the lead. In FIG. 1A, the FPL lead 20 and the OL lead 30 are illustrated as extending downward from the IPG body 10. In FIG. 1B, the coil 11 and the magnet 12 are disposed in a separate body 10' that is disposed distal from the integrated circuit 13 or ASIC 13 by a lead 20'. This allows the coil 11 to be disposed at a point in the hemicranium distal from the ASIC 13. For implantation, the magnet 12 is removed therefrom and the body 10' is "rolled up" in a tube with the approximate diameter of the lead 20', such that it can be routed subcutaneously to a different location about the head. This is to facilitate coupling with an external coil in a more comfortable manner for the patient.

J. External Controller

FIG. 8 depicts an external "behind the ear" controller (EC) 100, which includes an ear clip 1110, an electronics and battery component (EBC) 1120, an external coil lead 1130 and an external RF coil plastic housing (ECPH) 1140, which contains the external RF coil 1141, and the external magnet 1142.

FIG. 9 depicts a right oblique frontal view of the head with an in-situ full neurostimulator system. The EC 100 is depicted as secured into position by an ear clip 1110, and the ECPH 1140 is depicted as applied to the skin directly over the internal radiofrequency receiver coil 11 and internal magnet 12 components of the IPG 10.

K. Connections of Main Elements and Sub-Elements

The system may include a unibody construction to provide physical and functional continuity of the related components and sub-components.

The overall mechanistic purpose of an implantable neurostimulation system is to generate and conduct a prescribed electrical pulse wave from an IPG 10 down a set of lead internal wires 29, 38 running a portion of the length of the lead to specified programmed set of SMEs 24, 34, whereby the current is then conducted by tissue and/or fluid to an adjacent, or nearby, set of one or more SME 24, 34, which in turn passes the signal proximally down the lead wire 29, 38 back to the IPG 10 and its ASIC 13, thus completing the circuit.

An external control unit (ECU) 100 provides power, programming and diagnostic functionality to the implanted neurostimulator system via a radiofrequency couple between the external RF coil 1141 and internal RF coil 1142. The ECU 100 is held in place on the head by an ear clip 1110, and its ECPH 1140 is held in place over the IPG 10 by internal and external magnets 12, 1142.

L. Charge Transfer/Communication Control

Figure 10:
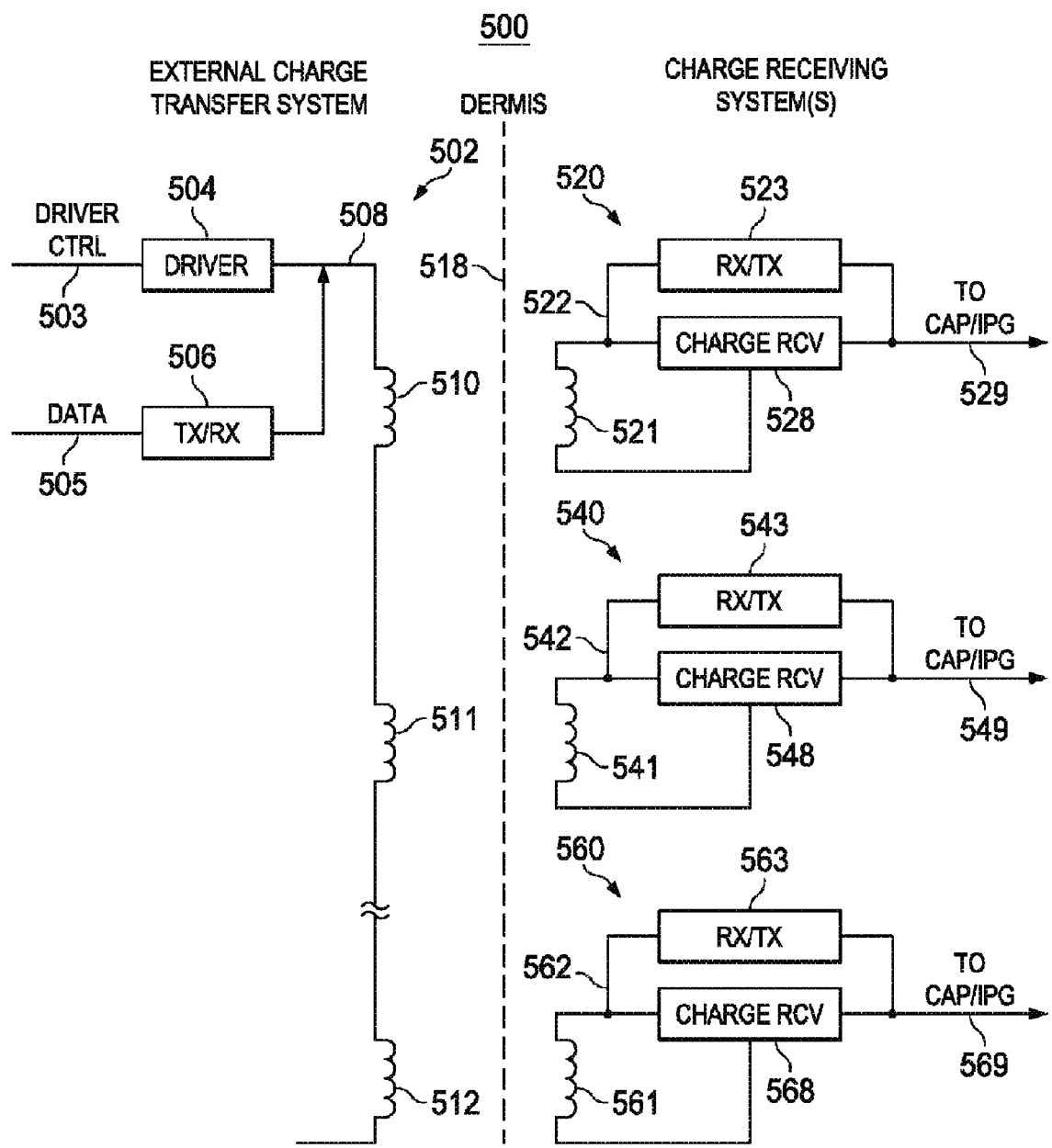
FIG. 10 is a block diagram of a system that provides for independent charge transfer and communication with multiple implanted devices, in accordance with some embodiments of the invention.

FIG. 10 depicts a conceptual diagram of a system 500 that provides for independent charging/powering and communication with multiple body-implanted pulse generating (IPG) devices requiring external power to either power the IPGs directly or to charge an internal supercapacitor associated with the IPGs or a hybrid thereof. For the purposes of this disclosure, charge provided to the IPGs will be referred to as "charge transfer," but it should be understood that this could mean charging of a supercapacitor or delivering charge to a powered element associated with the IPGs. Three charge receiving systems 520, 540, 560 are shown, each disposed within a corresponding IPG (not shown). An external charge transfer system 502 disposed outside a dermis layer (or "dermal layer") 518 includes series-connected charge transfer coils, of which three are shown, being series-connected charge transfer coils 510, 511, 512, each of which corresponds to a respective one of receive coils 521, 541, 561 of respective ones of a plurality of charge receiving systems, of which three are shown, being charge receiving systems 520, 540, 560. Preferably each receive coil 521, 541, 561 is tuned to the resonant frequency of the respective charge transfer coil 510, 511, 512 within the external charge transfer system 502. While three charge transfer coils 510, 511, 512 are shown, one for each charge receiving system 520, 540, 560, other embodiments may utilize one charge transfer coil, two charge transfer coils, or another number of charge transfer coils, depending upon the number of IPGs.

The external charge transfer system 502 includes a driver 504, responsive to a DRIVER CTRL signal on node 503, for driving the series-connected coils 510, 511, 512 with an AC signal. A TX/RX telemetry block 506 includes a transmitter for transmitting forward telemetry data signal within the AC signal driven across the charge transfer coils (i.e., on node 508), and a receiver to detect and receive a back telemetry data signal within the AC signal. The forward/back telemetry data signals, both as represented by the DATA signal on node 505, are coupled from/to telemetry circuitry within remaining portions of the external charge transfer system (not shown). As used herein, data communication from an external charge transfer system to an IPG is referred to as forward telemetry, and data communication from an IPG to an external charge transfer system is referred to as back telemetry.

Within the first IPG, the charge receiving system 520 includes a receive coil 521 that is tuned to the resonant frequency of the associated charge transfer coil 510 within the external charge transfer system 502, so that receive coil 521 may receive energy transferred from the charge transfer coil 510 when in close proximity thereto. The receive coil 521 is coupled to a charge receiving block 528 that includes circuitry for receiving energy in a first mode of operation, and for de-tuning the receive coil 521 in a second mode of operation to inhibit transfer of energy. The receive coil 521 is also coupled (via node 522) to an RX/TX telemetry block 523 that includes a receiver for receiving a forward telemetry data signal from the receive coil 521, and a transmitter for transmitting a back telemetry data signal to the receive coil 521. The received energy is coupled to charge transfer circuitry, and the forward/back telemetry data signals are coupled to/from data circuitry within the first IPG, both as represented by node 529. As can be appreciated, the receive coil 521 serves as a "shared antenna" for both the charge transfer system and the telemetry system.

Similarly, the charge receiving system 540 includes a receive coil 541 that is tuned to the resonant frequency of the associated charge transfer coil 511, so that receive coil 541 may receive energy transferred from the charge transfer coil 511 when in close proximity thereto. The receive coil 541 is coupled to a charge receiving block 548 that includes circuitry for receiving energy in the first mode of operation, and for de-tuning the receive coil 541 in the second mode of operation to inhibit transfer of energy. The receive coil 541 is also coupled (via node 542) to an RX/TX telemetry block 543 that includes a receiver for receiving a forward telemetry data signal from the receive coil 541, and a transmitter for transmitting a back telemetry data signal to the receive coil 541. The received energy is coupled to charge transfer, and the forward/back telemetry data signals are coupled to/from data circuitry within the second IPG, both as represented by node 549.

Likewise, the charge receiving system 560 includes a receive coil 561 that is tuned to the resonant frequency of the associated charge transfer coil 512, so that receive coil 561 may receive energy transferred from the charge transfer coil 512 when in close proximity thereto. The receive coil 561 is coupled to a charge receiving block 568 that includes circuitry for receiving energy in the first mode of operation, and for de-tuning the receive coil 561 in the second mode of operation to inhibit transfer of energy. The receive coil 561 is also coupled (via node 562) to an RX/TX telemetry block 563 that includes a receiver for receiving a forward telemetry data signal from the receive coil 561, and a transmitter for transmitting a back telemetry data signal to the receive coil 561. The received energy is coupled to charge transfer circuitry, and the forward/back telemetry data signals are coupled to/from data circuitry within the third IPG, both as represented by node 569.

Even though a single driver circuit 504 is utilized to drive all three series-connected charge transfer coils 510, 511, 512, the system 500 provides for independent charge transfer (or charge delivery) of multiple IPGs. When such charge transfer of one of the IPGs is complete (or delivery of charge), the corresponding de-tuning circuitry within the respective charge receiving circuit 528, 548, 568 may be activated to de-tune its respective receive coil 521, 541, 561 and thereby inhibit further transfer of energy to the respective charge receiving circuit 528, 548, 568. Each IPG may de-tune its receive coil when charge transfer is complete, independently of the other IPGs, to limit needless power loss and undesirable heating within an IPG, without affecting energy transfer to the remaining charge receiving systems 520, 540, 560.

Moreover, even though a single driver circuit 504 is utilized to drive all three series-connected charge transfer coils 510, 511, 512, the system 500 also provides for independent communication with multiple IPGs. Since the forward telemetry (transmit) data signal within the AC signal is driven across all three series-connected charge transfer coils 510, 511, 512, each of the charge receiving systems 520, 540, 560 can independently receive such a transmitted data signal. As for receiving data independently from each charge receiving system, the external charge transfer system 502 can coordinate the operation of each charge receiving system 520, 540, 560 so that only one such charge receiving system at a time attempts to communicate back telemetry data to the external charge transfer system 502. Such coordination may be achieved by forward telemetry commands instructing a selected charge receiving system to communicate back telemetry data to the external charge transfer system 502, so that the non-selected charge receiving systems will forego attempted back telemetry during such times. Embodiments described below provide detailed examples of forward and back telemetry circuitry and operation.

Figure 11:
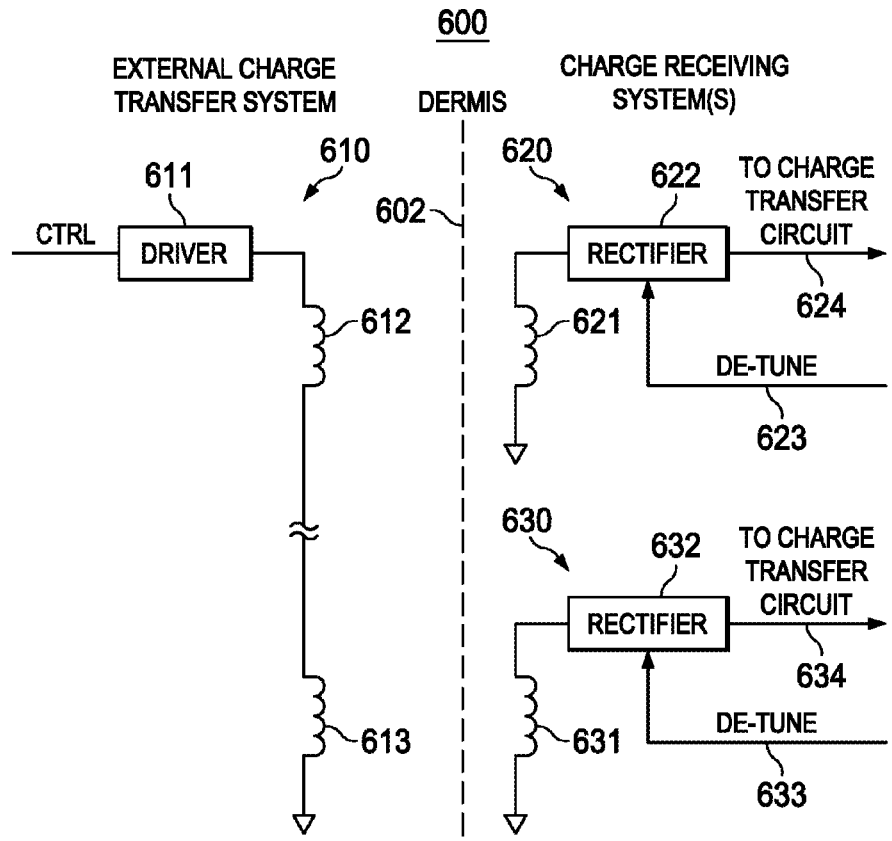
FIG. 11 is a block diagram of a system depicting the de-tuning of a receive coil within an implanted device to selectively turn off charging, in accordance with some embodiments of the invention.

FIG. 11 is a block diagram of a system 600 that provides for the de-tuning of a receive coil within a given IPG to selectively turn off charge transfer (charge delivery) of the given device without affecting charge delivery in one or more other such IPGs. Two charge receiving systems 620, 630 are shown, each disposed within a corresponding IPG. An external charge delivery system 610 disposed outside a dermis layer 602 includes series-connected charge transfer coils 612, 613, each of which corresponds to a respective one of receive coils 621, 631 of respective charge receiving systems 620, 630. In this embodiment, two such charge transfer coils 612, 613 are shown, one for each charge receiving system 620, 630, but other embodiments may utilize one charge transfer coil or another number of charge transfer coils, depending upon the number of IPGs.

The external charge transfer system 610 includes a driver 611, responsive to a CTRL signal, for driving the series-connected charge transfer coils 612, 613 with an AC signal. Within the first IPG, the charge receiving system 620 includes a receive coil 621 that is preferably tuned to the resonant frequency of the associated charge transfer coil 612 within the external charge transfer system 610, so that receive coil 621 may receive energy transferred from the charge transfer coil 612 when in close proximity thereto. The receive coil 621 is coupled to a rectifier block 622 for receiving energy in a first mode of operation and generating a rectified voltage on node 624, and for de-tuning the receive coil 621 in a second mode of operation, responsive to a DE-TUNE signal on node 623, to inhibit transfer of energy. The rectified voltage on node 624 is coupled to charge transfer circuitry within the first IPG (not shown).

Within the second IPG, the charge receiving system 630 includes a receive coil 631 that is preferably tuned to the resonant frequency of the associated charge transfer coil 613 within the external charge transfer system 610, so that receive coil 631 may receive energy transferred from the charge transfer coil 613 when in close proximity thereto. The receive coil 631 is coupled to a rectifier block 632 for receiving energy in the first mode of operation and generating a rectified voltage on node 634, and for de-tuning the receive coil 631 in the second mode of operation, responsive to a DE-TUNE signal on node 633, to inhibit transfer of energy. The rectified voltage on node 634 is coupled to charge transfer circuitry within the second IPG (not shown).

Even though a single driver circuit 611 is utilized to drive both series-connected charge transfer coils 612, 613, the system 600 provides for de-tuning of a receive coil within a given IPG to selectively turn off charging of the given device without affecting charging of one or more other such IPGs. As such, independent charge transfer of multiple IPGs is provided. When such charge transfer of one of the IPGs is complete, the corresponding DE-TUNE signal may be activated within the respective charge receiving system 620, 630 to de-tune its respective receive coil 621, 631 and thereby inhibit transfer of energy to the respective charge receiving system 620, 630. Each IPG may de-tune its receive coil when charge transfer is complete, independently of the other IPGs, to limit needless power loss and undesirable heating within a fully-charged IPG, without affecting energy transfer to the remaining charge receiving systems 620, 630. Such completion of charge transfer may be determined within the charge receiving system of the respective IPG, with or without any communication to the external charge transfer system.

Figure 12:
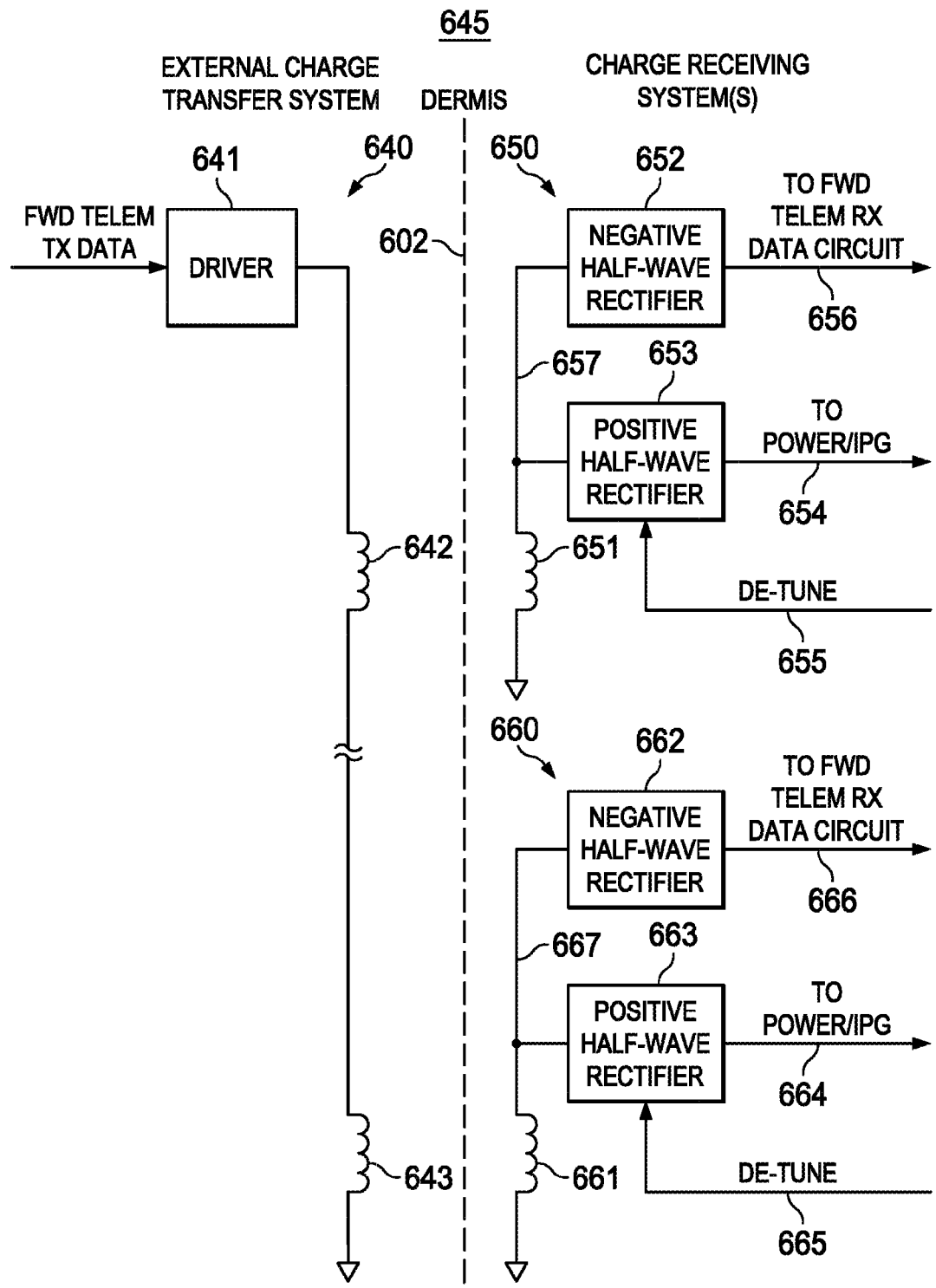
FIG. 12 is a block diagram of a system which provides for data communication (forward telemetry) and power transmission to an implanted device using opposite polarity half-wave rectified signals received by the implanted device, in accordance with some embodiments of the invention.

FIG. 12 is a block diagram of a system 645 which provides for power transmission and data communication to an IPG using opposite-polarity half-wave rectified signals received by the implanted device. Two charge receiving systems 650, 660 are shown, each disposed within a corresponding IPG. An external charge transfer system 640 disposed outside a dermis layer 602 includes series-connected charge transfer coils 642, 643, each of which corresponds to a respective one of receive coils 651, 661 of respective charge receiving systems 650, 660. Preferably each receive coil 651, 661 is tuned to the resonant frequency of the respective charge transfer coil 642, 643 within the external charge transfer system 640. In this embodiment, two such charge transfer coils 642, 643 are shown, one for each charge receiving system 650, 660, but other embodiments may utilize one charge transfer coil or another number of charge transfer coils.

The external charge transfer system 640 includes a driver 641 that is responsive to a forward telemetry transmit data signal FWD TELEM TX DATA. When the FWD TELEM TX DATA signal has a first logic state (e.g., logic high), the driver 641 drives the series-connected charge transfer coils 642, 643 with an AC signal, and when the FWD TELEM TX DATA signal has a second logic state (e.g., logic low), the driver 641 is disabled. In some embodiments, the driver 641 together with the series-connected charge transfer coils 642, 643 may be configured as a resonant amplifier. When such a resonant amplifier is disabled, the AC signal is allowed to decay and eventually cease.

Such operation may be viewed as providing a 100% amplitude-modulated AC signal driven across the series-connected charge transfer coils 642, 643, controlled by a bit-serial forward telemetry data signal FWD TELEM TX DATA. Significant charge transfer to one or both charge receiving systems 650, 660 is still readily provided for charge transfer by limiting the duration of time that the forward telemetry transmit data signal FWD TELEM TX DATA is allowed to "disable" the coil driver 641. Consequently, such a signal also functions as an enable/disable signal for the driver 641 if maintained in the second logic state.

Within a first IPG, the charge receiving system 650 includes a receive coil 651 for receiving energy transferred from the associated charge transfer coil 642 when in close proximity thereto. The receive coil 651 is coupled to a positive half-wave rectifier block 653 for receiving energy and generating a rectified voltage on node 654, and responsive to a DE-TUNE signal on node 655, for de-tuning the receive coil 651 to inhibit transfer of energy from the associated charge transfer coil 642. The rectified voltage on node 654 is coupled to charge transfer circuitry within the first IPG (not shown), which circuitry also directly or indirectly controls the DE-TUNE signal on node 655 when charging is complete or charge transfer is not desired. The receive coil 651 is also coupled via node 657 to a negative half-wave rectifier block 652 for receiving forward telemetry data and generating on node 656 a respective forward telemetry receive data signal, which is conveyed to forward telemetry receive data FWD TELEM RX DATA circuitry within the first IPG (not shown).

Within a second IPG, the charge receiving system 660 includes a receive coil 661 for receiving energy transferred from the associated charge transfer coil 643 when in close proximity thereto. The receive coil 661 is coupled to a positive half-wave rectifier block 663 for receiving energy and generating a rectified voltage on node 664, and responsive to a DE-TUNE signal on node 665, for de-tuning the receive coil 661 to inhibit transfer of energy from the associated charge transfer coil 643. The rectified voltage on node 664 is coupled to charge transfer circuitry within the second IPG (not shown), which circuitry also directly or indirectly controls the DE-TUNE signal on node 665 when charging is complete or charge transfer is not desired. The receive coil 661 is also coupled via node 667 to a negative half-wave rectifier block 662 for receiving forward telemetry data and generating on node 666 a respective forward telemetry receive data signal, which is conveyed to forward telemetry receive data FWD TELEM RX DATA circuitry within the first IPG (not shown).

As may be appreciated, each IPG can receive forward telemetry data independently, irrespective of the charging state (i.e., de-tuned state) of that IPG or of the other IPG. For example, the charge receiving system 650 may still receive forward telemetry information by the negative half-wave rectifier 652 irrespective of whether the positive half-wave rectifier 653 is de-tuned or not. Such de-tuning greatly lowers the resonant Q of the combination of charge transfer coil 642 and charge receive coil 651 for positive voltage excursions on node 657, and consequently serves to inhibit significant energy transfer to receive coil 651, but does not negatively impact the ability for the negative half-wave rectifier 652 to respond to negative transitions on node 657 and generate the output voltage accordingly on node 656. Similarly, the charge receiving system 650 may still receive forward telemetry information irrespective of whether the positive half-wave rectifier 663 within the other charge receiving system 660 is de-tuned or not.

Figure 13B:
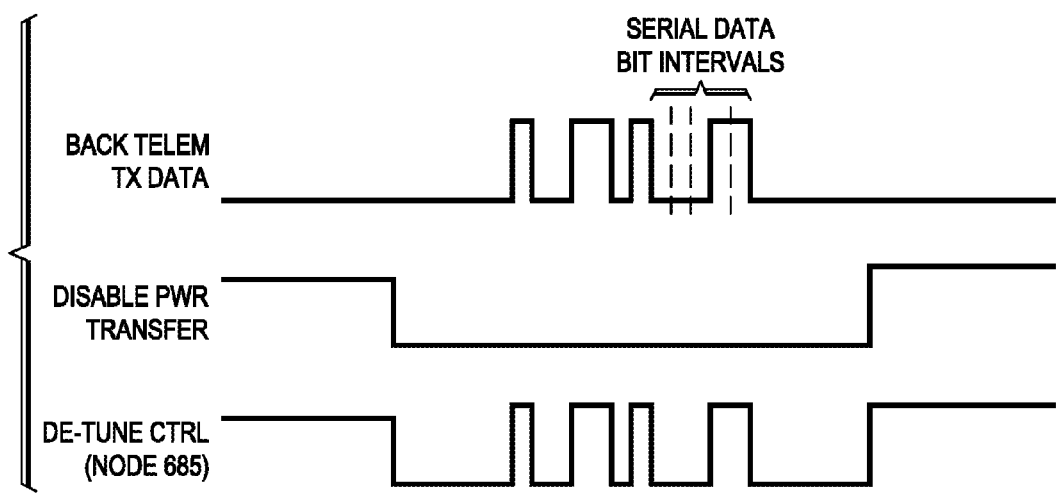
FIG. 13B illustrates voltage waveforms of selected signals depicted in the embodiment shown in FIG. 13A.
Figure 13A:
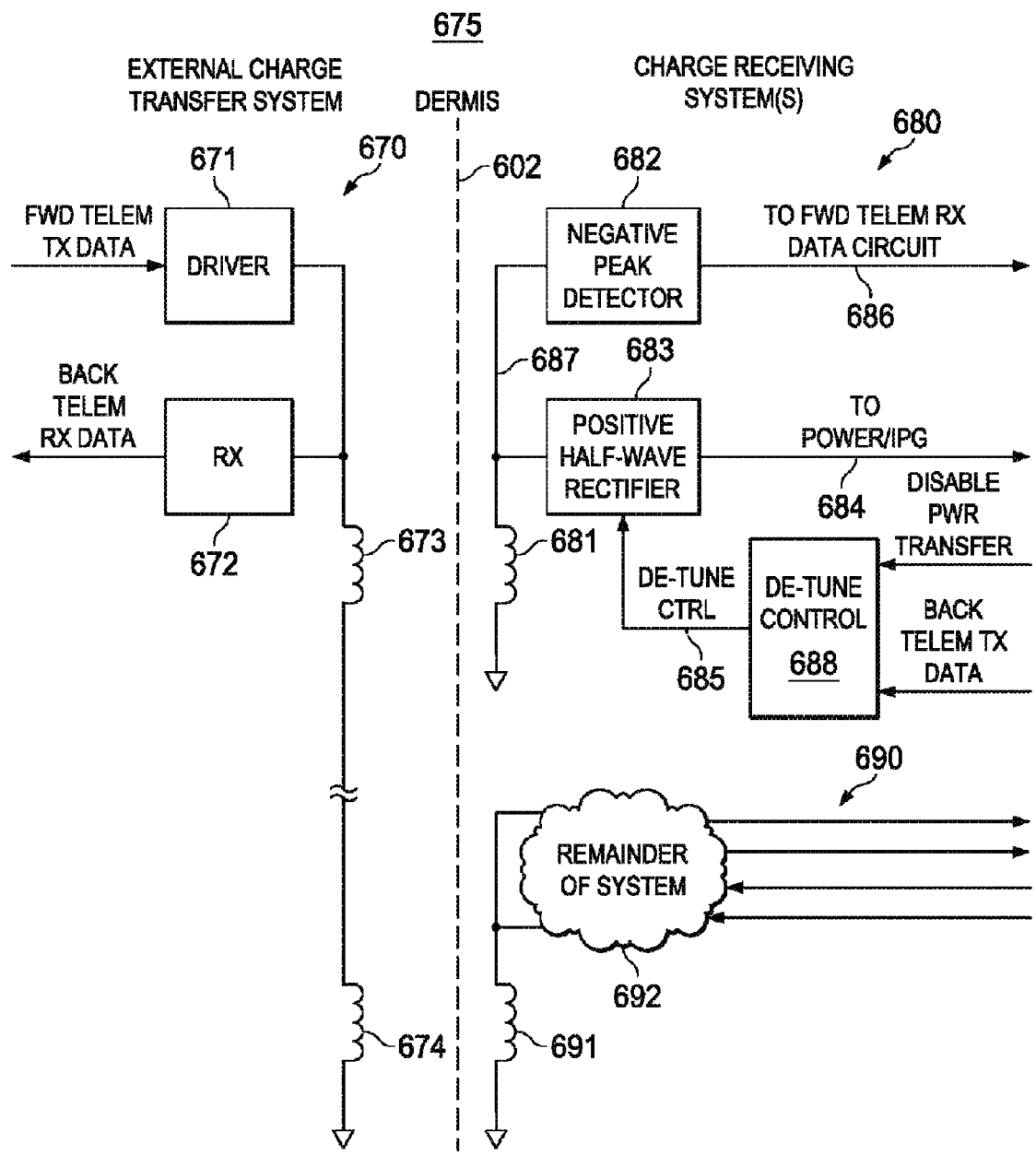
FIG. 13A is a block diagram of a system which provides for bi-directional communication with an implanted device, and particularly illustrates passive communication from an implanted device (back telemetry) when the receive coil is de-tuned, in accordance with some embodiments of the invention.

FIG. 13A is a block diagram of a system 675 which provides for bi-directional communication with an IPG, and particularly illustrates passive communication from an implanted device to the external charge transfer system (i.e., back telemetry) when the receive coil within the implanted device is de-tuned.

Two charge receiving systems 680, 690 are shown, each disposed within a corresponding IPG. An external charge transfer system 670 disposed outside a dermis layer 602 includes series-connected charge transfer coils 673, 674, each of which corresponds to a respective one of receive coils 681, 691 of respective charge receiving systems 680, 690. As before, preferably each receive coil 681, 691 is tuned to the resonant frequency of the respective charge transfer coil 673, 674 within the external charge transfer system 670. In this embodiment, two such charge transfer coils 673, 674 are shown, one for each charge receiving system 680, 690, but other embodiments may utilize one charge transfer coil or another number of charge transfer coils noting that the charge transfer coils are for delivery of charge to the IPGs. Such charge delivery may be utilized to charge a supercapacitor within the IPG, and/or to power the IPG, particularly if such IPG does not include a supercapacitor.

The external charge transfer system 670 includes a driver 671 that is responsive to a forward telemetry transmit data signal FWD TELEM TX DATA. As described in the embodiment shown in FIG. 12, when the FWD TELEM TX DATA signal is driven to a first logic state (e.g., logic high), the driver 671 drives the series-connected charge transfer coils 673, 674 with an AC signal, and when the FWD TELEM TX DATA signal is driven to a second logic state (e.g., logic low), the driver 671 is disabled. In some embodiments, the driver 671 together with the series-connected charge transfer coils 673, 674 may be configured as a resonant amplifier. When such a resonant amplifier is disabled, the AC signal decays and eventually ceases. Such operation may be viewed as providing a 100% amplitude modulation of the AC signal driven onto the series-connected charge transfer coils 673, 674, which modulation is controlled by a bit-serial forward telemetry data signal that also functions as an enable/disable signal for the driver 671 (if held to the appropriate one of its two logic states). The external charge transfer system 670 also includes a receiver circuit 672 that is responsive to the AC signal on the series-coupled charge transfer coils 673, 674, and which generates accordingly a back telemetry receive data signal BACK TELEM RX DATA.

Within a first IPG, the charge receiving system 680 includes a receive coil 681 for receiving energy transferred from the associated charge transfer coil 673 when in close proximity thereto. The receive coil 681 is coupled to a positive half-wave rectifier block 683 for receiving energy and generating a rectified voltage on node 684, and responsive to a DE-TUNE signal on node 685, for de-tuning the receive coil 681 to inhibit transfer of energy from the associated charge transfer coil 673. The rectified voltage on node 684 is coupled to charge transfer circuitry within the first IPG (not shown). The receive coil 681 is also coupled via node 687 to a negative peak detector block 682 for receiving forward telemetry data and generating on node 686 a respective forward telemetry receive data signal, which is conveyed to forward telemetry receive data FWD TELEM RX DATA circuitry within the first IPG (not shown).

The charge receiving system 680 also includes a de-tune control block 688 for generating the DE-TUNE control signal on node 685 responsive to a disable power transfer signal DISABLE PWR TRANSFER, and further responsive to a bit-serial back telemetry transmit data signal BACK TELEM TX DATA. In operation, the DISABLE PWR TRANSFER signal may be asserted when charge transfer is complete or not desired, which asserts the DE-TUNE control signal to de-tune the receive coil 681 through the positive half-wave rectifier 683. In addition, during normal charge transfer the DE-TUNE control signal may be asserted for each bit-position of the bit-serial BACK TELEM TX DATA signal corresponding to one of its two data states. Since de-tuning the positive half-wave rectifier 683 in concert with the receive coil 681 inhibits energy transfer from the charge transfer coil 673 to the receive coil 681, the loading of charge transfer coil 673 is decreased. This decreased loading results in a higher peak current through the series-connected charge transfer coils 673, 674. In the external charge transfer system 670, the receiver circuit 672 senses the change in peak current through the series-coupled charge transfer coils 673, 674 as each serial data bit of the BACK TELEM TX DATA signal either tunes or de-tunes the receive coil 681, and generates accordingly a back telemetry receive data signal BACK TELEM RX DATA.

If the DE-TUNE control signal is already asserted (e.g., because the DISABLE PWR TRANSFER signal is asserted to indicate charge transfer is complete or not desired) when the charge receiving system 680 desires to transmit back telemetry data, the DISABLE PWR TRANSFER signal may be briefly de-asserted to allow the BACK TELEM TX DATA signal to control the DE-TUNE control signal, as is shown in FIG. 13B. Thus, the charge receiving system 680 may still transmit back telemetry information irrespective of whether it is generally in a de-tuned state.

Within a second IPG, the charge receiving system 690 includes a receive coil 691 for receiving energy transferred from the associated charge transfer coil 674 when in close proximity thereto. The remainder 692 of the charge receiving system 690 is identical to the charge receiving system 680, and need not be separately described.

Figure 14A:
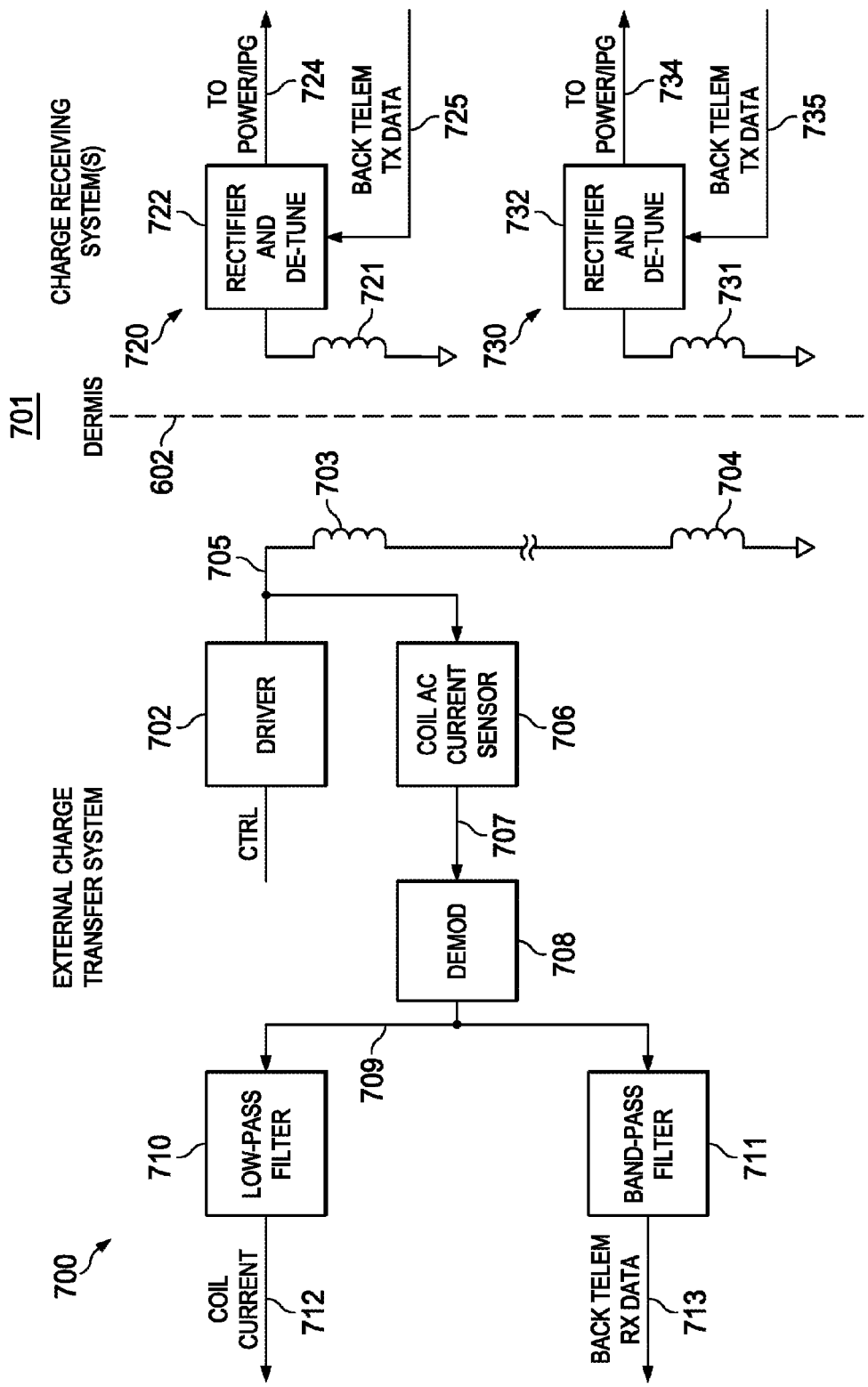
FIG. 14A is a block diagram of a system which includes charge transfer coil (or "transmit coil") current sensing circuitry to determine back telemetry data received from an implanted device, and to determine de-tuning of an implanted device coil, in accordance with some embodiments of the invention.

FIG. 14A is a block diagram of a system 701 which includes charge transfer coil ("transmit coil") current sensing circuitry, and particularly illustrates sensing such transmit coil current to determine back telemetry data received from an implanted device, and to determine de-tuning of an implanted device receive coil. Two charge receiving systems 720, 730 are shown, each disposed within a corresponding body-implanted active device. An external charge transfer system 700 disposed outside a dermis layer (or "dermal layer") 602 includes series-connected charge transfer coils 703, 704, each of which corresponds to a respective one of receive coils 721, 731 of respective charge receiving systems 720, 730. Although two such charge transfer coils 703, 704 are shown, one for each charge receiving system 720, 730, other embodiments may utilize one charge transfer coil or another number of charge transfer coils, depending upon the number of IPGs.

The external charge transfer system 700 includes a driver 702, responsive to a CTRL signal, for driving the series-connected charge transfer coils 703, 704 with an AC signal. Within the first IPG, the charge receiving system 720 includes a receive coil 721 that is preferably tuned to the resonant frequency of the associated charge transfer coil 703 within the external charge transfer system 700, so that receive coil 721 may receive energy transferred from the charge transfer coil 703 when in close proximity thereto. The receive coil 721 is coupled to a rectifier/de-tune block 722 for receiving energy at times and generating a rectified output voltage on node 724, and for de-tuning the receive coil 721 at other times, responsive to a respective BACK TELEM TX DATA signal on node 725, to inhibit transfer of energy from the charge transfer coil 703. The rectified voltage on node 724 is coupled to charge transfer circuitry within the first IPG (not shown). In this embodiment the BACK TELEM TX DATA signal functions as both a bit-serial data signal and a "disable charge transfer" signal, much like the DE-TUNE signal in the previous embodiment. In order to de-tune the receive coil 721 and disable charge transfer, the BACK TELEM TX DATA signal is driven and held in one of its two logic levels (e.g., a logic high level), while to actually communicate back telemetry data to the external charge transfer system 700, the BACK TELEM TX DATA signal is driven between both its logic levels according to the bit serial data. Any of several encoding formats may be used, but NRZ ("non-return-to-zero") encoding is assumed here.

Within the second IPG, the charge receiving system 730 includes a receive coil 731 that is preferably tuned to the resonant frequency of the associated charge transfer coil 704 within the external charge transfer system 700, so that receive coil 731 may receive energy transferred from the charge transfer coil 704 when in close proximity thereto. The receive coil 731 is coupled to a rectifier/de-tune block 732 for receiving energy at times and generating a rectified output voltage on node 734, and for de-tuning the receive coil 731 at other times, responsive to a respective BACK TELEM TX DATA signal on node 735, to inhibit transfer of energy from the charge transfer coil 704. The rectified voltage on node 734 is coupled to charge transfer circuitry within the second IPG (not shown).

The external charge transfer system 700 includes circuitry to generate a COIL CURRENT signal corresponding to the magnitude of the charge transfer coil current, and to generate a BACK TELEM RX DATA signal corresponding to the back telemetry data received from one of the charge receiving systems 720, 730. The back telemetry data is communicated passively by a given one of the charge receiving systems 720, 730 by modulating the amount of energy transferred from the external charge transfer coils and received by a given charge receiving system. Such modulation occurs by changing whether the corresponding receive coil is tuned or de-tuned. De-tuning the receive coil may occur when charge transfer is complete or not desired, in which case the transferred energy will decrease and remain at the decreased value, but may also occur in response to a bit-serial BACK TELEM TX DATA signal, in which case the variations or changes in transferred energy will have a frequency component matching the bit rate of the BACK TELEM TX DATA signal. The back telemetry data is received by the external charge transfer system by sensing the variation in charge transfer coil current that corresponds to changes in the amount of energy transferred to the given charge receiving system.

In this embodiment, the circuitry to accomplish this includes a charge transfer coil AC current sensor 706 having an input coupled to the output node 705 of driver 702, which generates on its output node 707 an AC voltage signal corresponding to the instantaneous current through the series-connected charge transfer coils 703, 704. This AC voltage signal on node 707 is coupled to a demodulator 708 which generates on its output node 709 a demodulated signal corresponding to the peak value of the AC voltage signal on node 707, which corresponds to the peak value of the instantaneous current through the charge transfer coils 703, 704. This demodulated signal on node 709 is filtered by low-pass filter 710 to generate the COIL CURRENT signal on node 712. The COIL CURRENT signal is a generally DC-like signal that is reflective of the low-frequency changes in the peak charge transfer coil current, such as would occur when charge transfer is no longer desired and its corresponding receive coil is de-tuned and remains de-tuned for some time.

Figure 14B:
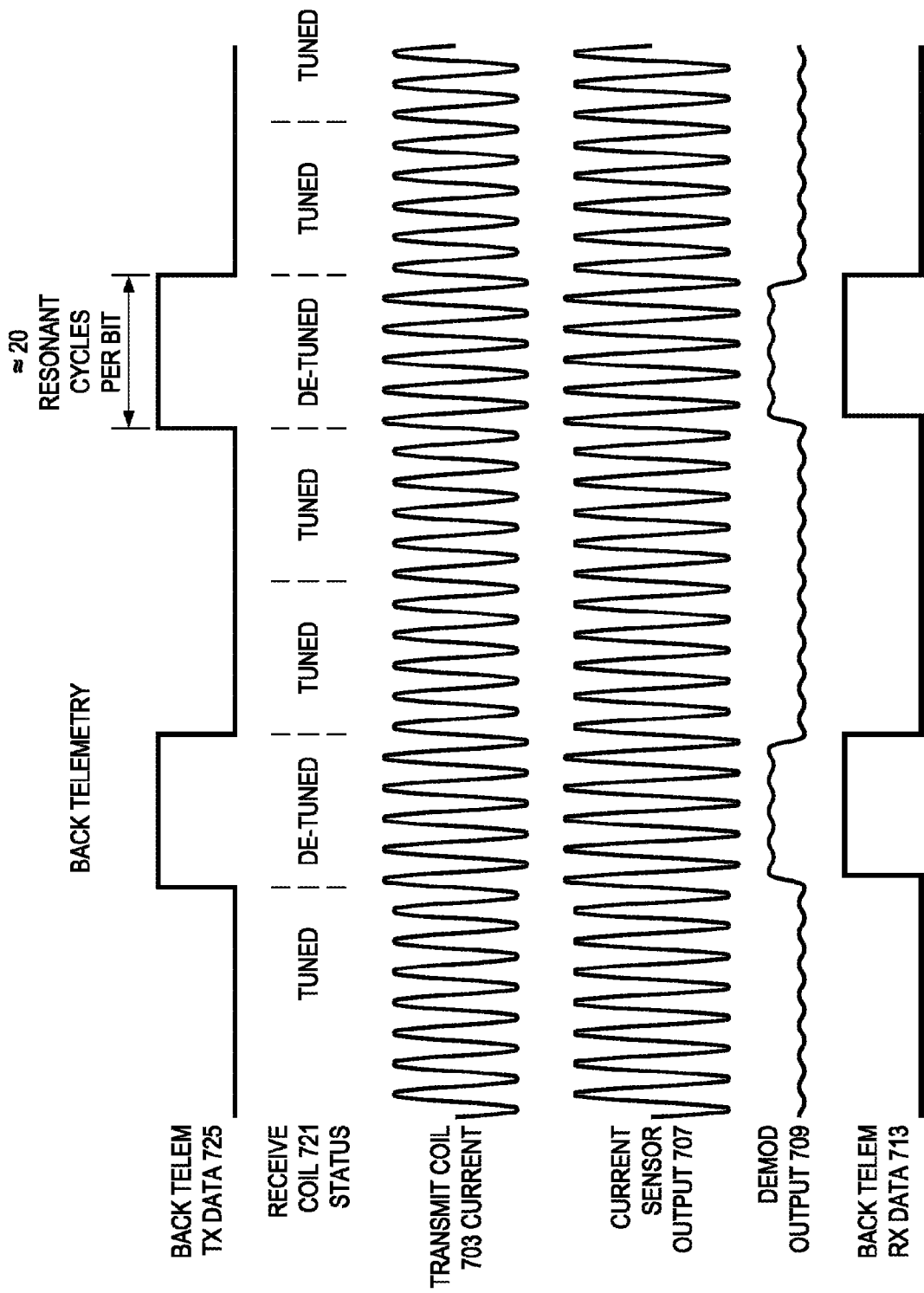
FIG. 14B illustrates voltage waveforms of selected signals depicted in the embodiment shown in FIG. 14A.

The demodulated signal on node 709 is also coupled to a band-pass filter 711 to generate the BACK TELEM RX DATA signal on node 713. This BACK TELEM RX DATA signal is reflective of higher-frequency changes in the peak charge transfer coil current, such as would occur when back telemetry data is being communicated and the corresponding receive coil is de-tuned and tuned responsive to the bit-serial BACK TELEM TX DATA signal. Illustrative waveforms of these signals are shown in FIG. 14B. In some embodiments the data rate for the back telemetry need not be identical to the data rate for the forward telemetry. For example, the back telemetry data rate, relative to the resonant frequency of the charge transfer coils in the external charge transfer system, may be result in each bit interval (i.e. bit position) corresponding to as few as 20 cycles of the resonant amplifier, as noted in FIG. 14B. Additional examples and other embodiments of such current sensing and receive data circuits are described below.

As noted above, FIG. 14B shows waveforms of selected signals illustrating back telemetry operation in the embodiment shown in FIG. 14A. In particular, the bit-serial BACK TELEM TX DATA signal (node 725) is shown representing several bits of information to be communicated from the charge receiving system 720 to the external charge transfer system 700, along with the corresponding tuned or de-tuned status of the receive coil 721. The peak current through the charge transfer coil 703 is higher corresponding to the de-tuned state of the receive coil 721. A voltage signal is generated at the output 707 of the current sensor 706, which voltage signal corresponds to the instantaneous current through the charge transfer coil 703. This output signal 707 is demodulated to produce the demodulated output signal on node 709, which is then filtered by band-pass filter 711 to produce the BACK TELEM RX DATA signal on node 713.

Figure 15:
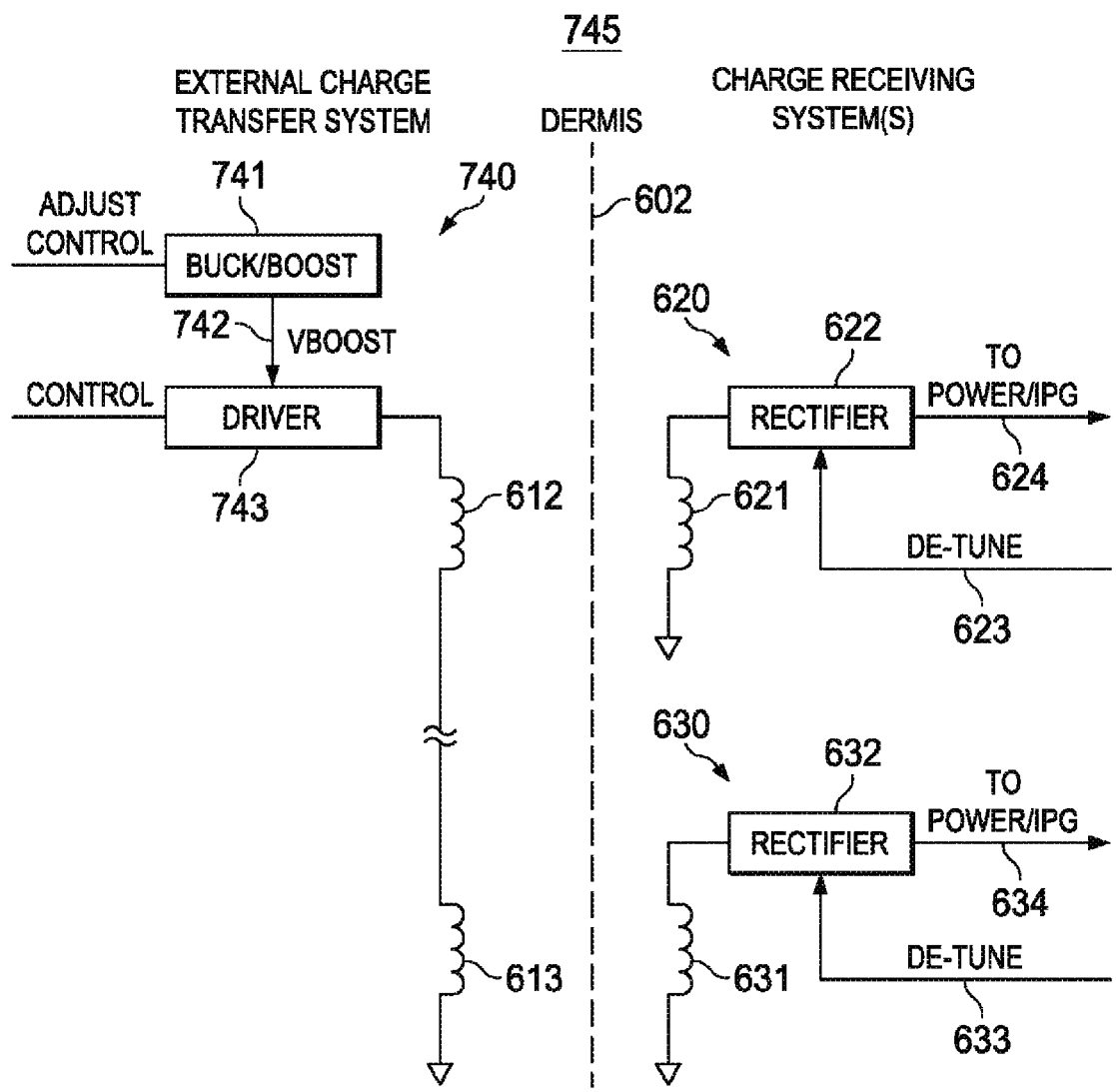
FIG. 15 is a block diagram of a system which provides for adjustable transmitted power to improve power efficiency within an implanted device, in accordance with some embodiments of the invention.

FIG. 15 is a block diagram of an exemplary charge transfer system 745 which provides for adjustable transmitted power to improve power efficiency within an implanted device. Two charge receiving systems 620, 630 are shown, each disposed within a corresponding IPG, which are identical to those described in FIG. 11, and need not be described here. An external charge transfer system 740 disposed outside a dermis layer 602 includes series-connected charge transfer coils 612, 613, each of which corresponds to a respective one of receive coils 621, 631 of respective charge receiving systems 620, 630. Two such charge transfer coils 612, 613 are shown, one for each charge receiving system 620, 630, but other embodiments may utilize one charge transfer coil or another number of charge transfer coils, depending upon the number of IPGs.

The external charge transfer system 740 includes a resonant driver 743 for driving the series-connected charge transfer coils 612, 613 with an AC signal, and a buck/boost circuit 741 that provides on node 742 a variable DC voltage for use by the driver 743 as an upper power supply node. By varying this VBOOST voltage on node 742, the amount of energy stored each resonant cycle in the charge transfer coils and ultimately transferred to the corresponding receive coil may be varied, for example, to achieve better charge delivery efficiency and coupling within the implanted device. The resonant driver 743 is responsive to a CTRL signal, such as described above regarding other embodiments, which may function as both a data signal and as an enable signal.

The VBOOST voltage on node 742 may be varied as charge transfer progresses (or the charge delivery requirements change) within each IPG. For example, during an early phase of charge transfer when the voltage is relatively low, it may be desirable to limit the rectified voltage on node 624 so that any voltage drop across the charge transfer circuit within the IPG is kept to a minimum necessary to achieve proper voltage regulation, or to provide a particular constant magnitude of charge transfer current to efficiently charge the supercapacitor. Later, as charge transfer progresses and the delivered voltage is raised to a higher voltage, the rectified voltage on node 624 may be increased to maintain a desired voltage drop across such charge transfer circuitry or to maintain the desired charge transfer current. When one of the IPGs is fully charged and its receive coil (e.g., 621) is de-tuned, the other IPG may still be transferring charge and its receive coil (e.g., 631) still tuned for resonant energy transfer from the external charge system. The VBOOST voltage may then be adjusted to optimize the amount of energy transfer into the remaining IPG.

The buck/boost circuit 741 is shown as being responsive to an ADJUST CTRL signal, which may be controlled within the external charge transfer system in response to detecting a decrease in energy transfer to one or more IPGs (e.g., using the COIL CURRENT signal described above), by receiving back telemetry information from one or both IPGs regarding internal voltage levels, internal current levels, and/or internal temperatures, or by one or more temperature sensors within the external charge transfer system (e.g., a sensor placed near each charge transfer coil), or by any other useful means, such as information from one or both IPGs conveyed using a Bluetooth connection to the external charge transfer system. This adjustability of the VBOOST voltage provides for adjustable control of the energy coupled to one or both of the charge receiving systems within the IPGs, even though both series-connected charge transfer coils 612, 613 are driven by a single driver circuit 743. However, it should be noted that changing of the amount of energy that can be coupled to any of the IPGs will change the amount of energy transfer to all the IPGs. Thus, although not disclosed herein, the IPGs must operate such that charge delivered is governed by the one of the IPGs that requires the most charge transfer. Each of the IPGs, for example, will send information back to the external charge delivery system in the form of a request to indicate an increased need for charge and the amount of charge transfer will be increased until the IPG requiring the most charge has that request satisfied.

Figure 16A:
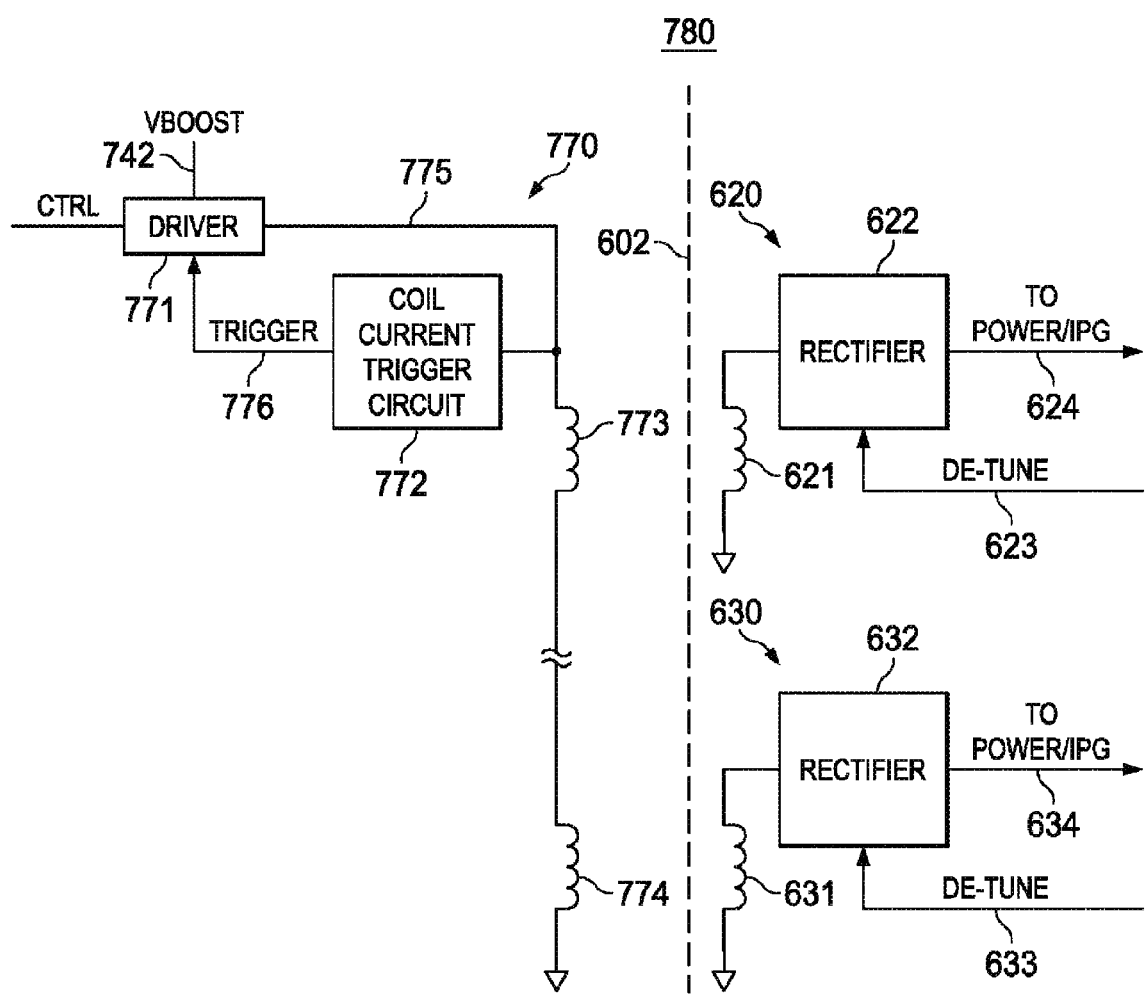
FIG. 16A is a block diagram of a system which includes feedback excitation control of a resonant coil driver amplifier, in accordance with some embodiments of the invention.

FIG. 16A is a block diagram of an exemplary system 780 which includes feedback excitation control of a resonant coil driver amplifier. Two charge receiving systems 620, 630 are shown, each disposed within a corresponding IPG, which are identical to those described in FIG. 11, and need not be described here. An external charge transfer system 770 disposed outside a dermis layer 602 includes series-connected charge transfer coils 773, 774, each of which corresponds to a respective one of receive coils 621, 631 of respective charge receiving systems 620, 630. While two such charge transfer coils 773, 774 are shown, one for each charge receiving system 620, 630, other embodiments may utilize one charge transfer coil or another number of charge transfer coils, depending upon the number of IPGs.

Figure 16B:
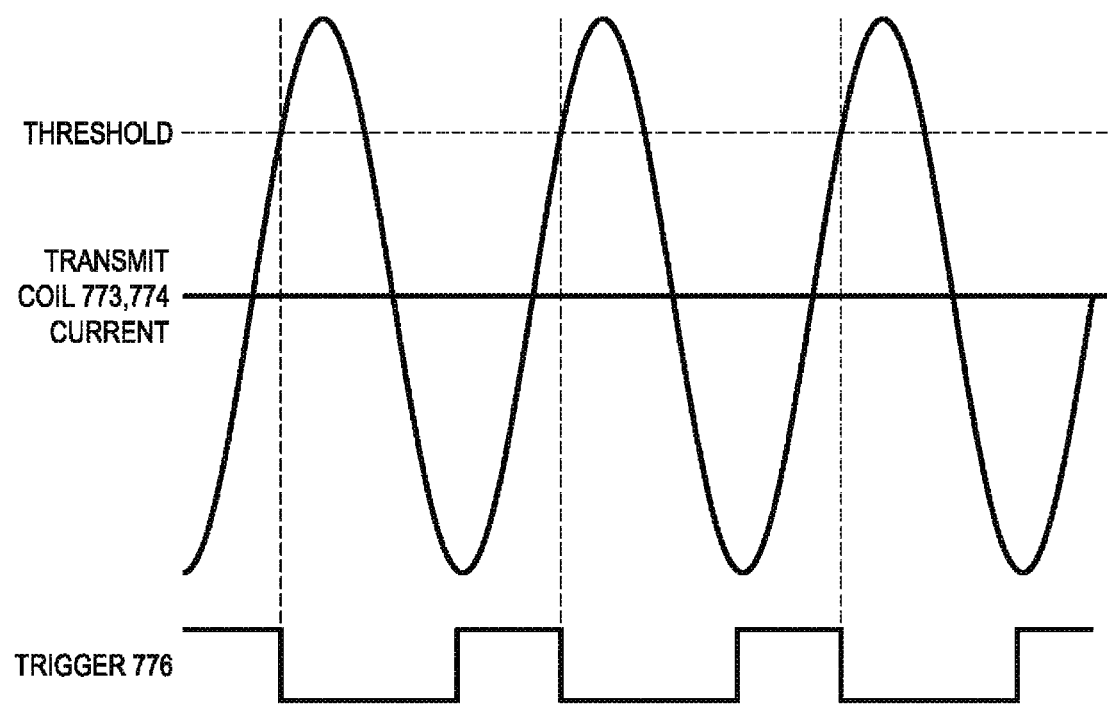
FIG. 16B illustrates voltage waveforms of selected signals depicted in the embodiment shown in FIG. 16A.

The external charge transfer system 770 includes a resonant driver 771 for driving the series-connected charge transfer coils 773, 774 with an AC signal. An adjustable VBOOST voltage is conveyed on node 742 to provide a variable DC voltage for use by the driver 771 as an upper power supply node. The resonant driver 771 is responsive to a CTRL signal, such as described above, which may enable/disable the driver 771 when appropriate (e.g., after charge transfer is complete within both IPGs), and may also convey forward telemetry information to one or both IPGs, both as described above. The external charge transfer system 770 also includes a coil current trigger circuit 772 for generating on node 776 a TRIGGER signal conveyed to the resonant driver 771 to provide a periodic "excitation" signal to periodically pump additional energy into the resonant driver 771, which is helpful to maintain a high degree of efficiency of the resonant operation of the driver 771 in concert with the series-connected charge transfer coils 773, 774 connected to the output node 775 of the resonant driver 771. The coil current trigger circuit 772 preferably is configured to assert the TRIGGER signal when the instantaneous charge transfer coil current, during each resonant cycle, crosses a predetermined threshold that is proportional to the peak instantaneous charge transfer coil current. In other words, when the instantaneous charge transfer coil current crosses a value that is a predetermined percentage of the maximum current (e.g., 60% of peak current), the TRIGGER signal is asserted to pump the additional energy into the resonant amplifier (i.e., driver 771 and transmit coils 773, 774). Illustrative waveforms of the instantaneous charge transfer coil current and the TRIGGER signal are shown in FIG. 16B.

By generating a feedback-controlled TRIGGER signal in this manner, high efficiency resonant operation may be achieved even as the charge transfer coil current may vary. Such variation in charge transfer coil current may result from changes in the VBOOST voltage, from changes in transferred energy due to receive coil de-tuning within an associated charge receiving system, from forward telemetry which modulates the charge transfer coil (i.e., "transmit coil") current, from variations in component parameters, and from changes in voltage, temperature, or other environmental conditions.

M. Headset Charge Transfer System

Figure 17:
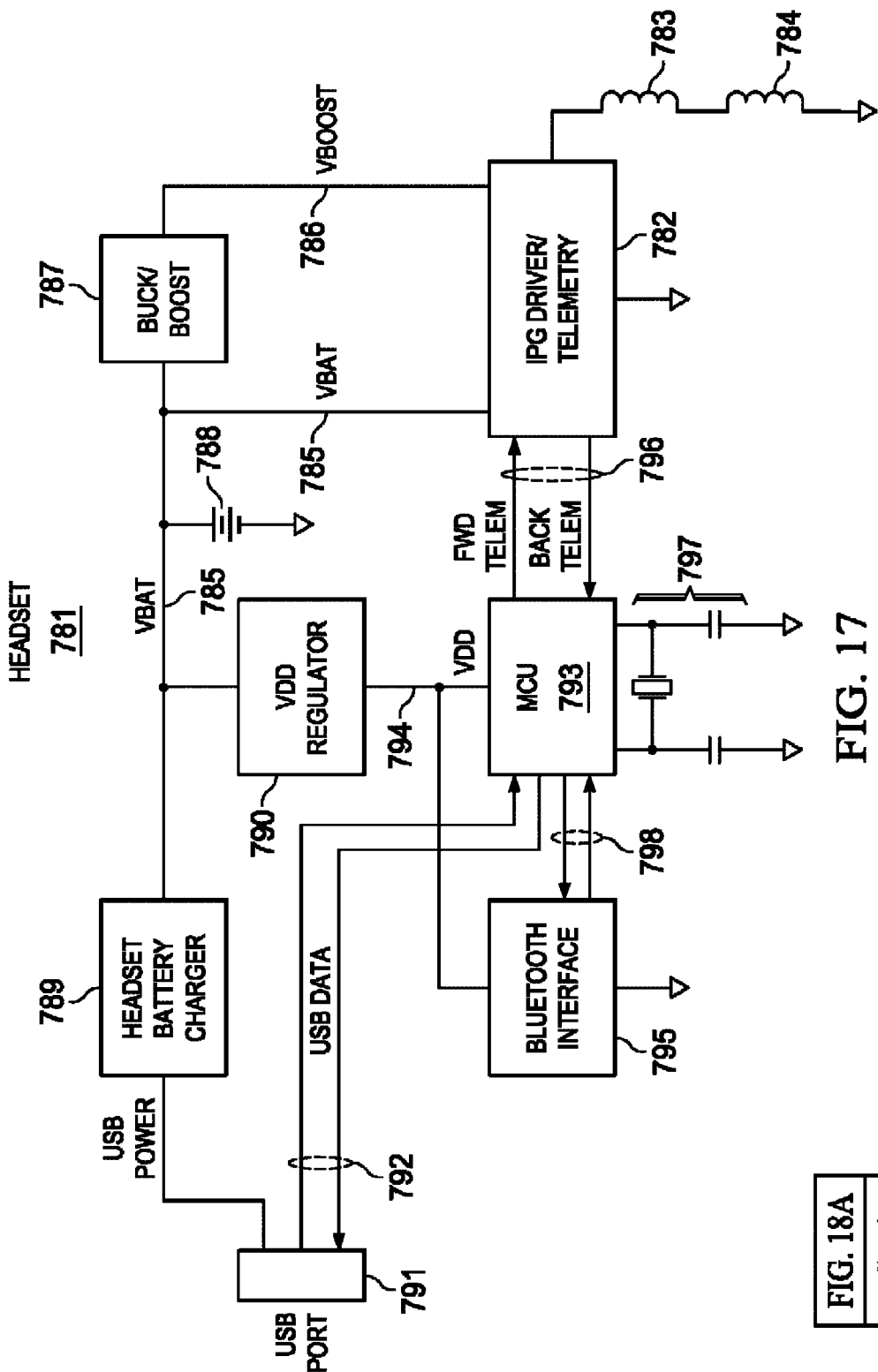
FIG. 17 is a block diagram of a headset that includes an external charge transfer system for two implanted devices, in accordance with some embodiments of the invention.

FIG. 17 is a block diagram of an exemplary headset 781 that includes an external charge transfer system for two head-located IPGs, such as two implantable pulse generator (IPG) devices. The headset includes an IPG Driver and Telemetry block 782 that drives two charge transfer coils 783, 784, and which is powered by a battery voltage VBAT conveyed on node 785 by headset battery 788, and an adjustable voltage VBOOST conveyed on node 786. A buck/boost circuit 787 receives the VBAT voltage on node 785 and generates the VBOOST voltage on node 786. Power transfer is provided by a Headset Battery Charger 789 which receives USB power from USB port 791. A VDD regulator 790 also receives the VBAT voltage on node 785 and generates a VDD voltage (e.g., regulated to 3.0 volts) on node 794, which is generally used as a power supply voltage for certain circuitry within the headset.

A microcontroller (MCU) 793 provides general configuration control and intelligence for the headset 781, and communicates with the IPG Driver and Telemetry block 782 via a forward telemetry signal FWD TELEM and a back telemetry signal BACK TELEM via a pair of data lines 796. The MCU 793 can also communicate with an external device (e.g., a smartphone or personal digital assistant (PDA), a controller, a diagnostic tester, a programmer) that is connected to the USB port 791 via a pair of USB data lines 792. The MCU 793 is connected to an external crystal resonant tank circuit 797 for providing an accurate timing source to coordinate its various circuitry and data communication interfaces. A Bluetooth interface 795 provides wireless interface capability to an external device, such as a smartphone or other host controller, and is connected to the VDD voltage on node 794. The Bluetooth interface 795 communicates with the MCU 793 using data/control signals 798. In general, MCU 793 is utilized to store configuration information in an on-chip Flash memory for both the overall headset and charge transfer system and also provide configuration information that can be transferred to one or more of the IPGs. The overall operation of the headset is that of a state machine, wherein the IPG driver/telemetry block 782 and the other surrounding circuitry, such as the buck/boost circuit 787 and the headset battery charger 789, all function as state machines, typically implemented within an ASIC. Thus, when communication information is received that requires the MCU 793 to transfer configuration information to the IPG or, alternatively, to configure the headset state machine, the MCU 793 will be activated. In this embodiment a state machine is utilized for most functionality because it has a lower power operation, whereas an instruction-based processor, such as the MCU 793, requires more power. It should be understood, however, that such a headset can utilize any type of processor, state machine or combinatorial logic device.

Figure 18A:
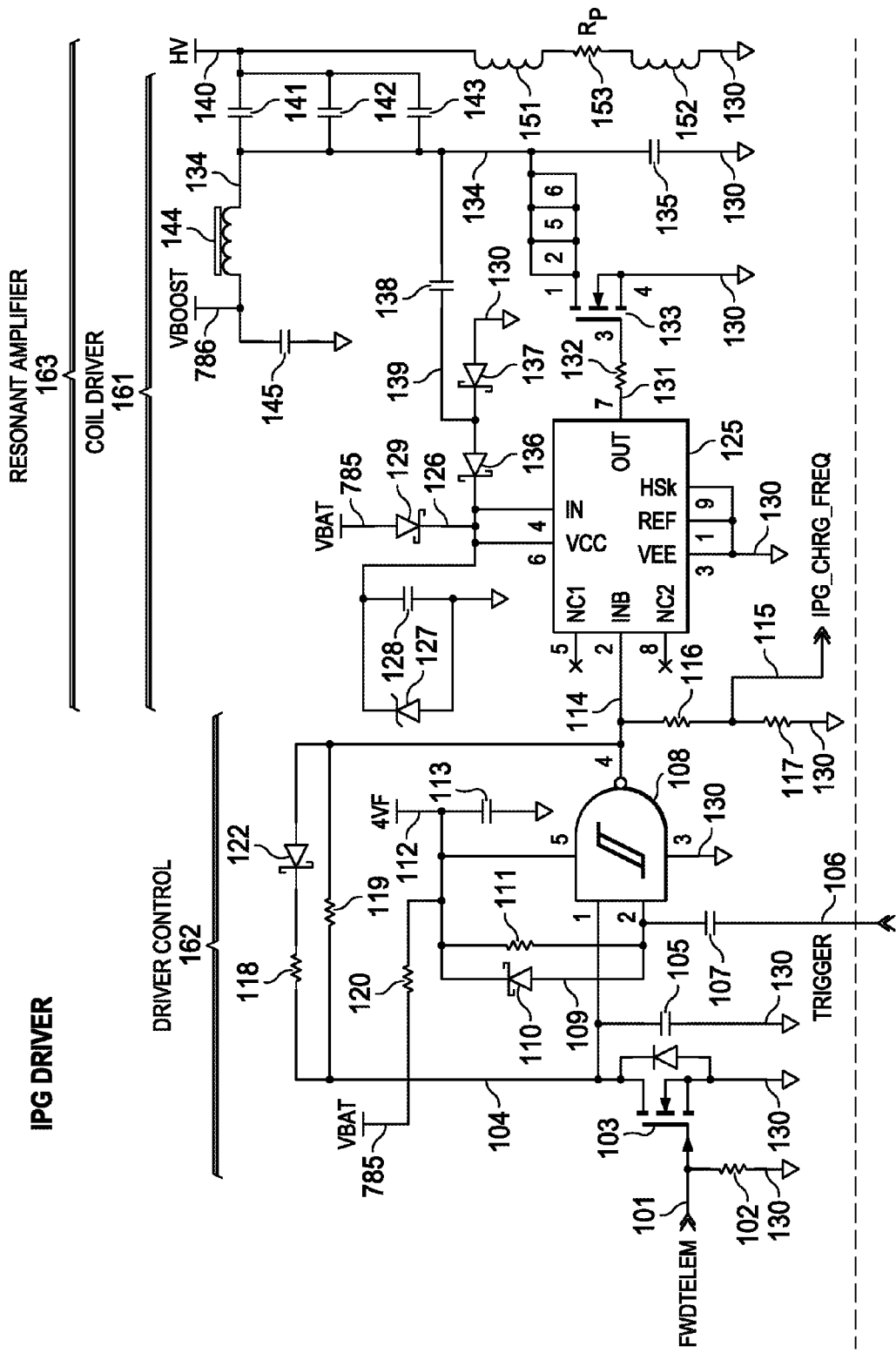
FIGS. 18A and 18B, is a schematic diagram of an exemplary IPG driver and telemetry circuitry block, such as that shown in FIG. 17, in accordance with some embodiments of the invention.
Figure 18B:
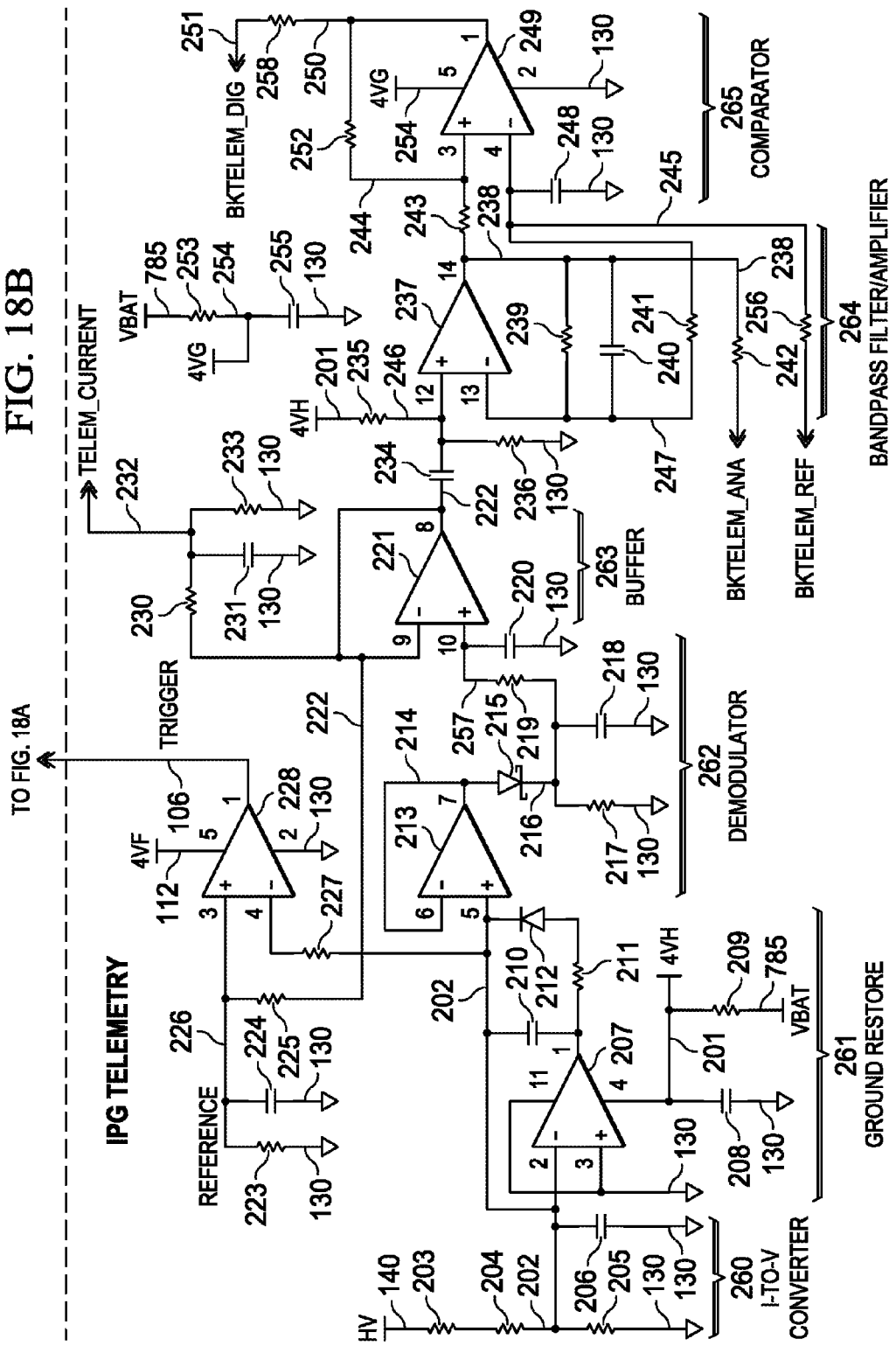

FIG. 18, which includes FIGS. 18A and 18B, is a schematic diagram of an exemplary IPG driver and IPG telemetry circuit, such as the IPG Driver and Telemetry block 782 shown in FIG. 17. While these FIGS. 18A and 18B each represent a portion of the complete FIG. 18 and may be arranged next to each other (aligned at the dotted line on each figure) to view the entire FIG. 18, the portion shown on FIG. 18A may be generally referred to as the IPG driver circuit, even though certain portions of the IPG driver circuit is shown in FIG. 18B, and the portion shown on FIG. 18B may be generally referred to as the IPG telemetry circuit, even though certain portions of the IPG telemetry circuit is shown in FIG. 18A.

Referring now to the complete FIG. 18, a portion of a charge transfer system is depicted which includes a coil driver 161 for a pair of series-connected charge transfer coils 151, 152, and a driver control circuit 162 for the coil driver 161. The coil driver 161 together with the charge transfer coils 151, 152 may be viewed as a resonant amplifier circuit 163. The driver control circuit 162 provides a control signal on node 114 that serves to turn off the coil driver 161 at times, and to periodically cause energy to be pumped into the resonant amplifier 163 at other times, as will be explained below.

Figure 19A:
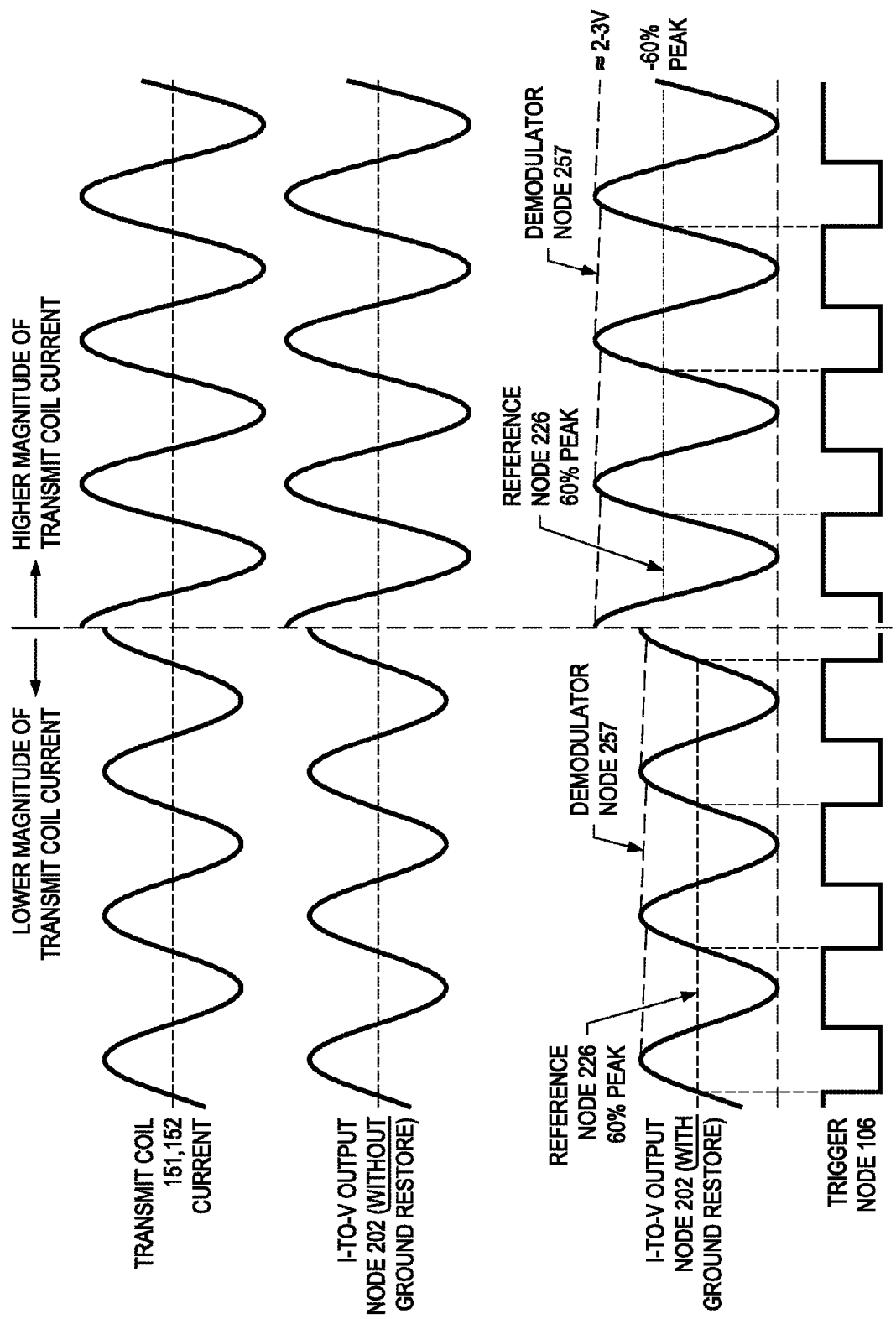
FIGS. 19A, 19B, and 19C illustrate voltage waveforms of selected signals depicted in the embodiment shown in FIG. 18 and FIG. 23A.
Figure 19B:
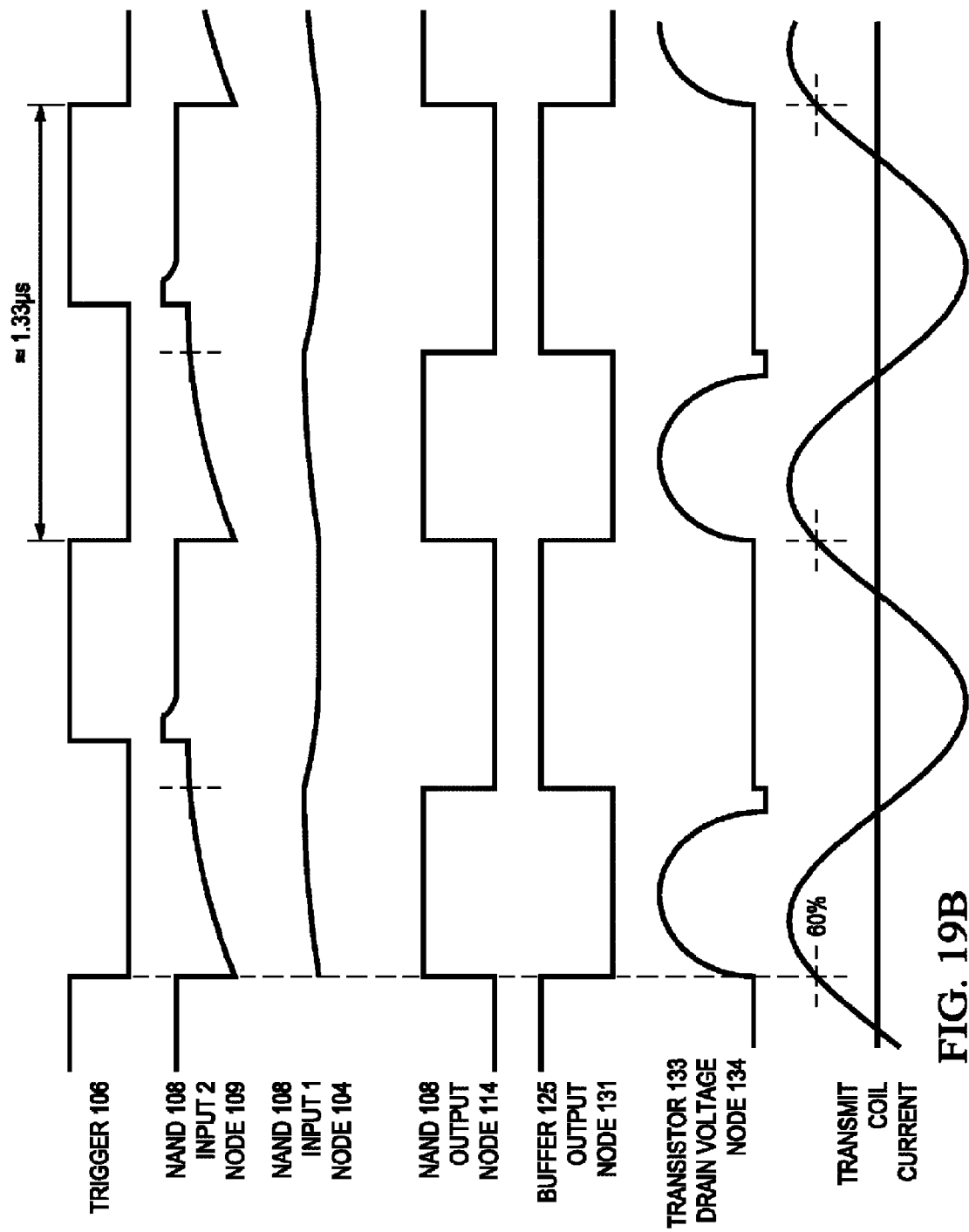
Figure 19C:
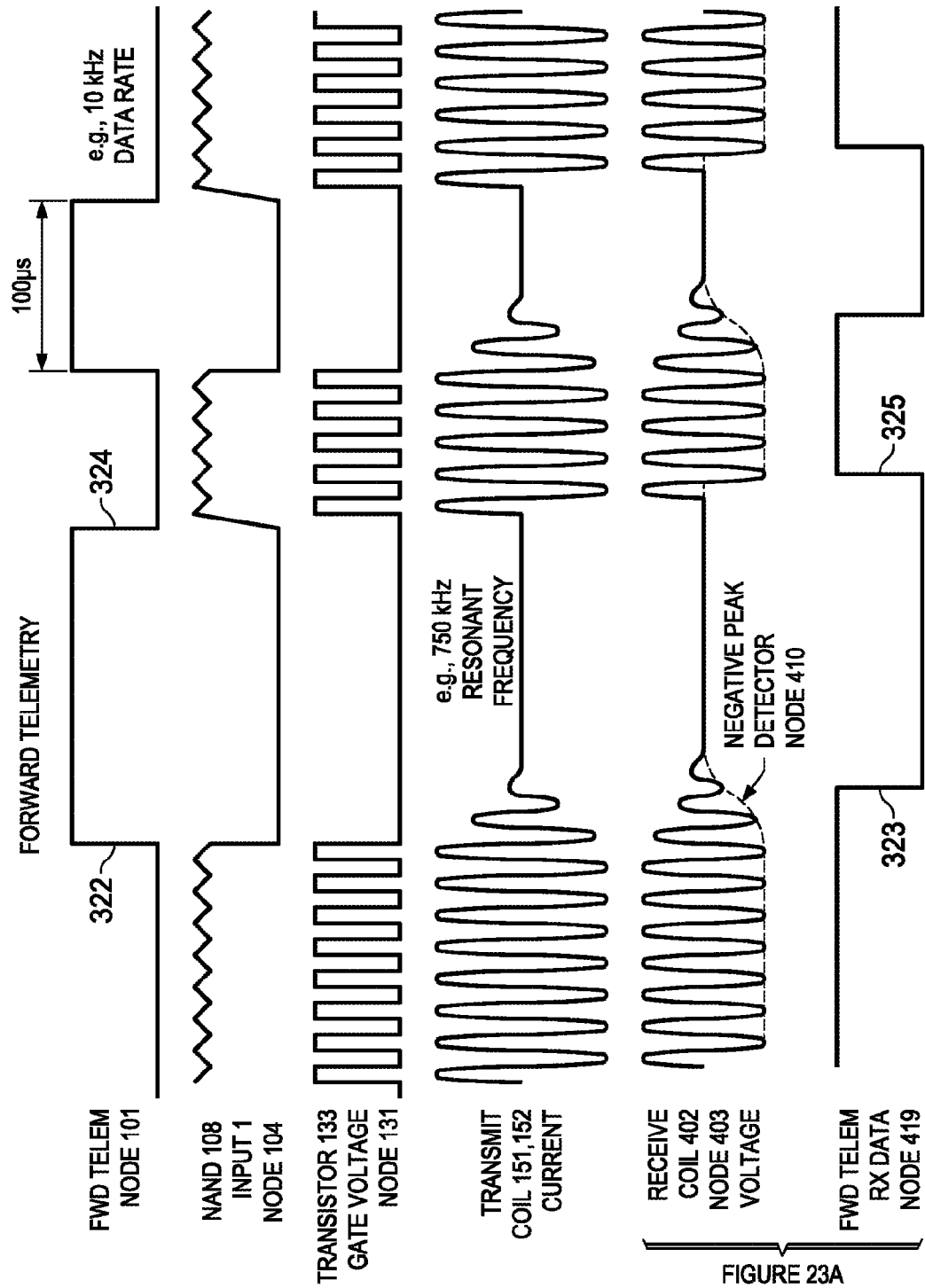

The coil driver 161 may be understood by looking first at excitation coil 144 and driver transistor 133. In resonant operation, the driver transistor 133 is periodically turned on, which drives the voltage of node 134 to ground (labeled 130). Since the excitation coil 144 is connected between node 786, which conveys a VBOOST voltage, and node 134, which is now grounded by transistor 133, the VBOOST voltage is impressed across the excitation coil 144 and consequently a current flows through the excitation coil 144, which current stores energy in the excitation coil 144. The magnitude of the VBOOST voltage may be varied (e.g., between 1.0 and 5.5 volts) to vary the amount of energy stored in the excitation coil 144 per cycle, to thus vary the amount of energy coupled to the receive coils (also referred to as "secondary coils"). Capacitor 145 provides local filtering for the VBOOST voltage conveyed on node 786. When the driver transistor 133 is then turned off, the energy in excitation coil 144 is "pumped" into the LC resonant circuit formed by parallel-connected capacitors 141, 142, 143 connected in series with the charge transfer coils 151, 152. Resistor 153 represents the parasitic resistance of the charge transfer coils 151, 152 and their associated wiring. Illustrative waveforms are shown in FIGS. 19A, 19B, and 19C. In certain embodiments, the resonant frequency is preferably on the order of 750 kHz.

Three separate capacitors 141, 142, 143 are used to distribute the peak current that would otherwise flow through the leads, solder joints, and structure of a single capacitor, to instead achieve a lower peak current through each of capacitors 141, 142, 143. But in understanding the operation of this circuit, these three capacitors 141, 142, 143 may be viewed as effectively providing a single resonant capacitor. When driver transistor 133 is turned on, it is desirable to drive node 134 to a voltage as close to ground as possible, to reduce losses that would otherwise result from a large drain-to-source current and a non-zero drain-to-source voltage across driver transistor 133. Consequently, the drain terminal of driver transistor 133 is connected by several distinct package pins to node 134.

Driver transistor 133 is controlled by the output 131 of buffer 125, which is coupled to the gate of driver transistor 133 through resistor 132. The buffer 125 is connected to operate as an inverting buffer since the non-inverting input IN (pin 4) is connected to VCC (pin 6), and the inverting input INB (pin 2) is utilized as the buffer input that is connected to node 114, which is the control signal generated by driver control circuit 162. Thus, when node 114 is low, the output node 131 of buffer 125 is high, and driver transistor 133 is turned on. The output node 131 is coupled to the gate of driver transistor 133 through resistor 132 to limit the peak current charging and discharging the gate terminal of driver transistor 133, and to also provide (together with the parasitic gate capacitance of driver transistor 133) an RC filter for the signal actually coupled to the gate terminal of driver transistor 133.

As mentioned above, when driver transistor 133 is turned on, it is desirable for node 134 to be driven to a voltage as close to ground as possible. To help achieve this, it may be likewise desirable to drive the gate terminal of driver transistor 133 to a voltage higher than the battery voltage VBAT conveyed on node 785. To accomplish this, a local power circuit including diodes 127, 129, 136, 137, and capacitors 128, 138, may be utilized.

During circuit startup, the buffer circuit 125 operates with its "VCC voltage" (conveyed on local power node 126) essentially at the battery voltage VBAT, less a small diode drop through diode 129. The VBAT voltage may be 3.5-4.0 volts, which is sufficient to operate the buffer 125 to provide adequate output voltage levels on node 131 to sufficiently turn on/off driver transistor 133 to initiate and maintain resonant operation. In such resonant operation, driver transistor 133 is preferably turned off at a particular time in each resonant cycle to pump energy into the resonant circuit, as will be explained further below. Each time that the driver transistor 133 is turned off, the voltage on node 134 rises quickly as the current through excitation coil 144 continues to flow into node 134 and charges capacitor 135. This rising voltage is coupled through capacitor 138 onto node 139, through diode 136, and onto the local power node 126 for buffer 125. The magnitude of the positive-transition of the voltage on node 134 results in a voltage on local power node 126 that may be as high as 8.0 volts, which is higher than the VBAT voltage, especially when operating in the lower range of battery voltage (e.g., as the battery discharges). When the voltage of local power node 126 rises above the VBAT voltage, diode 129 prevents any back-current into the VBAT node 785, and Zener diode 127 operates to limit, for safety reasons, the maximum voltage developed on local power node 126. Capacitor 128 provides local filtering on the local power node 126 irrespective of whether the buffer 125 is powered by the battery (through diode 129) or by resonant operation of the coil driver circuit 161 (through diode 136).

The driver control circuit 162 generates on output node 114 a driver control signal that controls when driver transistor 133 is turned on/off. In resonant operation, the driver control signal 114 is preferably a periodic signal that causes the driver transistor 133 to turn off at a predetermined time during each resonant cycle, and to turn back on at a later time during each resonant cycle, to thereby cause energy to be pumped into the resonant amplifier 163 during each resonant cycle. In addition, at certain times the driver control signal 114 is preferably driven high to cause the driver transistor 133 to turn off and remain off for a time duration longer than a resonant cycle, which prevents energy from being pumped into the resonant amplifier, and thus allows the resonant amplifier operation to decay and eventually cease.

The driver control circuit 162 includes a Schmitt-trigger NAND gate 108 having a local power supply node 112 (also labeled 4VF) which is coupled to the battery voltage VBAT using a small noise-isolation resistor 120 and a local filter capacitor 113. An input circuit includes capacitor 107, diode 110, and resistor 111, which together generate a first input signal on node 109 (NAND input pin 2) responsive to a TRIGGER signal conveyed on node 106. A feedback circuit includes diode 122, resistors 118, 119, and capacitor 105, which together generate a second input signal on node 104 (NAND input pin 1) responsive to the driver control signal generated on the output node 114.

To understand operation of the driver control circuit 162 during normal operation of the resonant amplifier circuit 163, assume that the TRIGGER signal 106 is high, both inputs of NAND 108 (nodes 104, 109) are high, and the output of NAND 108 (driver control signal 114) is low. Consequently, node 131 is high (due to inverting buffer 125) and driver transistor 133 is turned on, driving node 134 to ground and causing current to flow from VBOOST (node 786) through the excitation coil 144 to ground.

As will be explained in detail below, the TRIGGER signal on node 106 is then driven low, thus creating a falling-edge (i.e., negative transition) on the voltage of node 106. Capacitor 107 couples this negative transition to node 109, which is coupled to a voltage below the lower input threshold of Schmitt NAND gate 108. As a result, the output node 114 is driven high, node 131 is driven low, and transistor 133 is turned off. This happens almost immediately after the falling edge of the TRIGGER signal 106.

With the TRIGGER signal 106 still low, the resistor 111 will charge node 109 until its voltage reaches the upper input threshold of Schmitt NAND gate 108, at which time the NAND gate 108 output node 114 is again driven back low, node 131 is driven high, and transistor 133 is turned on. The values of resistor 111 and capacitor 107 are chosen, in concert with the upper and lower input thresholds of the Schmitt NAND gate 108, to determine the output high pulse width of output node 114, and thus determine the length of time that transistor 133 is turned off.

When the TRIGGER signal 106 is driven back high, this positive transition is coupled by capacitor 107 to node 109, but the coupled charge is snubbed by diode 110 to prevent an excessive positive voltage that would otherwise be generated at node 109, and instead maintain the voltage of node 109 at essentially the VBAT voltage.

If there are no transitions of the TRIGGER signal 106, the voltage of node 109 (NAND input pin 2) remains high, and the feedback circuit (diode 122, resistors 118, 119, and capacitor 105) causes the output node 114 to oscillate. This occurs because the voltage of node 104 (NAND input pin 1) slowly follows the voltage of the output node 114 due to the RC circuit formed by the feedback resistors 118, 119 (and diode 122) coupled between the output node 114 and input node 104, and the capacitor 105 coupled to node 104 itself. Diode 122 is included so that the parallel combination of resistors 118, 119 charges node 104 after a positive-going output transition, while only resistor 119 discharges node 104 after a negative-going output transition. This asymmetry helps keep node 104 nominally very close to the VBAT level during normal resonant operation, to essentially disable the "watchdog timer" aspect of this circuit as long as periodic TRIGGER signals are received.

The component values of resistors 118, 119 and capacitor 105 are preferably chosen so that the self-oscillation frequency of node 114 is much lower than the resonant frequency of operation (and likewise the expected frequency of the TRIGGER signal 106 during resonant operation, as will be explained in greater detail below). In some embodiments the self-oscillation frequency is approximately 3-4 times lower than the resonant frequency. This self-oscillation provides a suitable periodic conduction path through driver transistor 133 to initiate operation of the resonant amplifier 163 until the TRIGGER signal 106 is generated per cycle, which provides for more efficient operation and greater spectral purity of the resonant amplifier circuit 163. Resistors 116 and resistor 117 form a voltage divider to generate on node 115 an IPG_CHRG_FREQ signal reflective of the actual charger frequency.

A forward telemetry data signal FWDTELEM conveyed on node 101 is coupled to the gate terminal of NMOS transistor 103, which terminal is coupled to ground 130 by biasing resistor 102. The operation described thus-far above assumes that the FWDTELEM signal remains at ground, and thus transistor 103 remains turned off. If the FWDTELEM signal is driven high, NAND gate 108 input node 104 is driven to ground, which causes the NAND gate 108 output node 114 to be driven high, irrespective of the second NAND input node 109. This, of course, turns off driver transistor 133 for as long a time as FWDTELEM remains high, and causes resonant operation of the resonant amplifier circuit 163 to decay and eventually, if disabled for a long enough time, to cease entirely. Then, when the FWDTELEM signal is driven back low and transistor 103 turns off, the driver control circuit 162 begins to self-oscillate, thus starting operation of the resonant amplifier circuit 163 and the eventual generation of the TRIGGER signal 106 to more precisely control the timing of driver transistor 133. Such resonant "lock-in" occurs fairly quickly, usually in only 1-2 cycles. In some embodiments, the resonant frequency is approximately 750 kHz, and the forward data rate is approximately 10 kHz (i.e., a 100 μS bit interval), and the time required for the resonant amplifier 163 to decay (when FWDTELEM is driven high), and to re-start and lock-in resonant operation (when FWDTELEM is driven low), is a small portion of an individual bit interval. A more detailed description of such forward data transmission, including receiving such transmitted data in a charge receiving system, follows below.

As described above, in normal resonant operation the negative transition of the TRIGGER signal 106 determines when the driver transistor 133 is turned off during each resonant cycle of the amplifier circuit 163, and the RC input circuit on node 109 determines how long the driver transistor 133 remains off. Preferably the driver transistor 133 has a 30% duty cycle (i.e., turned off 30% of the time). In this implementation, feedback circuitry shown in FIG. 18B is utilized that generally tracks the actual current through the charge transfer coils 151, 153, and generates the negative-going transition of the TRIGGER signal 106 at a time during each resonant cycle when the increasing instantaneous charge transfer coil current exceeds a predetermined percentage of the peak current through the charge transfer coils 151, 152. Careful selection of the predetermined percentage improves the efficiency of resonant amplifier operation and reduces unwanted harmonic components of the oscillation frequency.

The generation of the TRIGGER signal 106 begins with a current-to-voltage converter circuit 260 formed by the series-connected resistors 203, 204 and capacitor 206 coupled between the HV node 140 (the same node driving the series-connected charge transfer coils 151, 152) and ground 130. Resistor 205 is a biasing resistor. With proper selection of component values, the instantaneous voltage generated at node 202 will be proportional to the instantaneous current through the charge transfer coils 151, 152. Such may be achieved by proper selection of the resistor and capacitor values in the current-to-voltage converter circuit 260 to achieve the same time constant as the inductor and parasitic resistor values in the charge transfer coils. Specifically, the values are preferably chosen so that R/C=L/R. Referencing the actual components, this relationship is then $(R_{203}+R_{204})/C_{206}=(L_{151}+L_{152})/Rp_{153}$ (e.g., where $R_{203}$ means the value of resistor 203). If this relationship is followed, the instantaneous voltage at node 202 is an AC voltage that is proportional to (i.e., corresponds to) the instantaneous AC current through the charge transfer coils 151, 152. Normally, this AC voltage on node 202 would be symmetric and centered around the ground voltage, as shown in FIG. 19A, but in this embodiment the AC voltage on node 202 is offset to a non-negative voltage range by a ground restore circuit 261.

The ground restore circuit 261 includes an amplifier 207 having a local power supply node 201 (also labeled 4VH) which is coupled to the battery voltage VBAT (conveyed on node 785) using a small noise-isolation resistor 209 and a local filter capacitor 208. The amplifier 207 non-inverting input (pin 3) is coupled to ground, and the inverting input (pin 2) is coupled to node 202. A feedback circuit includes capacitor 210, resistor 211, and diode 212. In operation, this ground restore circuit 261 translates the AC voltage signal on node 202 to a non-negative voltage signal of the same magnitude, whose peak low voltage is ground, and whose peak high voltage is twice that otherwise generated on node 202 in the absence of the ground restore circuit 261. This resulting waveform for node 202 is shown in FIG. 19A. The peak voltage at node 202 may be 2-3 V.

The signal on node 202 is coupled to a demodulator circuit 262 that includes amplifier 213, diode 215, resistors 217, 219, and capacitors 218, 220. Node 202 is coupled to the non-inverting input (pin 5) of amplifier 213. The inverting input (pin 6) of amplifier 213 is coupled to the output node 214 to achieve operation as a voltage follower. Diode 215 and capacitor 218 generate on node 216 a voltage corresponding to the peak voltage driven onto node 214 by amplifier 213 (less a small voltage drop through diode 215), and bleeder resistor 217 reduces the voltage on node 216 if the peak voltage on node 214 assumes a lower value corresponding to a decrease in the current through the charge transfer coils 151, 152. Such a situation will be more fully described below in the context of back telemetry. Lastly, the peak voltage on node 216 is RC-filtered by resistor 219 and capacitor 220 to generate on node 257 a signal having less ripple than the signal on node 216. This signal on node 257 is then buffered by the buffer 263 which includes an amplifier 221 (also configured as a voltage follower) to generate on node 222 a more robust signal representing the magnitude of the peak current through the charge transfer coils 151, 152. Resistors 230, 233 and filter capacitor 231 generate a TELEM_CURRENT signal on node 232 having a scaled magnitude relative to the peak charge transfer coil current represented by node 222. In this implementation, with preferred values of the resistors 230, 233 values, the TELEM_CURRENT signal has a magnitude that is one-half the magnitude of the peak charge transfer coil current.

Comparator 228 is configured to essentially "compare" the instantaneous charge transfer coil current against a percentage of the peak charge transfer coil current, and generate the falling-edge on the TRIGGER signal 106 during each cycle of resonant operation when the rising edge of the instantaneous charge transfer coil current rises above a predetermined percentage of the peak charge transfer coil current.

The voltage signal on node 202 corresponds to the instantaneous charge transfer coil current, which is coupled through resistor 227 to the inverting input of comparator 228. The peak charge transfer coil current signal on node 222 is divided by a resistor divider formed by resistors 225, 223 to generate on node 226 a reference signal representing a predetermined percentage of the peak charge transfer coil current. Capacitor 224 provides local filtering to stabilize this signal on node 226, which is coupled to the non-inverting input of comparator 228. When the inverting input of comparator 228 rises above the non-inverting input, the output signal TRIGGER on node 106 is driven low, as is depicted in FIG. 19A.

The "peak charge transfer coil current" signal on node 222 varies as one or more secondary coils is de-tuned, such as would occur to indicate that charging is complete (if such de-tuning occurs continuously) or to communicate back telemetry data from one of the IPGs (if such de-tuning is performed corresponding to a bit-serial data stream). The TELEM_CURRENT signal on node 232 is preferably configured to correspond to slowly changing values of the peak charge transfer coil current, while the remaining circuitry to the right of amplifier 221 is utilized to detect more frequent (i.e., higher frequency) changes in the charge transfer coil current, as would occur during back telemetry of data from one of the IPGs.

The buffer 263 output signal on node 222 is AC-coupled through capacitor 234 to node 246, which is nominally biased by resistors 235, 236 at one-half the 4VH voltage on node 201, which essentially is the VBAT voltage on node 785. Thus, node 246 has a nominal DC bias equal to VBAT/2, upon which is superimposed an AC signal corresponding to changes in the magnitude of the peak charge transfer coil current. This node 246 is coupled to an input of a band-pass filter/amplifier 264, which includes an amplifier 237, resistors 239, 241 and capacitors 240, 248. Specifically, node 246 is coupled to the non-inverting input of amplifier 237. Feedback resistor 239 and capacitor 240 are each coupled between the output node 238 of amplifier 237 and the inverting input node 247 of amplifier 237.

The band-pass filter/amplifier 264 generates on its output node 238 an analog signal representing received data. This analog data signal is coupled through resistor 242 to generate an analog "back telemetry" signal BKTELEM_ANA. The band-pass filter/amplifier 264 also generates on node 245 a reference signal corresponding generally to the midpoint of the transitions of the analog data signal on node 238, which is the same bias level (e.g., VBAT/2) as node 246. This signal is coupled through resistor 256 to generate a reference "back telemetry" signal BKTELEM_REF. Both the BKTELEM_ANA and BKTELEM_REF signals may be conveyed to control circuitry (not shown) and may be used as diagnostic test points.

The gain of the band-pass filter/amplifier 264 is determined by the value of resistor 239 divided by the value of resistor 241. In certain preferred implementations, the gain may be equal to 10. The value of capacitor 240 is selected to provide the desired high frequency rolloff, and the value of capacitor 248 is selected to provide the desired low frequency rolloff.

The analog data signal on node 238 and the analog reference signal on node 245 are coupled to a comparator circuit 265 to generate on its output node 250 a digital signal representing the back telemetry data signal. The comparator circuit 265 includes a comparator 249 having a local (4VG) power supply node 254 which is coupled to the battery voltage VBAT (conveyed on node 785) using a small noise-isolation resistor 253 and a local filter capacitor 255. In this implementation, the comparator circuit 265 is preferably configured to provide a voltage gain of 27, which is determined by the input resistor 243 connected between node 238 (i.e., the output node of the band-pass filter/amplifier circuit 264) and the non-inverting input node 244 of comparator 249, and the feedback resistor 252 connected between the output node 250 of comparator 249 and the non-inverting input node 244 of comparator 249. The voltage of this non-inverting input node 244 is compared to the data reference voltage coupled to the inverting input node 245 of comparator 249 to generate on output node 250 the digital signal representing the back telemetry data signal. This digital signal is coupled through resistor 258 to generate on node 251 a digital back telemetry data signal BKTELEM_DIG.

Figure 20:
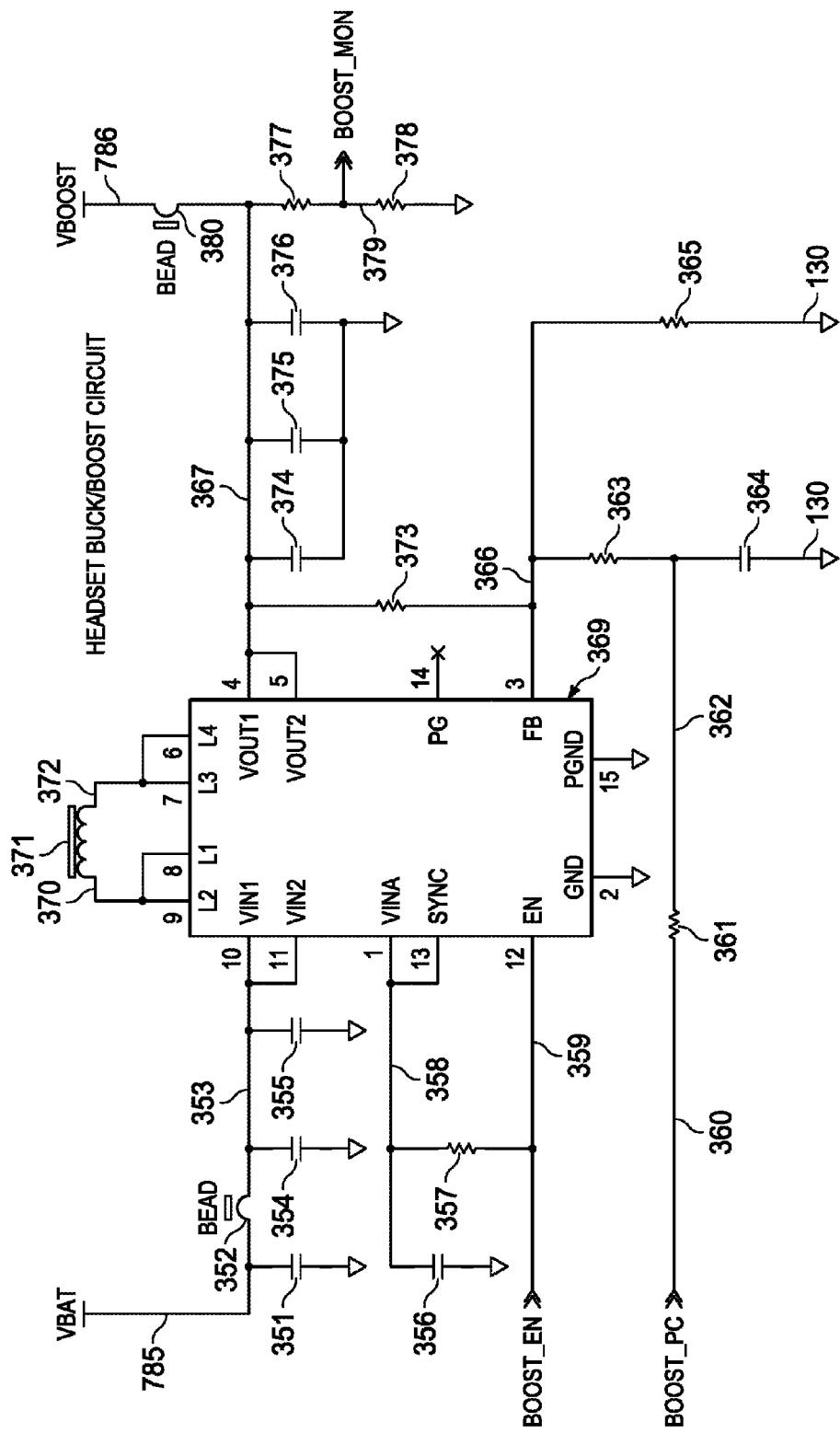
FIG. 20 is a schematic diagram of an exemplary headset buck/boost voltage generator circuit, such as that shown in FIG. 8, in accordance with some embodiments of the invention.

FIG. 20 is a schematic diagram of an exemplary headset buck/boost circuit, such as the buck/boost circuit 787 shown in FIG. 17. In this embodiment, the buck/boost circuit utilizes a commercially available high efficiency single-inductor buck-boost converter circuit 369, such as the TPS36020 from Texas Instruments, Inc. The VBAT voltage conveyed on node 785 is coupled to an input filter circuit that includes capacitor 351, ferrite bead 352, and capacitors 354, 355, whose output on node 353 is coupled to a pair of voltage input pins VIN1, VIN2 of the converter circuit 369. A single inductor 371 is coupled between a first pair of connection pins L1, L2 (node 370) and a second pair of connection pins L3, L4 (node 372). The output of converter circuit 369 is provided on a pair output pins VOUT1, VOUT2, which are coupled via node 367 to an output filter circuit that includes capacitors 374, 375, 376 and ferrite bead 380, to provide the VBOOST voltage on node 786. A precision resistor divider 377, 378 provides a monitoring voltage BOOST_MON on node 379.

A boost enable input signal BOOST_EN is coupled via node 359 to an enable input EN of the converter circuit 369, and also coupled to an RC-filter circuit formed by resistor 357 and capacitor 356, whose output on node 358 is coupled to a VINA pin (supply voltage for the control stage) and SYNC pin (enable/disable power save mode; clock signal for synchronization) of the converter circuit 369. The converter output voltage on node 366 is coupled to a voltage divider circuit that includes resistors 373, 365 to generate on node 366 a feedback voltage which is coupled to the FB input of the converter circuit 369. A boost PC input signal BOOST_PC is coupled via node 360 to a voltage divider adjustment circuit that includes resistors 361, 363 and capacitor 364, each coupled to node 362, and whose output is coupled to node 366. In this manner the BOOST_PC signal can essentially alter the voltage divider ratio to adjust the output voltage of the converter 369 and thus alter the VBOOST voltage.

Figure 23A:
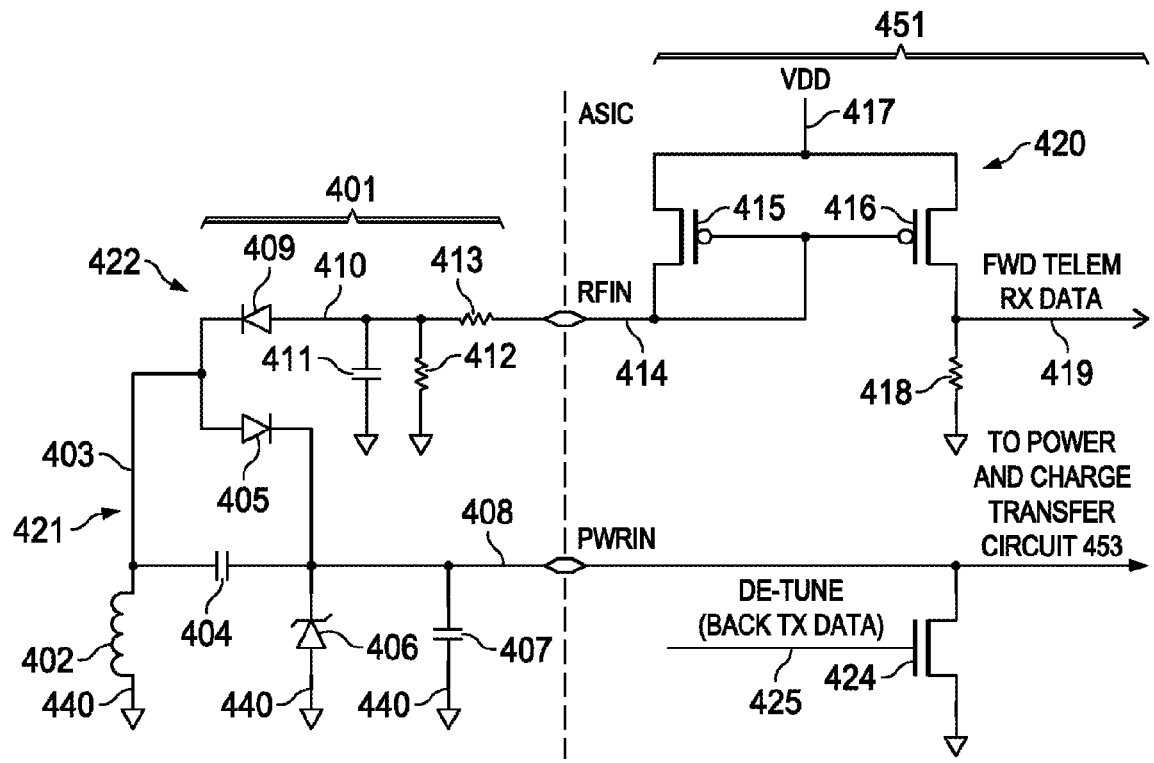
FIG. 23A is a schematic diagram of an exemplary rectifier circuit and telemetry/de-tune circuit, such as those shown in FIG. 21, in accordance with some embodiments of the invention.

As noted above, FIGS. 19A, 19B, and 19C illustrate voltage waveforms of selected signals depicted in the embodiment shown in FIG. 18, and also several signals depicted in FIG. 23A. FIG. 19A generally illustrates waveforms related to sensing the charge transfer coil current and generating the TRIGGER signal accordingly. The various waveforms show the charge transfer coil current, the I-to-V Converter 260 output signal on node 202 without the effect of the ground restore circuit 261, the I-to-V Converter 260 output signal on node 202 with the effect of the ground restore circuit 261, the demodulator node 257, the reference node 226 (shown having a value equal to 60% of the peak voltage on node 257), and the resulting TRIGGER signal on node 106. The left half of the figure corresponds to a lower magnitude of charge transfer coil current, and the right half of the figure corresponds to a higher magnitude of charge transfer coil current.

FIG. 19B generally illustrates waveforms related to the driver control 162 and the resonant amplifier 163. Shown are the TRIGGER signal on node 106, the resulting waveform on NAND 108 input 2 (node 109), the NAND 108 input 1 (node 104), the resulting waveforms on the NAND 108 output node 114, and the buffer 125 output node 131, the resulting voltage on the drain terminal of transistor 133 (node 134), and the current through the charge transfer coils 151, 152. The resonant oscillation frequency in this exemplary embodiment corresponds to an oscillation period of about 1.33 microseconds.

FIG. 19C generally illustrates waveforms related to forward telemetry operation. The upper waveform illustrates the FWDTELEM signal on node 101 conveying a serial bit stream data signal conveying several bits of information, with each bit interval, for this exemplary embodiment, being about 100 microseconds long. When the FWDTELEM signal is driven high at transition 322, the NAND 108 input 1 (node 104) is driven to ground, as shown in the second waveform, to disable the charge transfer coil driver 161. As a result, the previously oscillating signal on the gate node 131 of transistor 133 is likewise driven to ground, as shown in the third waveform, which disables the resonant amplifier 163 and causes the charge transfer coil 151, 152 current to decay and eventually cease, as shown in the fourth waveform. The fifth and sixth waveforms are described below in detail with regard to FIG. 22A, and illustrate the current in the receive coil 402 likewise decays and ceases, resulting in a corresponding signal on the negative peak detector output node 410, and a resulting falling transition 323 on the FWD TELEM RX DATA signal on node 419. An additional logical inversion of this signal may be easily accomplished to generate a data signal having the same polarity as the FWDTELEM signal.

When the FWDTELEM signal is driven low at transition 324, the NAND 108 input 1 (node 104) charges back to a high level, which allows the driver control 162 to again oscillate, initially controlled by its own feedback "watchdog timer" operation, and later under control of the TRIGGER signal. As a result, the gate node 131 of transistor 133 again exhibits an oscillating signal causing transistor 133 to periodically "pump" the resonant amplifier 163, and the charge transfer coil 151, 152 once again oscillates, as shown in the fourth waveform. As described below in detail with regard to FIG. 22A, the current in the receive coil 402 is induced because of the charge transfer coil current, resulting in a corresponding signal on the negative peak detector output node 410, and a resulting rising transition 325 on the FWD TELEM RX DATA signal on node 419.

N. Implantable Pulse Generator

Figure 21:
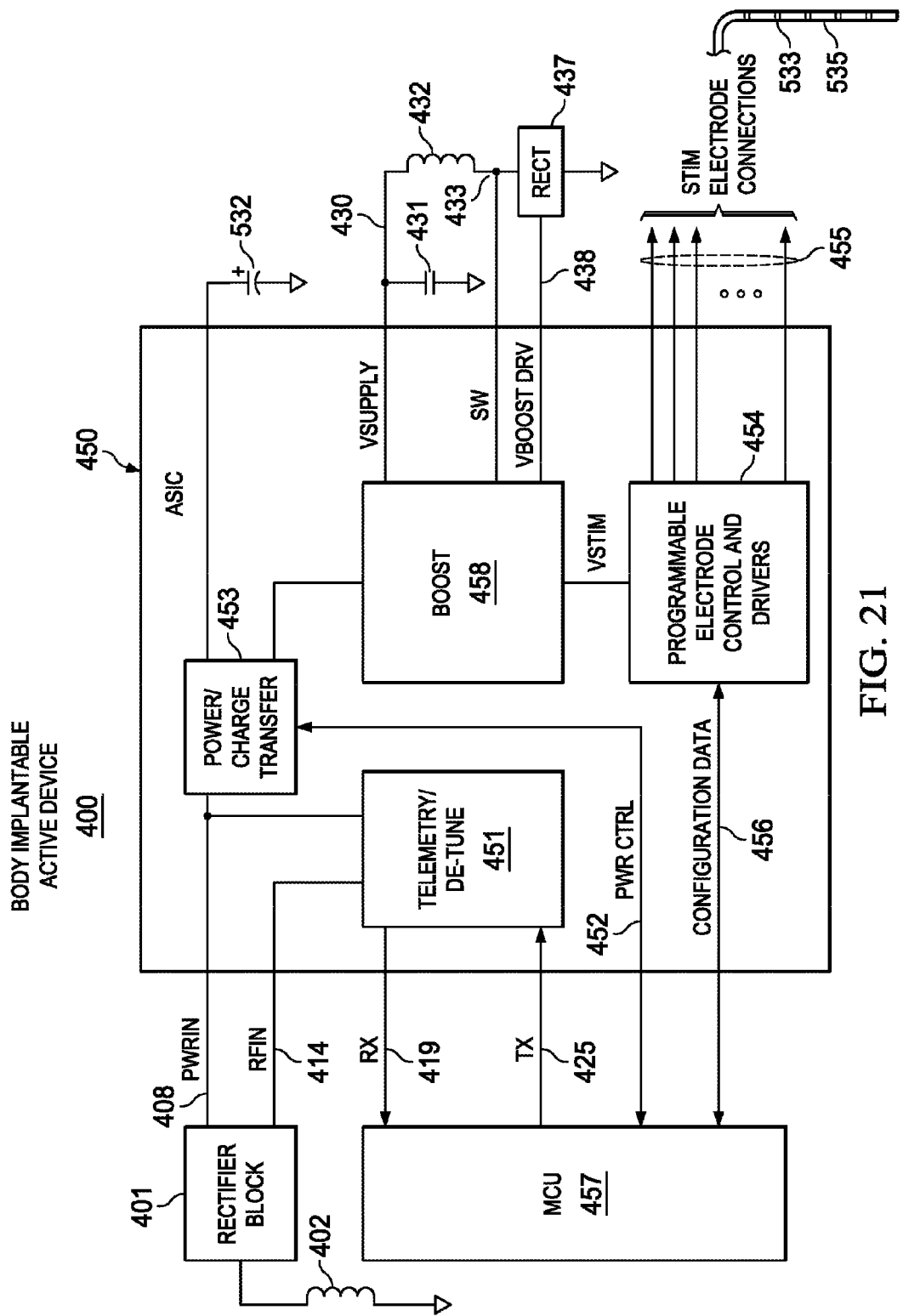
FIG. 21 is a block diagram of a body-implantable active device, in accordance with some embodiments of the invention.

FIG. 21 is a block diagram of an exemplary body-implantable active device 400, such as an implantable pulse generator (IPG) device. A receive coil 402 (also referred to as a secondary coil 402) is connected to a RECTIFIER block 401 that generates a PWRIN signal on node 408 and an RFIN signal on node 414. Both the PWRIN signal on node 408 and the RFIN signal on node 414 are connected to a TELEMETRY/DE-TUNE block 451 that receives a forward telemetry signal on the RFIN node 414, and which interacts with the PWRIN node 408 to de-tune the receive coil 402 to thereby communicate back telemetry information and/or disable further energy transfer to the receive coil 402. The PWRIN node 408 is also connected to a POWER/CHARGE TRANSFER block 453 that is responsible for generating one or more internal voltages for circuitry of the body-implantable device 400, and for transferring charge to a supercapacitor 532 and for providing charge to the electrode of one or more electrodes 533.

A microcontroller (MCU) 457 provides overall configuration and communication functionality and communicates forward and back telemetry information via a pair of data lines 419, 425 coupled to the TELEMETRY block 451. Data line 419 conveys a forward telemetry RX signal, and data line 425 conveys a back telemetry TX signal. The MCU 457 receives information from and provides configuration information to/from the POWER/CHARGE TRANSFER block 453 via control signals PWR CTRL conveyed on control lines 452. A programmable electrode control and driver block 454 (DRIVERS 454) generates electrical stimulation signals on each of a group of individual electrodes 455. An adjustable voltage generator circuit BOOST 458, which is coupled via signals VSUPPLY (node 430), SW (node 433), and VBOOST DRV (node 438) to components external to the ASIC 450 (including capacitor 431, inductor 432, and rectifier block 437) provides a power supply voltage VSTIM to the DRIVERS block 454.

The MCU 457 provides configuration information to the DRIVERS block 454 via configuration signals CONFIGURATION DATA conveyed on configuration lines 456. In some embodiments, the POWER/CHARGE TRANSFER block 453, the TELEMETRY block 451, the BOOST circuit 458, and the DRIVERS block 454 are all implemented in a single application specific integrated circuit (ASIC) 450, although such is not required. In the overall operation, the ASIC 450 functions as a state machine that operates independently of the MCU 457. The MCU 457 includes Flash memory for storing configuration data from the external control system (not shown) to allow a user to download configuration data to the MCU 457. The MCU 457 then transfers this configuration data to ASIC 450 in order to configure the state machine therein. In this manner, the MCU 457 does not have to operate to generate the driving signals on the electrodes 455. This reduces the power requirements. Other embodiments may implement these three functional blocks using a combination of multiple ASIC's, off-the-shelf integrated circuits, and discrete components.

Charge transfer is monitored by the ASIC 450 and adjusted to provide the most efficient charge transfer conditions and limit unnecessary power dissipation to provide a constant current to the supercapacitor 532 and electrodes 533. Preferable conditions for charging the supercapacitor include a charging voltage of approximately 4.5 V for most efficient energy transfer (with a minimum charge voltage of about 4.0 V). Also, it is particularly desirable to maintain a constant charge transfer current into the supercapacitor in a charging charge transfer operation during the entire charge transfer time, even as the battery voltage increases as it charges. Preferably this constant charge transfer current is about C/2, which means a charging current that is one-half the value of the theoretical current draw under which the supercapacitor would deliver its nominal rated capacity in one hour. To accomplish this, a variety of sensors and monitors (not shown) may be included within the body-implantable device 400 to measure power levels, voltages (including the battery voltage itself), charge transfer current, and one or more internal temperatures.

As a further description of the overall operation of the IPG, the general operation is that of a state machine utilizing the ASIC 450. In general, the MCU 457 is utilized as an instruction based processor for communication and configuration operations. The state machine 450 is more efficient in carrying out a simple repetitive program, once configured and initiated. Thus, in operation, the state machine or ASIC 450 is normally running the stimulation program and controlling the current to the lead 535 and the various electronic connections 455. During the operation of the state machine, however, there are certain times when information has to be transmitted back to the headset in order to change, for example, the transmittal power level. As noted hereinabove, it is important to minimize the amount of power that is transmitted across the dermis to the coil 402 in order to minimize heating. Thus, it is important to keep the voltage level on the node 408 as low as possible while maintaining the system in constant current regulation. Current regulation is monitored and, when the system goes out of current regulation due to the input voltage 408 falling, a request is sent back to the headset to increase the power transferred. This requires the state machine 450 to wake up the MCU 457 to effect the communication. Once current regulation is achieved, it is then not necessary to have the MCU operating and it will be placed into a "sleep" mode of operation. Whenever configuration information is required to be sent to the IPG from the headset, the headset then sends a request to the IPG, which wakes up the MCU 457. The MCU 457 then services this request and downloads configuration information to the internal Flash memory, a nonvolatile memory. The configuration is stored in the MCU 457 and then the MCU 457 uploads the configuration data to the ASIC 450. Thus, the MCU 457 is basically utilized for the communication operation with the headset and also as a repository for configuration information for the ASIC 450.

Figure 22A:
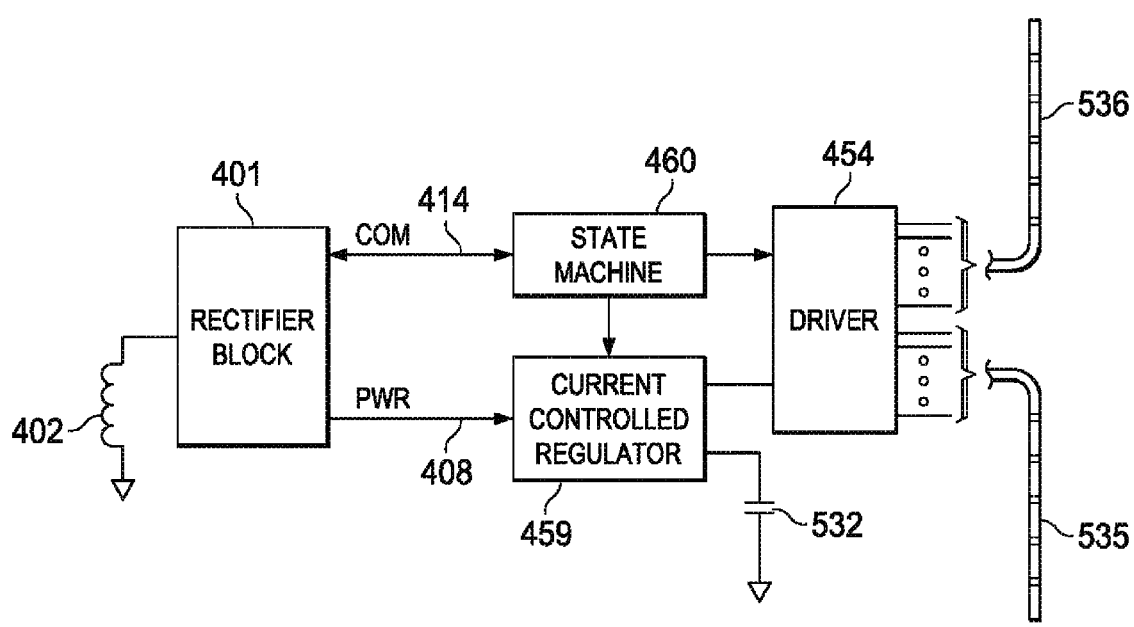
FIG. 22A illustrates a simplified block diagram of the IPG.

Referring now to FIG. 22A, there is illustrated a five block diagram of the IPG. As noted hereinabove, there is provided overall state machine 460 to control the operation of the system to control drivers to provide a constant current level to electrodes on any one of multiple leads 535 or 536. The driver 454 is provided current through a current controlled regulator 459. The power level is adjusted via communication with the headset to adjust the power transferred to the coil 402 vary the voltage out of the rectifier block 401. This current controlled regulator 459 is controlled to both charge and maintain charge on the supercapacitor 532 and also provide current to the driver 454. Once the supercapacitor 532 is charged, and the current required by the driver 454 is more than can be provided by the supercapacitor 532, the driver 454 receives all of the power from the headset across the coil 402. As long as the voltage level on the node 408 is at a sufficient level to maintain current regulation in the regulator 459, current can be provided at the appropriate regulated level. However, if the voltage level increases at node 408, heat will be dissipated in the regulator 459 unnecessarily. Therefore, communication is maintained with the headset to minimize the amount of power transferred to lower the voltage on node 408 to a point that is high enough to maintain current regulation but no higher. Thus, when the voltage required to drive the coil on the headset side is lowered, the regulator 459 falls out of regulation, at which time, the request will be sent back to the headset to increase the power in order to just maintain the necessary voltage on node 408 to maintain current regulation for a particular neurostimulation program being run.

Figure 22B:
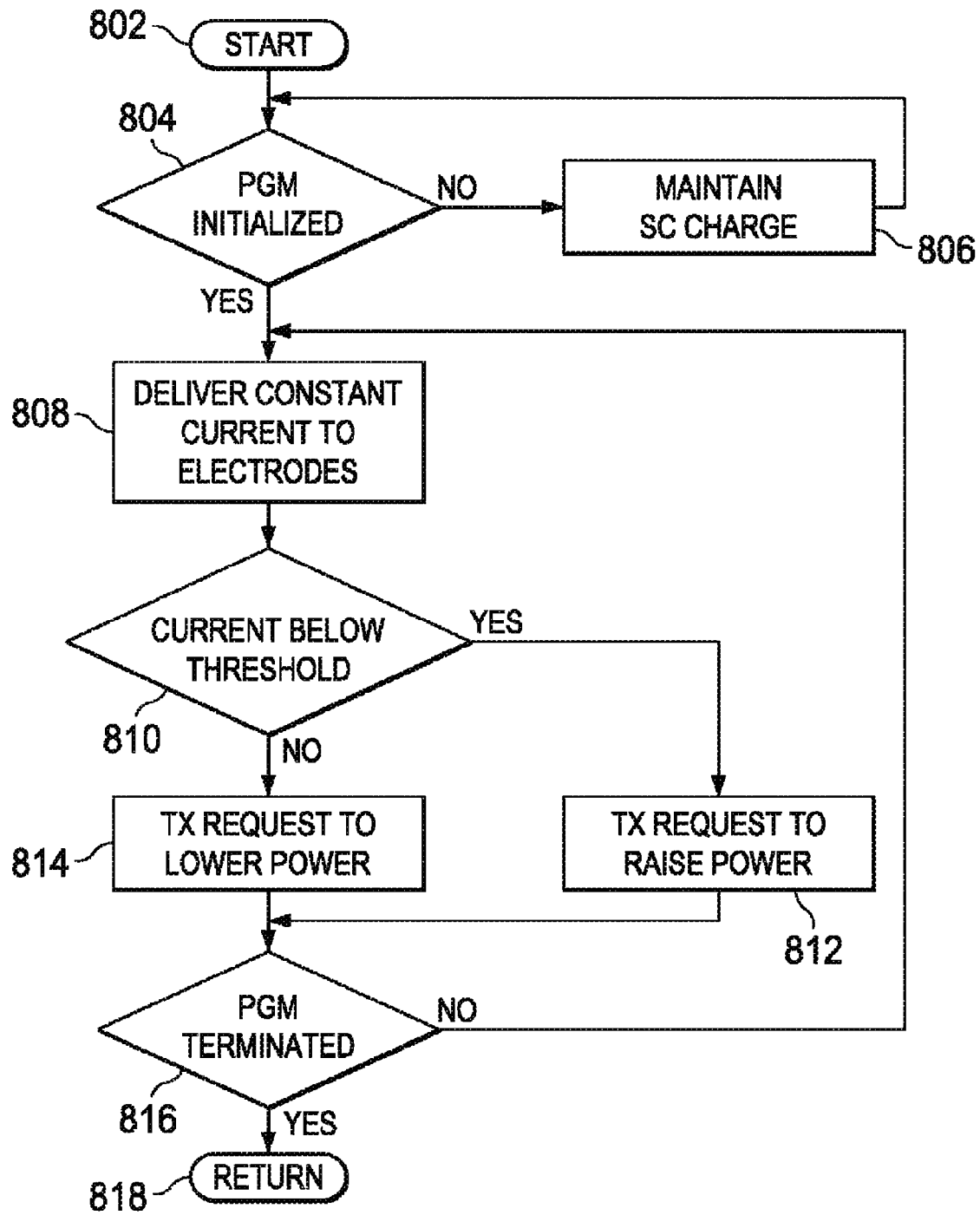
FIG. 22B illustrates a flow chart for the operation of the initiation of a neurostimulation program at the IPG.

Referring now to FIG. 22B, there is illustrated a flowchart depicting the overall operation of running a program, which is initiated at a Start block 802. The program then flows to a decision block 804 to determine if a program has been initiated on the IPG to provide stimulation to the individual. If so, this will then require the electrodes to be driven with a constant current. Until a program is initiated, the process goes to block 806, where the amount of power required to maintain the IPG in a low power mode is minimal. This can be facilitated by maintaining the supercapacitor 532 in a charge configuration. The supercapacitor 532 is a type of capacitor that functions as a battery in that it will maintain a small, charge their own for short duration of time. When the system is initially turned on, there will be no power to the unit and the supercapacitor 532 must be charged from a zero value. Thus, the system is placed into an initial Power Up mode of operation to power on the MCU 457 and the ASIC 450, at which time the current is limited to the supercapacitor 532. Once power is at a sufficient level to power the MCU 457, charge will be delivered to the supercapacitor 532, but this will be delivered at a maximum current level to ensure that the amount of charge transfer crossed the dermis to the coil 402 is minimize to reduce heating. Once the supercapacitor 532 is charged, then the system will go into a normal operating mode and, if there is no stimulation program that is required to be run at that time, MCU 457 will put into a sleep mode and the coil 402 detuned to eliminate power transfer thereto, such that all power provided in the sleep mode is provided by the supercapacitor 532. As the charge falls on the supercapacitor 532, the coil 402 will be tuned to allow power to be transferred to the IPG from the headset. This will maintain the supercapacitor 532 in a charged state. In the event that the headset is removed, and tuning of the coil 402 in order to allow charge to be transferred results in no charge being transferred, this indicates a possible powerdown mode. All compliments we placed in their lowest power mode to ensure that the supercapacitor 532 can maintain the IPG in a low power sleep mode for as long as possible. Since all configuration data for the ASIC 450 is stored in the MCU 457, it is not necessary to modify the configuration data, as it can always be uploaded back to the ASIC 450 in the power of mode. The supercapacitor 532 is provided to allow the IPG to be maintained in a low power mode for a short duration of time. If, for example, the IPG were in the middle of a stimulation program, delivering current to the electrodes, and the headset were removed, then the ASIC 450 would terminate the program to prevent additional current from being drawn from the supercapacitor 532.

Once the program is initiated, the program will flow to a function block 808. This will result in constant current being delivered to the select electrodes on the lead 535 by the drivers 454 in accordance with the stimulation program. The stimulation program could activate certain electrodes on the lead, define certain electrodes as cathodes or anodes or isolate certain electrodes and also define the amount of current that is the being delivered to a particular electrode, the waveform that is been being delivered thereto, etc. The program then flows to a decision block 810 in order to determine if the current is at a defined current threshold. If the current is below current threshold, i.e., the amount of power being delivered necessary to maintain current regulation, ASIC will recognize that the current regulator has fallen out of regulation and move to function block 814, where the MCU 457 will affect a transmit of a request to raise the power at the headset in order to increase power transfer to the coil 402. It may be that other IPGs have sent a request to lower power, but each IPG will independently request a higher power to maintain current regulation for its drivers. If, however, the current is not below the threshold, the process moves to block 812, where the MCU 457 will transmit a request to the headset to lower the headset power and power transfer. In some embodiments, function block 812 is optional, and the headset may, on its own, lower the power if, after a certain period of time, none of the IPGs have requested increased power. The headset will lower the power only if there is no request to increase power from other IPGs. This, of course, may result in a higher power than is necessary for the input of the current regulator at the requesting IPG, but it is only important that the IPG requiring the most power transfer be serviced by the headset and the power transfer maximized for that IPG. As soon as an IPG goes into a sleep mode, it will no longer send requests for power level increases or decreases and the headset will recognize this and periodically decrease the power. If the power goes too low for a particular IPG, then that IPG will indicate to the headset that the power needs to be increased at the headset and the power transfer increased. Once current regulation is established, the program flows to a decision block 816 to determine if the neurostimulation program at the IPG has been terminated. If so, the program flows to a Return block 818 and, if not, the program flows along a "N" block back to the input of the function block 808.

FIG. 23A is a schematic diagram of an exemplary RECTIFIER block 401 and TELEMETRY/DE-TUNE block 451, both such as those shown in FIG. 21. The exemplary RECTIFIER block 401 includes a resonant half-wave rectifier circuit 421 and a half-wave data rectifier circuit 422. The resonant half-wave rectifier circuit 421 may be viewed as an "energy receiving circuit" and the half-wave data rectifier circuit 422 may be viewed as a "data receiving circuit." The exemplary TELEMETRY/DE-TUNE block 451 includes a current mirror circuit 420, and a de-tuning transistor 424.

The circuitry depicted in FIG. 23A may be viewed as a portion of a charge receiving system which includes a secondary coil 402, an energy receiving circuit (421), and a data receiving circuit (422). The resonant rectifier circuit 421 includes diode 405, capacitor 404, and capacitor 407, which, together with the secondary coil 402, operates as a resonant half-wave rectifier circuit. When the secondary coil 402 is disposed in proximity to its associated charge transfer coil, such as one of the charge transfer coils 151, 152 (see FIG. 18), during a time when the resonant amplifier 163 is operating, the charge transfer coil and the secondary coil may be inductively coupled and may have, with careful design of the coils and reasonably close physical proximity, a Q that approaches 100. Consequently, the resonant amplifier circuit 163 and the resonant rectifier circuit 421 will operate as a resonant Class E DC-to-DC voltage converter. During such operation, energy is coupled to the secondary coil 402 due to magnetic induction.

This induced energy in secondary coil 402 is manifested as a sinusoidal voltage on node 403 that traverses above and below the ground reference level on node 440. This AC voltage on node 403 is half-wave rectified to provide a DC voltage on node 408 that may be used to provide power to both operate and/or charge the supercapacitor (if present)

within the IPG. Specifically, because a single diode 405 is used in this circuit, and due to the polarity of this diode, only the positive voltage transitions on node 403 are rectified, thus creating a positive DC voltage on node 408. A zener diode 406 is coupled between node 408 and ground to prevent an excessive positive voltage from being generated at node 408.

The above description of the resonant rectifier circuit 421 and its half-wave rectifier circuit operation has assumed that transistor 424 remains off. This ensures that the Q of the combined primary charge transfer coil 151 and the secondary coil 402 remains high, and energy is efficiently transferred. However, if transistor 424 is turned on (when the DE-TUNE/BACK TX DATA signal on node 425 is high), the secondary coil 402 is "de-tuned" which significantly reduces the Q of the resonant circuit, and thereby reduces charge transfer and thus reduces coupled power into the secondary coil 402. This may be useful at times to reduce power, such as when the supercapacitor has been fully charged or when no charge delivery is required. It is also useful to turn on transistor 424 to communicate back telemetry information to the charge transfer system. Analogous back telemetry operation is described above in reference to FIGS. 14A and 18, and corresponding waveforms are shown in FIGS. 14B and 19A.

The data receiving circuit 422 includes diode 409, capacitor 411, and resistor 412, which together may be viewed as a negative half-wave rectifier circuit or negative peak-detector circuit. Irrespective of whether the de-tune transistor 424 is active, the generated voltage on node 410 corresponds to the peak negative voltage of the sinusoidal voltage signal on node 403. If the peak negative voltage increases in magnitude (i.e., becomes more negative) over multiple cycles, the diode 409 will quickly drive node 410 to a correspondingly more negative voltage, and capacitor 411 serves to maintain this voltage. Conversely, if the peak negative voltage decreases in magnitude (i.e., becomes less negative) over multiple cycles, the resistor 412 will drive node 410 to a correspondingly less negative voltage. The value of resistor 412 and capacitor 411 may be chosen to provide a response time that is consistent with forward telemetry data rates. Exemplary forward telemetry data rates may be on the order of 10 kHz.

The data receiving circuit 422 together with the current mirror circuit 420 generates on node 419 a signal FWD TELEM RX DATA reflecting the forward telemetry received data. The current mirror 420 is powered by a VDD voltage conveyed on node 417, and generates a reference current through resistor 413 and P-channel transistor 415, which is mirrored by P-channel transistor 416 to generate a current through resistor 418 which generates a corresponding voltage signal on node 419. Depending upon the current gain of the current mirror 420, node 419 may be either driven virtually all the way to the VDD voltage (less a $V_{DSSAT}$ voltage of transistor 416), or may be pulled by resistor 418 well toward ground, to generate a "quasi-digital" forward telemetry receive data signal. Additional digital regeneration circuitry (e.g., within the ASIC, and not shown) may be employed to create a truly digital data signal.

Figure 23B:
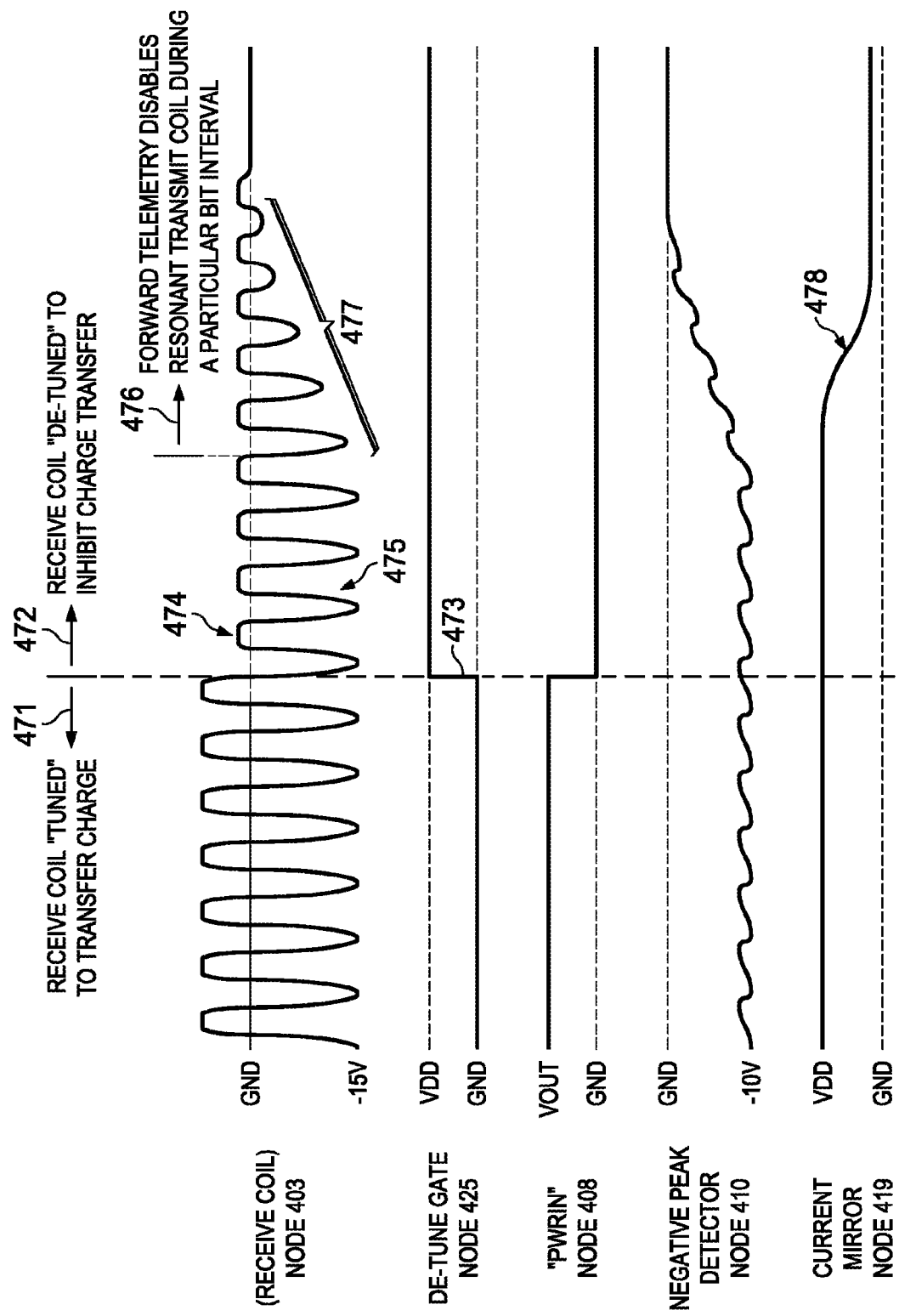
FIG. 23B illustrates voltage waveforms of selected signals depicted in the embodiment shown in FIG. 23A.

FIG. 23B generally illustrates voltage waveforms of selected signals depicted in the embodiment shown in FIG. 23A. In particular, waveforms are shown for the induced voltage at node 403 (one end of the receive coil 402), the DE-TUNE gate signal on node 425, the PWRIN signal on node 408, the negative peak detector signal on node 410, and the current mirror output node 419. The left portion 471 corresponds to the receive coil 402 being "tuned" to transfer charge, the right portion 472 corresponds to the receive coil 402 being "de-tuned" to inhibit charge transfer, in response to the transition 473 of the DE-TUNE gate signal to a high level, as shown in the second waveform. This high voltage level turns on transistor 424, which grounds node PWRIN, as shown in the third waveform, and likewise "clamps" the voltage on node 403 to a small positive voltage 474 due to diode 405, while not affecting the negative induced voltage 475 on node 403, and similarly without affecting the negative peak detector voltage on node 410 and the voltage on current mirror output node 419.

The rightmost portion 476 of the figure shows the induced voltage in receive coil decaying when the resonant amplifier in the external charge transfer system is disabled. This could occur because the external charge transfer system turned off its resonant amplifier in response to detecting a long term de-tuning of the receive coil in the body-implantable active device (i.e., when charge transfer is no longer desired). This could also occur in response to a back telemetry communication calling for charge transfer to cease. This could also occur merely because another bit of forward telemetry information is communicated. In any of such possible situations, the resonant amplifier 163 is disabled, which allows the resonant operation (and AC current through the charge transfer coils) to decay, and as a result the induced negative voltage at node 403 of the receive coil likewise decays, as shown by waveforms 477. This causes a corresponding decay in the voltage of negative peak detector node 410, and an eventual change of state 478 of the current mirror output node 419.

Figure 24:
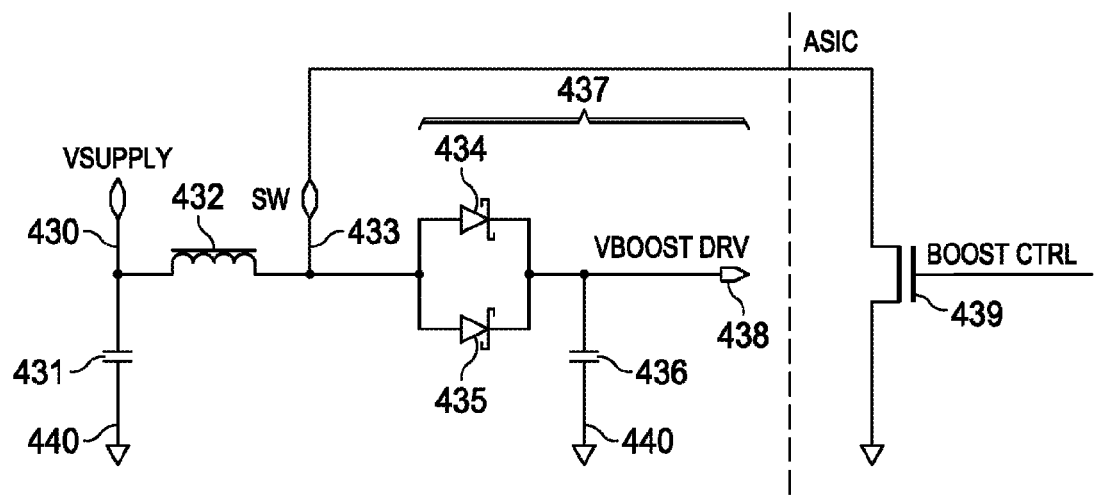
FIG. 24 is a schematic diagram of portions of an exemplary boost circuit, such as that shown in FIG. 21, in accordance with some embodiments of the invention.

FIG. 24 is a schematic diagram of portions of an adjustable voltage generator circuit, such as the adjustable voltage generator circuit BOOST 458 shown in FIG. 22, and particularly highlights the external components to the ASIC 450, in accordance with some embodiments of the invention. In this embodiment, a VSUPPLY voltage generated within the ASIC 450 and conveyed on node 430 is coupled to filter capacitor 431 and inductor 432. The other end of the inductor 432 is coupled via node 433 to the drain terminal of switch transistor 439 within the ASIC 450, which is controlled by a BOOST CTRL signal connected to its gate terminal. A pair of diodes 434, 435 and capacitor 436 together form a rectifier block 437 and serve to rectify the SW signal voltage on node 433 and thus generate the VBOOST DRV voltage on output node 438.

Figure 25:
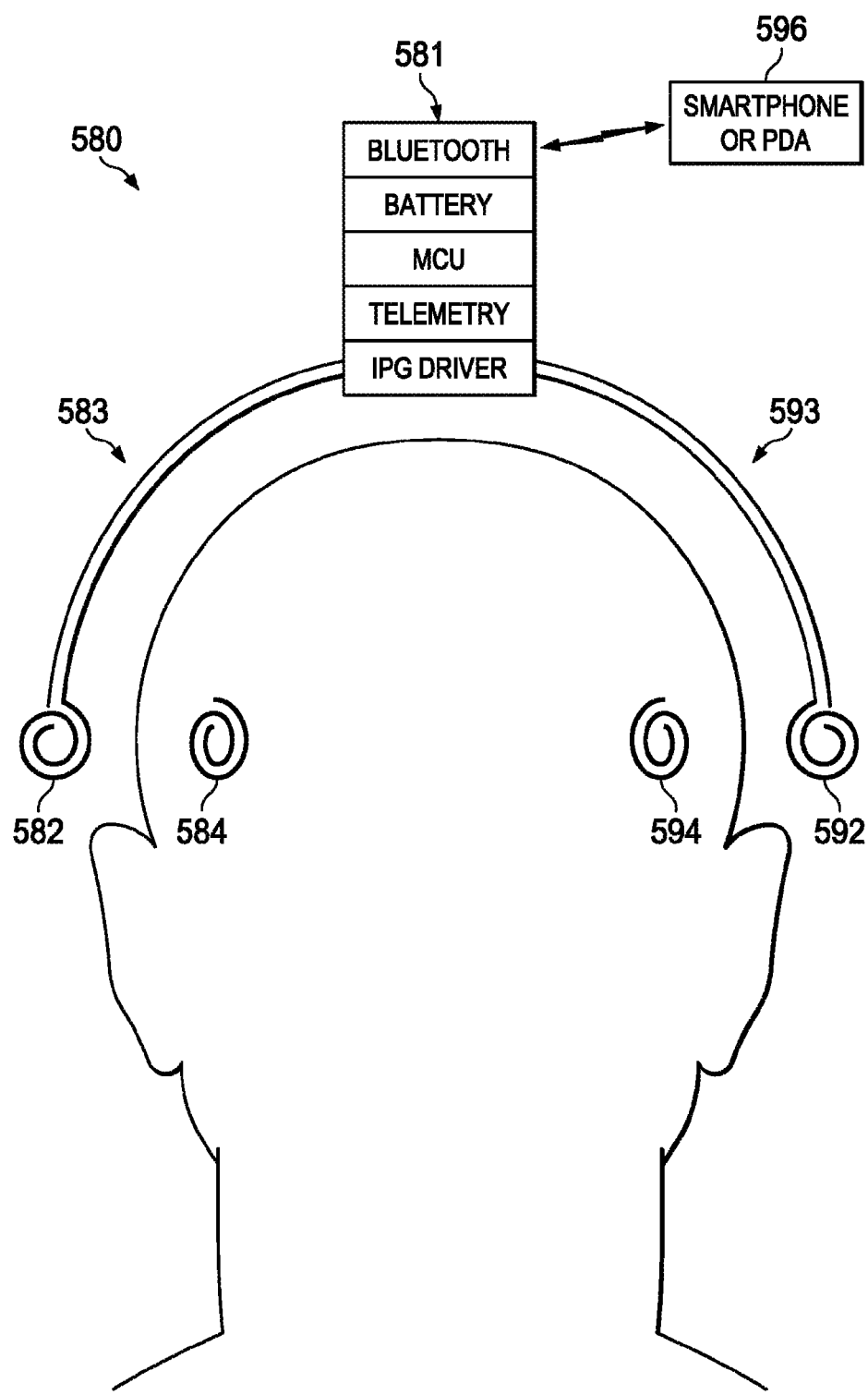
FIG. 25 is a diagram representing an exemplary headset that includes an external charge transfer system for two separate body-implantable devices, each implanted behind a patient's respective left and right ears, and shows an associated headset coil placed in proximity to the corresponding receive coil in each implanted device.

FIG. 25 is a diagram representing a headset 580 that includes an external charge transfer system 581 for two separate body-implantable devices, each implanted behind a patient's respective left and right ears. Each of the body-implantable devices may be a head-located neurostimulator system, such as that described below. The charge transfer system 581 is connected to a pair of headset coils 582, 592 by respective wire pairs 583, 593. When the headset 580 is worn by a patient, the headset coils 582, 592 (charge transfer coils) are placed in proximity to the corresponding receive coil 584, 594 in each respective IPG.

The exemplary headset 580 includes an IPGS driver, telemetry circuit, a microcontroller (MCU), a battery, and a Bluetooth wireless interface. The headset 580 may also communicate with a smartphone or PDA 596, for monitoring and/or programming operation of the two head-located neurostimulator systems.

Figure 26:
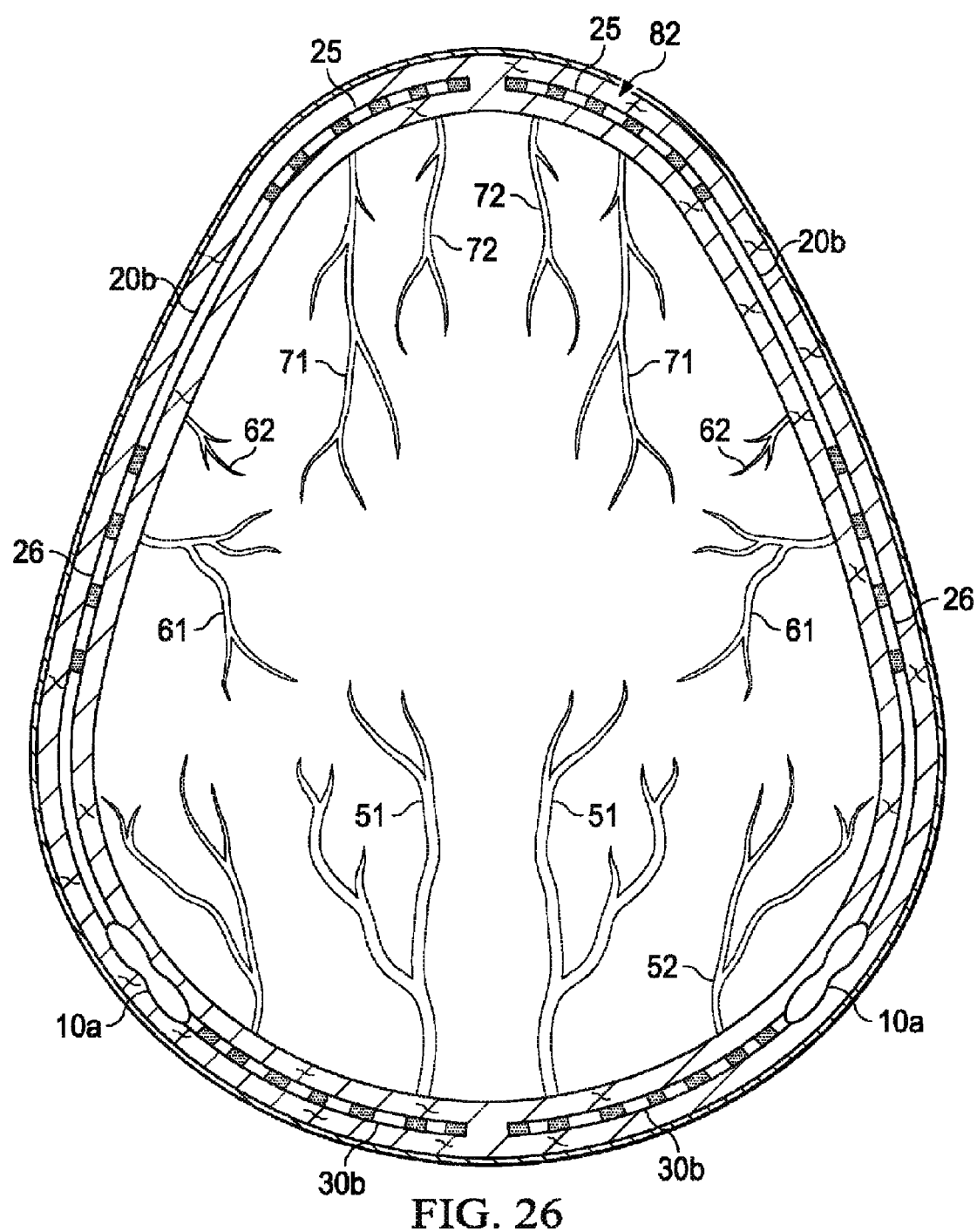
FIG. 26 depicts two implanted IPGs with leads to cover both sides of the head.

FIG. 26 depicts two implanted IPGs with leads to cover both sides of the head. Prominent here are Fronto-Parietal Lead (FPL) 20b and Occipital Lead (OL) 30b, which lie within the subcutaneous layer 82. The two structures are numbered identically with respect to their compliments, and they are implanted identically, one on the left side of the head and one on the right side of the head, as described above. Also illustrated is zygomaticotemporal nerve 62 and the supratrochlear nerve 72.

Figure 27:
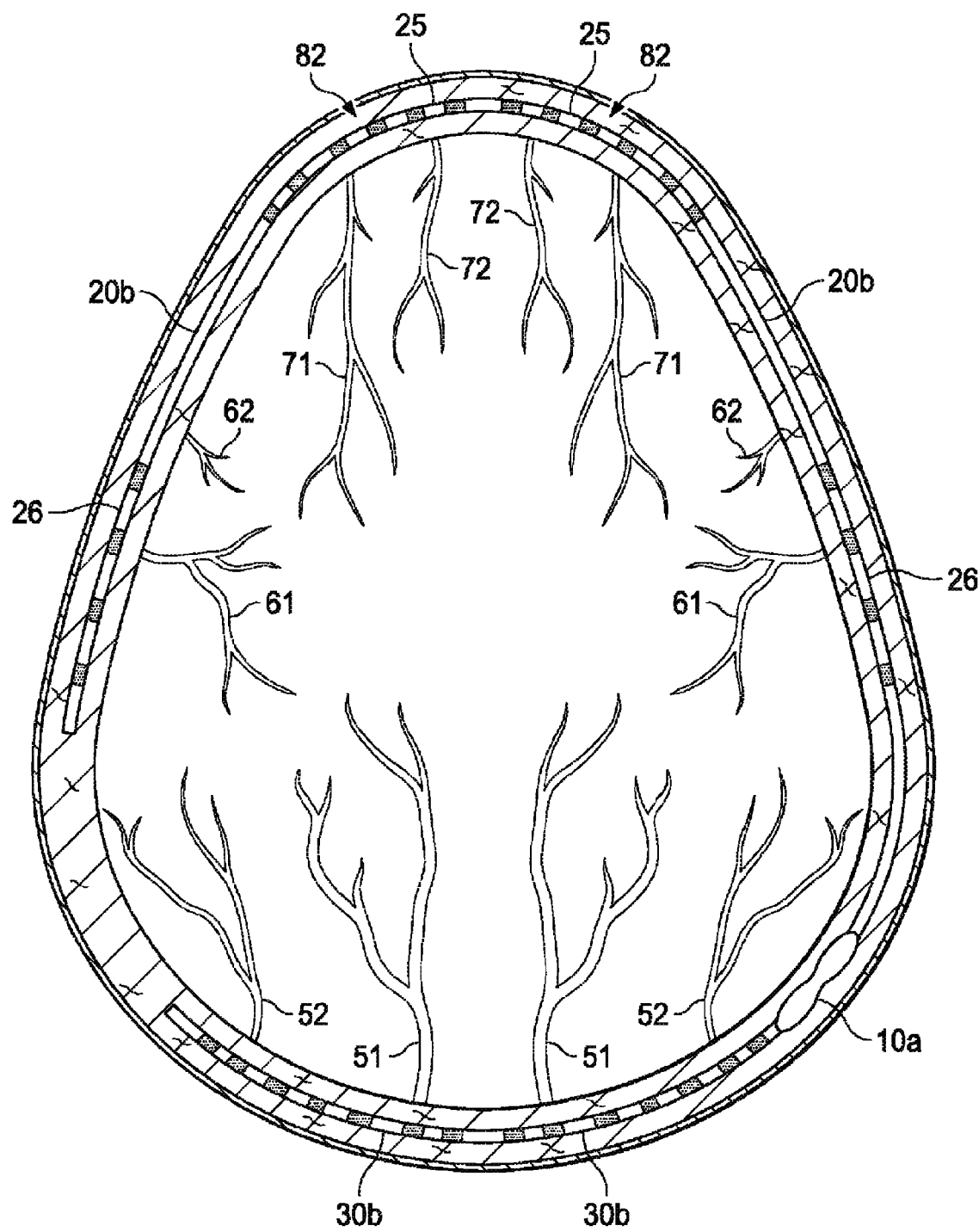
FIG. 27 depicts one implanted IPG with leads to cover both sides of the head.

FIG. 27 depicts one implanted IPG with leads to cover both sides of the head. In this embodiment, the FPL 20b extends from the IPG 10a on one side of the head around the parietal region on that side of the head, the two frontal regions and on the parietal region on the opposite side of the head such that there are two PEAs 26, two FEAs 25 and two OEAs 35. This, of course, requires an incision to be made on the temporal region on the side of the head on which the IPG 10 is implanted and a frontal incision made to allow the FPA 20 to be routed to and in a frontal incision and then to a temporal incision on the upside the head and finally to the parietal region on the upside the head. This is the same with respect to the occipital lead 30 that must be routed through possibly an additional acetylene incision of the back of the head. All that is required is the ability to route particular leads to the respective regions proximate the nerves associated therewith. This will allow a single IPG 10 to cover two frontal regions, two parietal regions and two occipital regions.

The exemplary headset 580 includes an IPG driver, telemetry circuitry, a microcontroller (MCU), a battery, and a Bluetooth wireless interface. The headset 580 may also communicate with a smartphone or PDA 596, for monitoring and/or programming operation of the two head-located neurostimulator systems.

O. First Embodiment

The first embodiment provides for a system that incorporates one or more of the features outlined above and includes a head-mounted, radiofrequency coupled, unibody neurostimulating system comprising an IPG 10 and at least two neurostimulating leads (FPL 20 and OL 30). The system may be implanted in a manner such that the IPG 10 and two leads 20, 30 are disposed as illustrated in FIG. 5, FIG. 6, FIG. 7 and FIG. 9. The IPG 10 is capable of, via a radiofrequency couple, functionally connecting to and communicating with an ECU 100, which houses a power supply, as well as electronic components that provide for diagnostics and programming functionality.

In this embodiment, the leads are constructed as described above and as depicted in the drawings. The FPL 20 is approximately 26 cm in length from its proximal end 22 to its distal end 21. The FPL 20 has a distal non-stimulating tip of approximately 3 mm in length that abuts the FEA, which may have ten SME 24 uniformly disposed over approximately 8 cm. This is followed by an inter-array interval 27 of approximately 4 cm, then the PEA, which may include eight SME 24 uniformly disposed over approximately 6 cm, and finally a proximal lead segment 22a that ends at the proximal end 22, where the lead transitions to the IPG 10 and the lead internal wires 29, 38 connect to the ASIC 13.

In this embodiment, the occipital lead may comprise a plastic body member 39 over which six SME 34 may be disposed uniformly over approximately a 10 cm length of the lead, and the lead terminates in approximately a 3 mm distal non-stimulating tip 33.

In this embodiment, the IPG 10 comprises the elements described above and depicted in the drawings, including an ASIC 13, an internal magnet 12, and an internal radiofrequency receiver coil 11, which all may be housed in a medical grade metal can with plastic cover 14. In this embodiment the dimensions of the IPG 10 measured along the outer surface of the plastic cover 14 may be approximately 5 cm by 3 cm by 0.5 mm.

Figure 3A:
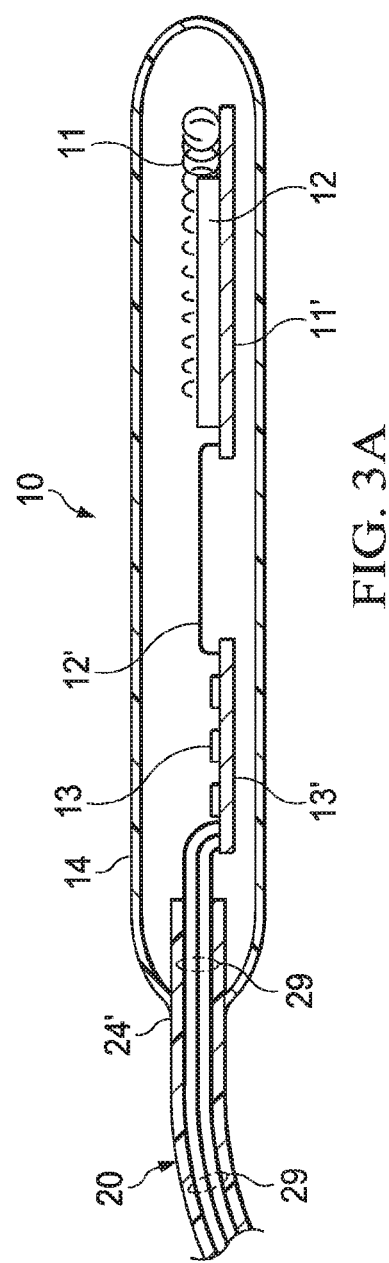
FIG. 3A depicts a more detailed view of the internal structure of an IPG.

This is more fully illustrated in FIG. 3A the implantable pulse generator 10. The ASIC 13 is comprised of multiple chips disposed on a substrate or supporting PC board 13'. The coil 11 and the magnet 12 are disposed on a similar PC board 11' for support thereof. They are connected together by connecting wires 12' for providing power between the coil 11 and the ASIC 13. If the coil 11 is disposed in the distally disposed body 10', the wires in 12' are run through the lead 20' illustrated in FIG. 1B. On the opposite end of the PC board 13' from the wire connection 12', there are provided a bundle of wires 29, associated with the FPL 20, for example, although the wires 38 associated with the OL 30 are not illustrated. This bundle of wires runs through the proximal end of the lead 20. The plastic cover 14 is comprised of a medical grade plastic, formal coating that covers the entire surface of both the coil 11 and the associated structures and ASIC 13. The magnet 12, although not shown, can be disposed within an open well within the cover 14 to allow removal thereof. This is typically done whenever a patient is subjected to an MM, requiring the removal of the magnet and reinsertion of it at a later time. The cover 14 extends downward along the lead 20 to provide a seal therewith and a distal end 24'. This provides a unibody construction, such that the proximal ends of the leads 29 are attached to the PC board 13' during manufacture and then the coating 14 applied thereto.

Turning to FIGS. 8 and 9, the system includes an ECU 100, which functionally couples to the IPG by a radiofrequency couple mechanism. The purpose of the ECU 100 is to provide power to the implanted unit, as well as programming and diagnostic functionality.

In this embodiment, the system is capable of handling a program from the ECU 100 that includes such parameters as pulse amplitude, frequency and pulse width.

In this embodiment, the ECU 100 is positioned "behind the ear" and held in place by an ear clip 1110. The ECU's EBC 1120 contains the main electronics and battery, along with the necessary circuits, the electrical output of which is channeled via the external RF coil lead 1130 to the external RF coil 1141, which is held in place over the corresponding internal RF receiver coil 11 by external and internal magnets 1142, 12. By an RF coupling mechanism, the ECU 100 is capable of providing power, as well as overall unit control, including programming and diagnostic functionality.

P. Alternate Embodiments

There are multiple alternate embodiments that preserve the features of the neurostimulation system disclosed herein, which include variations in the dimensions of the frontoparietal and occipital leads which, along with their respective surface metal electrode arrays, extend to cover multiple regions of the head. In various embodiments, the spacing and dimensions of the electrode array(s) may be constant, or the electrode arrays may be specifically designed with respect to electrode type, dimensions, and layout for improving the therapeutic effectiveness.

Other embodiments may include variations in the design of the external control unit. For example, instead of securing to the head via an ear clip mechanism, it may secure through an "ear muffs" type of mechanism.

Other embodiments may include variations in the design and location of the internal RF coil and internal magnet with respect to the location of the IPG proper. In our primary embodiment here, the IPG is disclosed as having two lobes—one for the ASIC and the other for the internal RF receiver coil and magnet. In one example of an alternate embodiment, the IPG may be provided as a single lobe, which houses the ASIC, internal RF receiver, and internal magnet together.

In another example of an alternate embodiment, the internal RF coil/magnet may be located some distance from the leads and IPG proper and be functionally connected by an extended lead containing internal connecting wires. This embodiment would allow for the RF coil/magnet component to be located at various locations in the head, neck and torso.

Thus, the disclosure comprises extended electrode array designs (two or more regions by a single lead), and/or multiple arrays and optimized intra-array electrode dispositions. The disclosure also comprises lead configurations, which include the capability of a modular lead design that provides for ports on either the standard FPL or OLs. In another embodiment, the IPG receive additional separate leads, if and as necessary either at the time of initial implant or in the future.

Further, the lead lengths, along with the specific technical makeup and dimensions of the individual surface metal electrodes and electrode arrays, may be varied to include more or less than three unilateral regions of the head (occipital, parietal, and frontal) contemplated by the first embodiment. For example, a single IPG may energize and control multiple additional leads of varying lengths that ultimately could be disposed over virtually every region of the head and face bilaterally.

At least two electrodes may be included per region, and while the first embodiment calls for a total of 24 electrodes disposed over three arrays covering three different regions of the head—the occipital, parietal and frontal regions—there is no absolute limit to the maxim number of electrodes. Similarly, while the first embodiment calls for three electrode arrays, the disclosure contemplates two, or even one, array (so long as the array covers at least two regions). There is also no limiting maximum for the number of arrays. Also, there may be multiple variations of design within each separate array, including for example, variations in the number, dimensions, shape, and metal composition of the individual electrodes, as well as the distance and constancy of distance between electrodes, within each array. Further, each array may have the same or completely different designs.

While the neurostimulation system has been described for implantation as a peripheral neurostimulator in the head and for head pain, it is capable of being implanted and used as a peripheral nerve stimulator over other regions of the head and face than described above and also over other peripheral nerves in the body.

Certain embodiments may incorporate an adjustable voltage generation circuit (e.g., a buck/boost circuit as shown in FIG. 17 and FIG. 20) that utilizes a local power supply voltage, such as a battery voltage, to generate a VBOOST voltage that is typically higher in voltage than the local power supply. However, the VBOOST voltage in certain embodiments may be higher or lower than the local power supply voltage, depending upon the battery voltage, the desired energy transfer to the body-implanted active devices, and other factors.

Q. Operation

When functioning, the implanted neurostimulator is functionally connected to the ECU by an RF couple, the internal circuit of lead internal wires is connected to an IPG, and the SME of the various arrays are programmed to function as anodes and cathodes. The generated electrical pulse wave then passes from the ASIC of the IPG to the associated internal lead wire and ultimately to its associated terminal surface metal electrode. The current then passes a short distance from the subcutaneous tissue to a contiguous, or nearby, electrode, whereby it passes back up the lead to its associated proximal metal contact, and then back to the IPG to complete the circuit. The generated pulse waves pass through the subcutaneous tissue between two terminal electrodes and stimulate the sensory nerves of the area. When active, the IPG may be programmed to produce continuous series of pulse waves of specified frequency, amplitude, and pulse width. It is this series of pulse waves actively stimulating a patient's locally associated nerves that underpins the therapeutic effect of the implanted unit. The electrical pulse wave then passes from a connected proximal surface metal contact, along the associated internal lead wire, and ultimately to its associated terminal surface metal contact.

Figure 28:
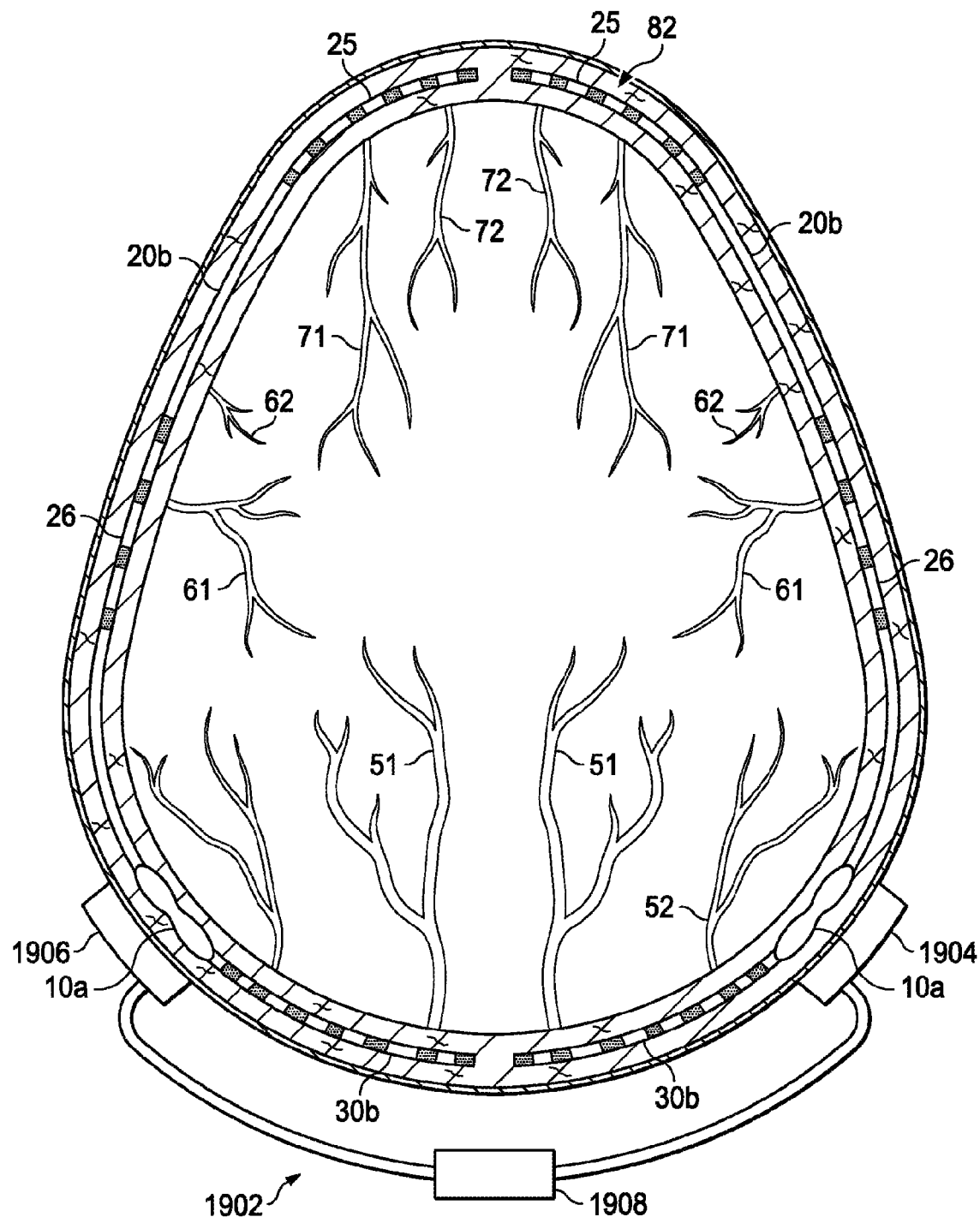
FIG. 28 illustrates the embodiment of FIG. 26 with a charging/communication headset disposed about the cranium.

Referring now to FIG. 28, there is illustrated a headset 1902 disposed about the cranium for interfacing with the two implants 10a of FIG. 26. The headset 1902 includes right and left coupling coil enclosures 1904 and 1906, respectively that contain coils coupled to the respective coils in the implants 10a. The coil enclosures 1904 and 1906 interface with a main charger/processor body 1908 which contains processor circuitry and batteries for both charging the internal battery in the implants 10a and also communicating with the implants 10a. Thus, in operation, when a patient desires to charge their implants 10a, all that is necessary is to place the headset 1902 about the cranium with the coil enclosures 1904 and 1906 in close proximity to the respective implants 10a. This will automatically effect charging.

Figure 29:
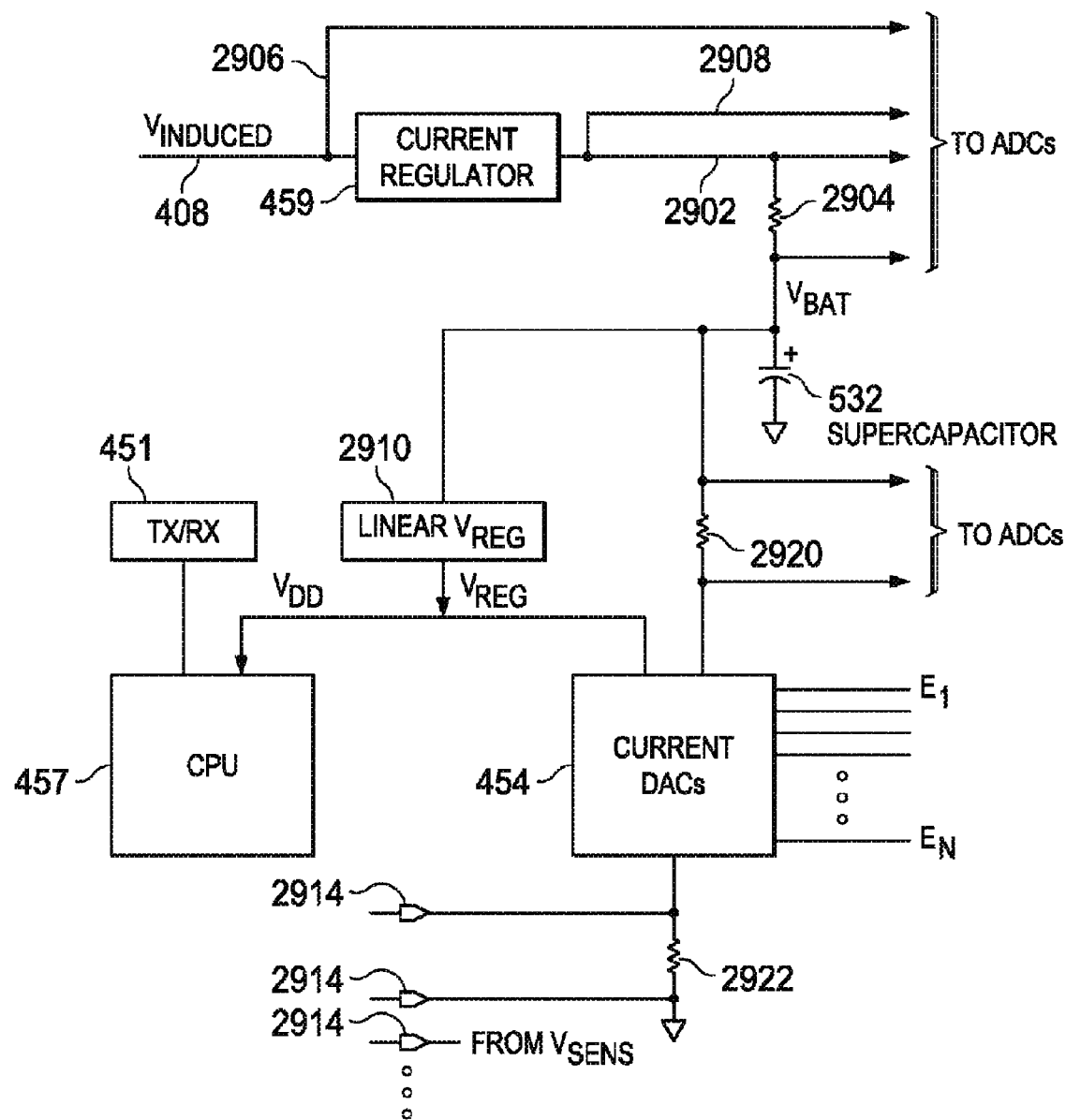
FIG. 29 illustrates a diagrammatic view of the power regulation system and current regulation system on the IPG.

Referring now to FIG. 29, there is illustrated a diagrammatic view of the power regulation system at the IPG. As noted hereinabove, the original rectified voltage is the "raw" voltage that is received from the headset via the inductive coupling. This is provided on the node 408. As noted hereinabove also, this drives the current regulator 459, which is operable to output a regulated current on a node 2902. This is operable to drive the supercapacitor 532, with the voltage noted as $V_{BAT}$ for the overall storage voltage, it being understood that the supercapacitor 532 could be replaced with a regular battery. The current regulator 459 is a logic circuit that will operate on any voltage. Thus, when the voltage is input thereto and rises above a predetermined threshold voltage above which the regulator 459 will maintain current regulation, the current provided to the node 2902 will be regulated at, in an exemplary disclosed embodiment, 30 mA. This is utilized to charge the supercapacitor 532 and to minimize the maximum output current that can be sinked to the supercapacitor 532. The reason for this is to minimize the amount of power delivered through the inductive coupling to the IPG. If there were no limit on the amount of current, then the supercapacitor would be charged at a very high rate initially until it reached its maximum charge at the voltage applied. Thus, the current regulator 459 is operable to charge the supercapacitor 532 up to its maximum charge level, which will be the maximum voltage applied on the node 2902. As will be described hereinbelow, the voltage on the node 408, the induced voltage, $V_{INDUCED}$, will be maintained at a level that will be sufficiently above the voltage on the node 2902 to maintain current regulation. This is typically a voltage of 1.0 Volts, but this depends upon the design of the current regulator 459. There is also provided a resister 2904 disposed in series between the node 2902 and the upper plate of the supercapacitor 532. This is an alternative current sensing resistor which has a very small value of, for example, 0.1 ohms. By measuring the voltage across this resistor 2904, a measurement of the current delivered directly to the supercapacitor 532 can be determined. Additionally, there are provided to sensing lines 2906 and 2908 for measuring the voltage across the current regulator 459. With knowledge of the voltage drop across the current regulator 459 required to maintain regulation, it would then be possible to maintain the voltage on the node 408 slightly at or above that voltage in order to maintain current regulation. Of course, as the supercapacitor 532 charges, the voltage will increase, requiring the voltage on the node 408 to be increased.

The CPU 457 and the current driver 454 (the current driver being realized with current DACs) are logic circuits that required a fixed operating voltage, below which they will not operate. Thus, there is provided a linear regulator 2910 which is operable to provide an operating voltage, $V_{DD}$, for operating all of the logic circuit and the current driver 454 in the ASIC. When the voltage falls below $V_{DD}$, the logic associated with the circuits will not operate and that they will be placed into some type of hibernating or sleep mode. When the voltage on the supercapacitor 532 rises above the level that allows the linear regulator 2910 to regulate the voltage to $V_{DD}$, the CPU 457 will go into a Power Up Reset mode of operation and initiate the operation of the IPG to run the programmed stimulation. Once operational, it will also be able to communicate with the headset via the transceiver 451.

During operation, the CPU 457 is operable to determine the various voltages associated with the current sensing operation. The minimum that is required is to sense the voltage on the lines 2906 and 2908. These voltages are input to ADCs 2914 to provide a digital voltage for the CPU 457 to encode and transferred to the headset. As noted above, the resistor 2904 could be an alternate current sensing element that measures the direct current to the supercapacitor 532. Additionally, it is desirable to sense the current to the current DACs 454 both to the anodes via a sensing resistor 2920 and from the cathodes via a sensing resistor 2922. Each of these has an associated set of sensing lines that are input to an associated one of the ADCs 2914. Thus, the CPU 457 can provide to the headset voltage information regarding the voltage drop across the current regulator 459, the voltage drop across the sensing resistor 2904, the voltage drop across the sensing resistor 2920 and the voltage drop across the sensing resistor 2922.

In operation, the supercapacitor 532 is charged up and provides the necessary driving current to the rest of the circuit during operation. During operation of the IPG and driving of the electrodes $E_1$-$E_N$ to provide the stimulation to the associated nerves, current is drawn off of the supercapacitor 532 by the logic circuitry associated with the CPU 457 and the ASIC and also by the driving current required to drive the electrodes. The maximum current for this is approximately 3.0 mA. Depending upon the size of the supercapacitor 532, there will be a finite time within which the supercapacitor 532 will require additional charge to be provided by the current regular 459. Initially, upon connection of a headset, the supercapacitor 532 might have an operation where it is desirable to quickly charge the supercapacitor 532 to the maximum voltage. After this initial charge, required in order to get the IPG up and running quickly, any replenishment of this charge might not require 30 mA of charge but, rather, a lower charge rate. This lower charge rate could be affected by pulsing in the induced voltage or having a current regulator with a lower voltage drop associated therewith. Thus, a variable current current regulator 459 could be implemented. The whole purpose is to reduce the amount of voltage on the node 408 to the minimum amount required for the overall operation to reduce any heating at the inductive coupled point across the skin.

Figure 30:
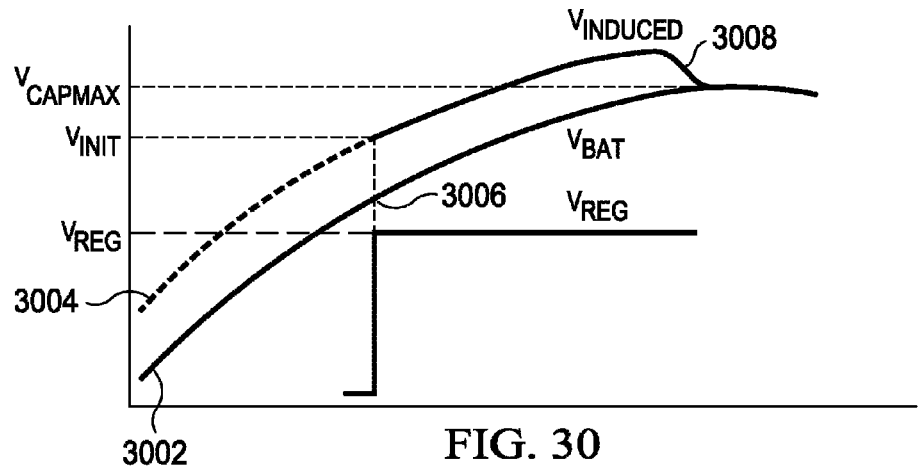
FIG. 30 illustrates a diagrammatic view of the voltage charging relationships for the supercapacitor.

Referring now to FIG. 30, there is illustrated a diagrammatic view of the voltage during charging. Initially, when the supercapacitor 532 is discharged below the required voltage for the linear regulator 2910, the IPG will be powered down. This is represented by a voltage 3002. In order to increase his voltage, the induced voltage from the headset must be at least, in one example, 1.0 Volts above the voltage of node 2902. This will allow 30 mA of current to flow through the current right regulator 459. Thus, if the headset were intelligent enough to provide a time to increase to follow charging pattern of the supercapacitor 532, it would follow a dotted line 3004. However, the headset does not have knowledge of this. Thus, a predetermined voltage, $V_{INIT}$, will be applied as the induced voltage 408. This would be a voltage that was known to be above required to operate the linear regulator 2910. However, it should be understood that the voltage required by a headset in order to have an induced voltage at a particular level can be affected by multiple factors such as the positioning of the headset relative to the IPG, the particular manner by which the IPG was implanted in a particular patient, etc. Thus, the voltage can initially be increased well above the worst-case to scenario. This will allow the voltage on the node 2904 to increase from the voltage 3002 up to a voltage at a point 3006 that represents the point at which the linear regulator 2910 will provide operating voltage to CPU 457. At this point, voltages across the current regulator 459 or any of the sensing resistors 2904, 2924 2922, can be transmitted to the headset. The headset can then decrease the voltage or increase the voltage to influence the voltage on the node 408 to maintain that induced voltage as low as possible in order to maintain current regulation on the current regulator 459. This will continue until the supercapacitor 532 is fully charged, at a point 3008. There can be some hysteresis programmed into the operation of the headset such that the voltage on the supercapacitor 532, i.e., the voltage on the node 2902, will have to decrease by a predetermined percentage before additional charging will be effected by an increase in the voltage on node 408. At the point 3006, the regulated voltage is output to the CPU 457.

Figure 31:
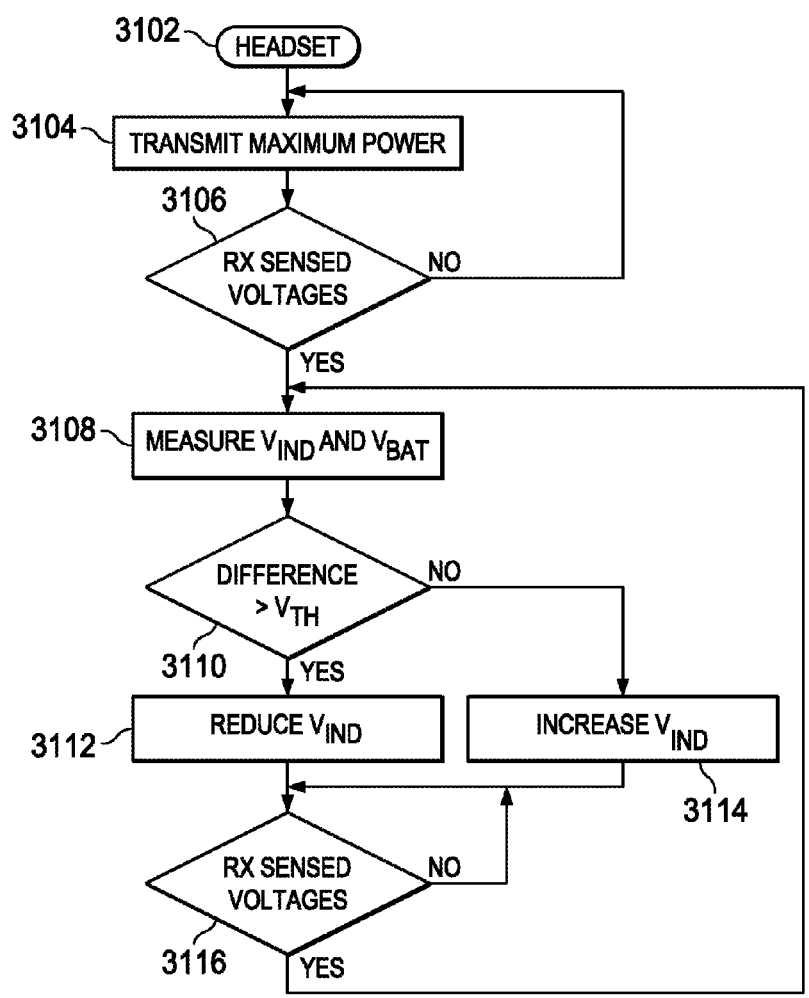
FIG. 31 illustrates a flowchart for power transfer system from the headset.

Referring now to FIG. 31, there is illustrated a flowchart for the operation of the headset. The operation is initiated at a block 3102 and then proceeds to a block 3104 wherein the maximum power is transmitted, i.e., that being the power required to provide the initial voltage on the node 408. This could be the maximum voltage of the headset or could be an intermediate voltage that was predetermined. The program then flows to a decision block 3106 to determine if the CPU 457 is transmitting information regarding sensed voltages. If not, the program loops back to a block 3104 to provide the initial charging power to the supercapacitor 532. Once sensed voltages have been received, this is an indication that the CPU 457 is operating and that the headset can vary the voltage to ensure that only the minimum amount of voltage is induced on the node 408 in order to maintain current regulation. Anything above that results both in dissipation of heat in the current regulator 459 and also unwanted conductivity in the coils. The program, after the sensed voltages have been received, flows to a block 3108 to measure the induced voltage and the battery voltage at the minimum. As noted hereinabove, all of the other sensed voltages associated with operation of the system could also be sensed. The program then flows to a decision block 3110 to determine if the difference in the voltage is greater than a predetermined threshold voltage. If yes, then the program flows to a block 3112 in order to reduce the induced voltage and, if not, the program flows to a block 3114 to increase the induced voltage. The program then flows to a decision block 3116 in order to wait for the next transmitted sensed voltages, which are periodically measured and transmitted by the CPU 457. In general, however, this is a polled system. The IPGs, whether there are one or two IPGs, are given addresses and requests sent to a particular IPG for information regarding its sensed voltage. Alternatively, a request can be sent to a particular IPG for any information it has queued up for transmission. Thus, a request is sent to an IPG and then a certain period of time is allowed for receipt of that information. Thus, when the charging operation is initiated, the maximum power is transmitted along with periodic requests for information. Until this information is received, no changes are made to the power. Once information is received, the voltages are measured, in this operation, in order to determine whether the voltage should be increased or decreased.

In the overall charging operation, the initial charge is approximately 30 mA and the voltage is adjusted to maintain this 30 mA with the minimum level of an induced voltage on node 408. Once the supercapacitor 532 is fully charged, is only necessary to maintain a current of approximately 3 mA. Since the supercapacitor 532 is provided for buffering and storing charge, it is only necessary to periodically recharge supercapacitor 532. Thus, once charged, as indicated by the receive voltage on the node 2902, the headset can make a determination that the charge is above the charge necessary to maintain regulation operation of the linear regulator 2910. As long as the voltage on the supercapacitor 532 is above that voltage, no additional charge is required. Thus, by monitoring this voltage, a certain level can be determined, below which the headset will again increase the voltage at the headset to maintain the induced voltage on the node 408 above the threshold necessary to drive 30 mA to the supercapacitor 532. In this operation, the amount of current driven to the IPG is managed to reduce unnecessary heating in both the IPG and at the inductive interface.

Certain embodiments disclosed herein may be described as including an external charging system (or external charge transfer system) for charging (or transferring charge to) one or more implantable devices. Strictly speaking, in the described embodiments using a transmit coil and a receive coil, energy is stored per cycle as a magnetic field in the transmit coil, and some of this energy is transferred per cycle by magnetic induction to the receive coil. In other words, energy is transferred over a certain duration of time from the transmit coil to the receive coil, and the rate of such energy transfer is power. However, the words "energy" and "power" are frequently used somewhat interchangeably when describing a magnetic induction circuit, since a circuit that transfers power (i.e., at a certain rate) also transfers a corresponding amount of energy over a duration of time. As such, disabling power transfer also likewise disables energy transfer when disabled for a certain period of time. Moreover, reducing power transfer also likewise reduces energy transfer over a period of time. For this reason, in context there is seldom confusion between usage of the phrases "transferred energy" and "transferred power", or between the phrases "received energy" and "received power," as it is usually clear in context whether the reference is to total transfer over a duration of time, or to an instantaneous rate of transfer.

The phrases "power transfer" or "energy transfer" may also be somewhat informally referred to as "charge transfer" because such transferred charge may be for delivering power, in the form of a current (i.e., moving electronic charge) at a certain voltage, to operate circuitry within the implantable device, in addition to (or instead of) charging a supercapacitor, battery, or other charge storage device within the implantable device. Consequently, as used herein, an external charging system may also be viewed as an external charge transfer system or an external power transfer system, and references herein to an external charging system, an external charge transfer system, and an external power transfer system may be used interchangeably with no specific distinction intended unless clear in the context of such use, even if no charge storage device is "charged" in a given embodiment. Similarly, a charge receiving system may also be viewed as a power receiving system, and references herein to a charge receiving system and a power receiving system may be used interchangeably with no specific distinction intended unless clear in the context of such use.

It is to be understood that the implementations disclosed herein are not limited to the particular systems or processes described which might, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise.

As used herein, "exemplary" is used interchangeably with "an example." For instance, an exemplary embodiment means an example embodiment, and such an example embodiment does not necessarily include essential features and is not necessarily preferred over another embodiment. As used herein, "coupling" includes direct and/or indirect coupling of circuit components, structural members, etc. As used herein, a group of one or more transmit coils disposed in series can mean only one transmit coil, or can mean two or more transmit coils disposed in series.

Regarding terminology used herein, it will be appreciated by one skilled in the art that any of several expressions may be equally well used when describing the operation of a circuit including the various signals and nodes within the circuit. Any kind of signal, whether a logic signal or a more general analog signal, takes the physical form of a voltage level (or for some circuit technologies, a current level) of a node within the circuit. Such shorthand phrases for describing circuit operation used herein are more efficient to communicate details of circuit operation, particularly because the schematic diagrams in the figures clearly associate various signal names with the corresponding circuit blocks and nodes.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

It will be appreciated by those skilled in the art having the benefit of this disclosure that this implantable neurostimulation system for head pain provides an implantable neurostimulation system having a plurality of electrode arrays spaced along a portion of its length such that when neurostimulation lead is implanted, at least one electrode array is positioned over the frontal region, at least one electrode array is positioned over the parietal region, and at least one electrode array is positioned over the occipital region of the patient's cranium so that when the neurostimulation lead is connected to an implantable pulse generator, the single lead can provide medically acceptable neurostimulation coverage over the supraorbital, the auriculotemporal, and the occipital nerves unilaterally. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A system for driving at least two implantable neurostimulator leads, each having a plurality of electrodes disposed in at least one array, comprising:
    at least two implantable pulse generators (IPGs), each respectively including:
        an electrode driver for driving the electrodes,
        a current limiting current regulator for limiting the current to the IPG,
        a load system for determining a minimum load requirement of the IPG to provide the necessary power to the current regulator,
        an IPG power coupler for receiving power across a dermis layer for interface of the power with the electrode driver, and
        an IPG communication system for transmitting the determined minimum load requirement of the IPG across the dermis layer; and
    an external unit including:
        an external variable power generator,
        an external power coupler for coupling power across the dermis layer to each respective IPG power coupler,
        an external communication system for polling each respective IPG, and in response thereto, for receiving from each respective IPG communication system the determined minimum load requirement of the respective IPG, and
        a controller for varying the power level of the variable power generator as a function of the received determined minimum load requirement of each respective IPG.

2. The system of claim 1, wherein each respective electrode driver drives the respective electrodes with a constant current.

3. The system of claim 1, wherein each respective load system comprises:
    a detector for detecting the state of the current regulator; and
    a processor for determining the necessary power from the external unit required by the electrode driver as the determined minimum load requirement of the IPG to maintain the current regulator in regulation.

4. The system of claim 3, wherein each respective current regulator delivers a predetermined constant current.

5. The system of claim 4, wherein the determined minimum load requirement comprises at least enough power from the external unit to provide the predetermined constant current from the current regulator.

6. The system of claim 1, wherein each respective IPG further includes a charge storage device.

7. The system of claim 1, wherein each respective IPG is head-located beneath the dermis layer of a patient.

8. The system of claim 1, wherein each respective IPG communication system comprises at least one coil and the external communication system comprises at least two series-connected coils, each such series-connected coil corresponding to a respective IPG.

9. A system for driving a plurality of implantable neurostimulator leads, each lead having an associated plurality of electrodes disposed in at least one array on the lead, the system comprising:
    at least two implantable pulse generators (IPGs), each IPG including:
        an electrode driver for driving the electrodes associated with the IPG,
        a current limiting current regulator for limiting the current to the IPG,
        a load system for determining a minimum load requirement of the IPG to provide the necessary power to the current regulator,
        an IPG power coupler for receiving power across a dermis layer for interface of the power with the electrode driver of the IPG, and
        an IPG communication system for transmitting the determined minimum load requirement of the IPG across the dermis layer; and
    an external unit for providing power to the at least two IPGs, the external unit including:
        an external variable power generator,
        an external power coupler for coupling power across the dermis layer to the IPG power couplers,
        an external communication system for polling each respective IPG, and for receiving from each respective IPG communication system, in response to being polled, the respective determined minimum load requirement of the respective IPG, and
        a controller for varying the power level of the variable power generator as a function of the received determined minimum load requirement of the IPG with the greatest minimum load requirement.

10. The system of claim 9, wherein the communication systems of each IPG is operable to transmit the determined minimum load requirement to the external communication system independently of the communication systems of each of the other IPGs.

11. The system of claim 9, wherein each of the IPG communication systems transmit its respective determined minimum load requirement to the external unit communication system inductively.

12. The system of claim 9, wherein each IPG power coupler is for receiving levels of power across a dermis layer that are independent of the levels of power received by the power couplers of each of the other IPGs.

13. The system of claim 9, wherein at least one of the IPGs further includes a charge storage device.

14. The system of claim 9, wherein each respective IPG communication system comprises at least one coil and the external communication system comprises at least two series-connected coils, each such series-connected coil corresponding to a respective IPG.

15. A neurostimulation system comprising:
    at least two implantable pulse generators (IPGs), each IPG including:
        an electrode driver for driving a plurality of electrodes associated with the IPG,
        a load system operable to determine a minimum load requirement of the IPG,
        an IPG power coupler operable to receive power across a dermis layer for interface of the power with the electrode driver of the IPG, and
        an IPG communication system operable to transmit, in response to receiving a request, the determined minimum load requirement of the IPG across the dermis layer; and
    an external unit for providing power to the at least two IPGs, the external unit including:
        an external variable power generator,
        an external power coupler operable to couple power from the external variable power generator across the dermis layer to the IPG power couplers,
        an external communication system operable to send a respective request to each respective IPG communication system, and receive from each respective IPG communication system, in response to such request, the respective determined minimum load requirement of the respective IPG, and
        a controller operable to vary the power level of the variable power generator as a function of the received determined minimum load requirement of the IPG with the greatest minimum load requirement.

16. The system of claim 15, wherein the communication systems of each IPG is operable to transmit the determined minimum load requirement to the external communication system independently of the communication systems of each of the other IPGs.

17. The system of claim 15, wherein each of the IPG communication systems transmits its respective determined minimum load requirement to the external unit communication system inductively.

18. The system of claim 15, wherein each IPG power coupler is operable to receive levels of power across a dermis layer that are independent of the levels of power received by the power couplers of each of the other IPGs.

19. The system of claim 15, wherein each IPG further includes a charge storage device.

20. The system of claim 15, wherein each respective IPG comprises at least one coil coupled to both the IPG communication system and the IPG power coupler, and the external unit comprises at least two series-connected coils together shared by the external communication system and the external power coupler, each such series-connected coil corresponding to a respective IPG.

* * * * *